(12) United States Patent
Tygesen et al.

(10) Patent No.: US 9,358,295 B2
(45) Date of Patent: *Jun. 7, 2016

(54) IMMEDIATE RELEASE COMPOSITION RESISTANT TO ABUSE BY INTAKE OF ALCOHOL

(71) Applicant: Egalet Ltd., London (GB)

(72) Inventors: Peter Holm Tygesen, Smoerum (DK); Jan Martin Oevergaard, Frederikssund (DK); Joakim Oestman, Lomma (SE)

(73) Assignee: EGALET LTD., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/656,016

(22) Filed: Mar. 12, 2015

(65) Prior Publication Data

US 2015/0313997 A1    Nov. 5, 2015

Related U.S. Application Data

(63) Continuation of application No. 12/701,248, filed on Feb. 5, 2010, now Pat. No. 9,005,660.

(60) Provisional application No. 61/150,577, filed on Feb. 6, 2009, provisional application No. 61/151,491, filed on Feb. 10, 2009.

(30) Foreign Application Priority Data

Feb. 6, 2009  (DK) .................... 2009 00190

(51) Int. Cl.
| | | |
|---|---|---|
| A61K 9/46 | (2006.01) | |
| A61K 9/16 | (2006.01) | |
| A61K 31/44 | (2006.01) | |
| A61K 31/16 | (2006.01) | |
| A61K 31/485 | (2006.01) | |
| A61K 31/167 | (2006.01) | |
| A61K 9/28 | (2006.01) | |
| A61K 9/20 | (2006.01) | |
| A61K 47/10 | (2006.01) | |
| A61K 47/02 | (2006.01) | |
| A61K 47/12 | (2006.01) | |

(52) U.S. Cl.
CPC .............. *A61K 47/10* (2013.01); *A61K 9/0007* (2013.01); *A61K 9/2031* (2013.01); *A61K 9/2866* (2013.01); *A61K 9/2893* (2013.01); *A61K 31/167* (2013.01); *A61K 31/485* (2013.01); *A61K 47/02* (2013.01); *A61K 47/12* (2013.01); *A61K 9/2095* (2013.01)

(58) Field of Classification Search
USPC ............ 424/466, 495; 514/282, 629
See application file for complete search history.

(56) References Cited

U.S. PATENT DOCUMENTS

| | | |
|---|---|---|
| 2,685,553 A | 8/1954 | Carroll et al. |
| 3,835,221 A | 9/1974 | Fulberth et al. |
| 3,957,523 A | 5/1976 | Ohno et al. |
| 4,034,758 A | 7/1977 | Theeuwes |
| 4,330,338 A | 5/1982 | Banker |
| 4,389,393 A | 6/1983 | Schor et al. |
| 4,404,183 A | 9/1983 | Kawata et al. |
| 4,449,983 A | 5/1984 | Cortese et al. |
| 4,503,067 A | 3/1985 | Wiedemann et al. |
| 4,686,212 A | 8/1987 | Ducatman et al. |
| 4,824,675 A | 4/1989 | Wong et al. |
| 4,844,984 A | 7/1989 | Eckenhoff et al. |
| 4,873,080 A | 10/1989 | Brickl et al. |
| 4,892,742 A | 1/1990 | Shah |
| 4,898,733 A | 2/1990 | De Prince et al. |
| 5,019,396 A | 5/1991 | Ayer et al. |
| 5,068,112 A | 11/1991 | Samejima et al. |
| 5,082,655 A | 1/1992 | Snipes et al. |
| 5,102,668 A | 4/1992 | Eichel et al. |
| 5,213,808 A | 5/1993 | Bar-Shalom et al. |
| 5,266,331 A | 11/1993 | Oshlack et al. |
| 5,281,420 A | 1/1994 | Kelm et al. |
| 5,352,455 A | 10/1994 | Robertson |
| 5,411,745 A | 5/1995 | Oshlack et al. |
| 5,419,917 A | 5/1995 | Chen et al. |
| 5,422,123 A | 6/1995 | Conte et al. |
| 5,460,826 A | 10/1995 | Merrill et al. |
| 5,478,577 A | 12/1995 | Sackler et al. |
| 5,508,042 A | 4/1996 | Oshlack et al. |
| 5,520,931 A | 5/1996 | Persson et al. |
| 5,529,787 A | 6/1996 | Merrill et al. |
| 5,549,912 A | 8/1996 | Oshlack et al. |
| 5,593,695 A | 1/1997 | Merrill et al. |
| 5,609,885 A | 3/1997 | Rivera et al. |
| 5,614,218 A | 3/1997 | Olsson et al. |
| 5,618,560 A | 4/1997 | Bar-Shalom et al. |
| 5,656,291 A | 8/1997 | Olsson et al. |

(Continued)

FOREIGN PATENT DOCUMENTS

| | | |
|---|---|---|
| EP | 0435726 | 8/1991 |
| EP | 0493513 | 7/1992 |

(Continued)

OTHER PUBLICATIONS

U.S. Appl. No. 13/900,933, filed Aug. 25, 2006, Purdue Pharma C.
Bravo et al., "In-vitro studies of diclofenac sodium controlled-release from biopolymeric hydrophilic matrices," *J. Pharmaceutical Science*, vol. 5, No. 3, pp. 213-219 (2002).
The Condensed Chemical Dictionary, "mixture," 9th edition, p. 584 (1977).
Giunchedi et al., "Hydrophilic matrices for the extended release of a model drug exhibiting pH-dependent solubility," *International Journal of Pharmaceutics*, vol. 85, pp. 141-147 (1992).

(Continued)

*Primary Examiner* — Shirley V Gembeh
(74) *Attorney, Agent, or Firm* — Foley & Lardner LLP

(57) ABSTRACT

The present invention provides immediate release pharmaceutical compositions for oral administration that are resistant to abuse by intake of alcohol.

19 Claims, 23 Drawing Sheets

(56) References Cited

U.S. PATENT DOCUMENTS

Figure 1:
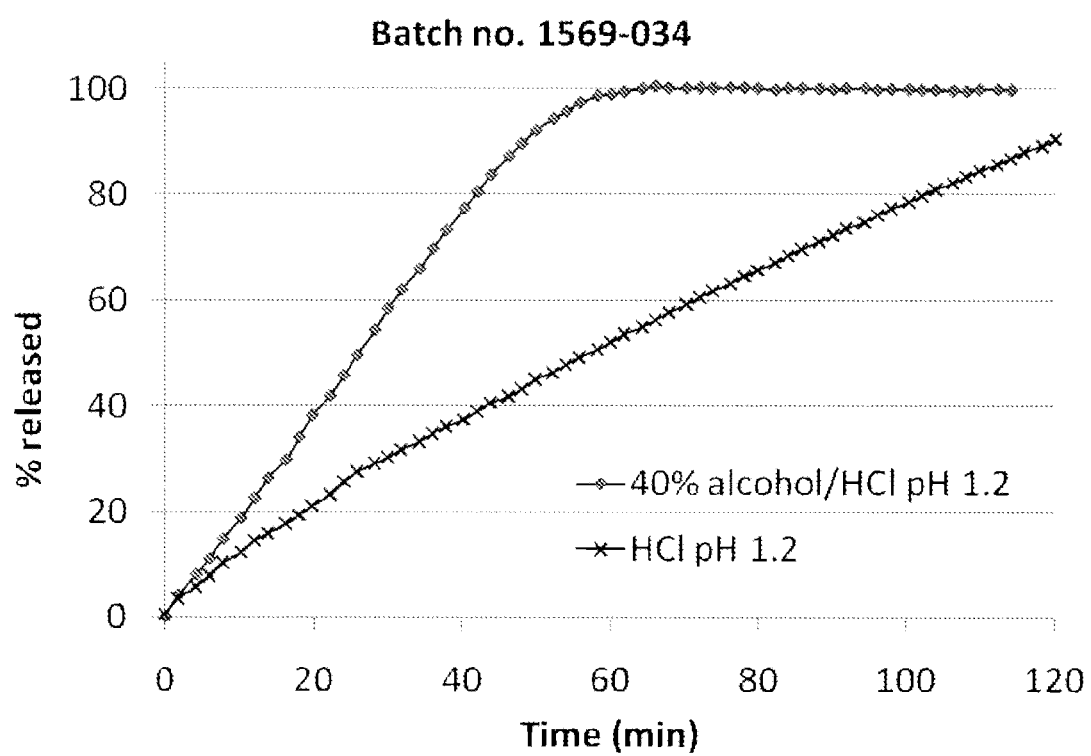

| | | |
|---|---|---|
| 5,656,295 A | 8/1997 | Oshlack et al. |
| 5,667,805 A | 9/1997 | Merrill et al. |
| 5,672,360 A | 9/1997 | Sackler et al. |
| 5,741,524 A | 4/1998 | Staniforth et al. |
| 5,866,161 A | 2/1999 | Childers et al. |
| 5,866,164 A | 2/1999 | Kuczynski et al. |
| 5,869,097 A | 2/1999 | Wong et al. |
| 5,879,705 A | 3/1999 | Heafield et al. |
| 5,882,682 A | 3/1999 | Rork et al. |
| 5,914,131 A | 6/1999 | Merrill et al. |
| 5,948,787 A | 9/1999 | Merrill et al. |
| 5,952,005 A | 9/1999 | Olsson et al. |
| 5,968,551 A | 10/1999 | Oshlack et al. |
| 6,046,177 A | 4/2000 | Stella et al. |
| 6,066,339 A | 5/2000 | Stark et al. |
| 6,077,533 A | 6/2000 | Oshlack et al. |
| 6,077,538 A | 6/2000 | Merrill et al. |
| 6,103,261 A | 8/2000 | Chasin et al. |
| 6,117,453 A | 9/2000 | Seth et al. |
| 6,143,328 A | 11/2000 | Heafield et al. |
| 6,183,778 B1 | 2/2001 | Conte et al. |
| 6,225,343 B1 | 5/2001 | Behl et al. |
| 6,245,351 B1 | 6/2001 | Nara et al. |
| 6,245,357 B1 | 6/2001 | Edgren et al. |
| 6,267,981 B1 | 7/2001 | Okamoto et al. |
| 6,267,985 B1 | 7/2001 | Chen et al. |
| 6,277,384 B1 | 8/2001 | Kaiko et al. |
| 6,284,274 B1 | 9/2001 | Merrill et al. |
| 6,294,195 B1 | 9/2001 | Oshlack et al. |
| 6,348,216 B1 | 2/2002 | Kushla et al. |
| 6,375,957 B1 | 4/2002 | Kaiko et al. |
| 6,383,471 B1 | 5/2002 | Chen et al. |
| 6,395,299 B1 | 5/2002 | Babich et al. |
| 6,399,096 B1 | 6/2002 | Miller et al. |
| 6,403,579 B1 | 6/2002 | Heller |
| 6,451,848 B1 | 9/2002 | Behl et al. |
| 6,458,772 B1 | 10/2002 | Zhou et al. |
| 6,458,824 B1 | 10/2002 | Iwata et al. |
| 6,475,494 B2 | 11/2002 | Kaiko et al. |
| 6,482,437 B2 | 11/2002 | Debregeas et al. |
| 6,488,962 B1 | 12/2002 | Berner et al. |
| 6,488,963 B1 | 12/2002 | McGinity et al. |
| 6,491,945 B1 | 12/2002 | Childers et al. |
| 6,517,866 B1 | 2/2003 | Am Ende et al. |
| 6,534,085 B1 | 3/2003 | Zeligs |
| 6,543,085 B2 | 4/2003 | Holsten et al. |
| 6,562,375 B1 | 5/2003 | Sako et al. |
| 6,572,885 B2 | 6/2003 | Oshlack et al. |
| 6,599,531 B2 | 7/2003 | Kushla et al. |
| 6,607,751 B1 | 8/2003 | Odidi et al. |
| 6,632,832 B1 | 10/2003 | Burman et al. |
| 6,673,816 B1 | 1/2004 | Esswein et al. |
| 6,685,964 B1 | 2/2004 | Bartholomaeus et al. |
| 6,696,066 B2 | 2/2004 | Kaiko et al. |
| 6,709,678 B2 | 3/2004 | Gruber |
| 6,730,326 B2 | 5/2004 | Beyer et al. |
| 6,733,783 B2 | 5/2004 | Oshlack et al. |
| 6,757,558 B2 | 6/2004 | Lange et al. |
| 6,787,156 B1 | 9/2004 | Bar-Shalom |
| 6,800,668 B1 | 10/2004 | Odidi et al. |
| 6,837,696 B2 | 1/2005 | Sowden et al. |
| 6,852,337 B2 | 2/2005 | Gabel et al. |
| 6,960,357 B2 | 11/2005 | Chopra |
| 7,060,293 B1 | 6/2006 | Oshlack et al. |
| 7,063,864 B1 | 6/2006 | Marechal et al. |
| 7,090,867 B2 | 8/2006 | Odidi et al. |
| 7,144,587 B2 | 12/2006 | Oshlack et al. |
| 7,172,767 B2 | 2/2007 | Kaiko et al. |
| 7,201,920 B2 | 4/2007 | Kumar et al. |
| 7,270,831 B2 | 9/2007 | Oshlack et al. |
| 7,332,182 B2 | 2/2008 | Sackler |
| 7,399,488 B2 | 7/2008 | Hirsh et al. |
| 7,419,686 B2 | 9/2008 | Kaiko et al. |
| 7,476,402 B2 | 1/2009 | Kumar et al. |
| 7,510,726 B2 | 3/2009 | Kumar et al. |
| 7,510,727 B2 | 3/2009 | Oshlack et al. |
| 7,514,100 B2 | 4/2009 | Oshlack et al. |
| 7,666,337 B2 | 2/2010 | Yang et al. |
| 7,749,542 B2 | 7/2010 | Kaiko et al. |
| 7,771,707 B2 | 8/2010 | Hirsh et al. |
| 7,776,314 B2 | 8/2010 | Bartholomaus et al. |
| 7,842,307 B2 | 11/2010 | Oshlack et al. |
| 7,846,476 B2 | 12/2010 | Oshlack et al. |
| 7,883,722 B2 | 2/2011 | Bar-Shalom |
| 7,883,772 B2 | 2/2011 | Pourdeyhimi et al. |
| 7,897,080 B2 | 3/2011 | Yang et al. |
| 7,906,143 B1 | 3/2011 | Odidi et al. |
| 7,943,174 B2 | 5/2011 | Oshlack et al. |
| 7,968,120 B2 | 6/2011 | Li et al. |
| 7,972,624 B2 | 7/2011 | Li et al. |
| 7,981,439 B2 | 7/2011 | Kumar et al. |
| 8,017,148 B2 | 9/2011 | Sackler |
| 8,017,150 B2 | 9/2011 | Yang et al. |
| 8,029,822 B2 | 10/2011 | Faour et al. |
| 8,075,872 B2 | 12/2011 | Arkenau-Marie et al. |
| 8,101,630 B2 | 1/2012 | Kumar et al. |
| 8,105,631 B2 | 1/2012 | Kaiko et al. |
| 8,114,383 B2 | 2/2012 | Bartholomaus et al. |
| 8,114,384 B2 | 2/2012 | Arkenau et al. |
| 8,133,507 B2 | 3/2012 | Yum et al. |
| 8,142,811 B2 | 3/2012 | Oshlack et al. |
| 8,147,870 B2 | 4/2012 | Yum et al. |
| 8,153,152 B2 | 4/2012 | Yum et al. |
| 8,168,217 B2 | 5/2012 | Yum et al. |
| 8,173,152 B2 | 5/2012 | Crowley et al. |
| 8,182,836 B2 | 5/2012 | Mehta |
| 8,192,722 B2 | 6/2012 | Arkenau-Maric et al. |
| 8,231,898 B2 | 7/2012 | Oshlack et al. |
| 8,246,986 B2 | 8/2012 | Cruz et al. |
| 8,309,060 B2 | 11/2012 | Bartholomaus et al. |
| 8,323,889 B2 | 12/2012 | Arkenau-Maric et al. |
| 8,329,720 B1 | 12/2012 | King et al. |
| 8,337,888 B2 | 12/2012 | Wright et al. |
| 8,338,444 B1 | 12/2012 | King et al. |
| 8,354,124 B2 | 1/2013 | Yum et al. |
| 8,361,499 B2 | 1/2013 | Oshlack et al. |
| 8,367,693 B1 | 2/2013 | King et al. |
| 8,372,432 B2 | 2/2013 | Han et al. |
| 8,377,453 B2 | 2/2013 | Han et al. |
| 8,383,152 B2 | 2/2013 | Jans et al. |
| 8,383,154 B2 | 2/2013 | Bar-Shalom |
| 8,383,155 B2 | 2/2013 | Bar-Shalom |
| 8,389,007 B2 | 3/2013 | Wright et al. |
| 8,394,407 B2 | 3/2013 | Vergnault et al. |
| 8,394,408 B2 | 3/2013 | Han et al. |
| 8,409,616 B2 | 4/2013 | Kumar et al. |
| 8,415,401 B2 | 4/2013 | Yum et al. |
| 8,420,056 B2 | 4/2013 | Arkenau-Maric et al. |
| 8,420,120 B2 | 4/2013 | Yum et al. |
| 8,425,933 B2 | 4/2013 | Mehta |
| 8,445,018 B2 | 5/2013 | Habib et al. |
| 8,449,909 B2 | 5/2013 | Hirsh et al. |
| 8,449,914 B2 | 5/2013 | Fischer et al. |
| 8,460,640 B2 | 6/2013 | Vinson et al. |
| 8,465,776 B2 | 6/2013 | Hoarau |
| 8,470,361 B2 | 6/2013 | Pettersson |
| 8,476,291 B1 | 7/2013 | King et al. |
| 8,486,423 B2 | 7/2013 | Brough et al. |
| 8,486,448 B2 | 7/2013 | Rahmouni et al. |
| 8,486,449 B2 | 7/2013 | Rahmouni et al. |
| 8,491,935 B2 | 7/2013 | Mehta et al. |
| 8,501,160 B2 | 8/2013 | Cailly-Dufestel et al. |
| 8,506,998 B2 | 8/2013 | Miller et al. |
| 8,524,275 B2 | 9/2013 | Oshlack et al. |
| 8,524,277 B2 | 9/2013 | Edgren et al. |
| 8,529,848 B2 | 9/2013 | Danehy et al. |
| 8,541,026 B2 | 9/2013 | Qiu et al. |
| 8,603,526 B2 | 12/2013 | Tygesen et al. |
| 8,609,143 B2 | 12/2013 | Fischer et al. |
| 8,609,683 B2 | 12/2013 | Wright et al. |
| 8,617,605 B2 | 12/2013 | Fischer et al. |
| 8,637,540 B2 | 1/2014 | Kumar et al. |
| 8,703,189 B2 | 4/2014 | Tomohira et al. |
| 8,765,178 B2 | 7/2014 | Parikh et al. |

(56) References Cited

U.S. PATENT DOCUMENTS

| | | |
|---|---|---|
| 8,808,745 B2 | 8/2014 | Fischer et al. |
| 8,821,928 B2 | 9/2014 | Hemmingsen et al. |
| 9,005,660 B2 | 4/2015 | Tygesen et al. |
| 2001/0036959 A1 | 11/2001 | Gabel et al. |
| 2001/0036960 A1 | 11/2001 | Decker et al. |
| 2001/0053791 A1 | 12/2001 | Babcock et al. |
| 2002/0054911 A1 | 5/2002 | Oh |
| 2002/0119197 A1 | 8/2002 | Dyar et al. |
| 2003/0035836 A1 | 2/2003 | Shanghvi et al. |
| 2003/0068375 A1 | 4/2003 | Wright et al. |
| 2003/0077320 A1 | 4/2003 | Childers et al. |
| 2003/0091635 A1 | 5/2003 | Baichwal et al. |
| 2003/0118641 A1 | 6/2003 | Maloney et al. |
| 2003/0129231 A1 | 7/2003 | Oshlack et al. |
| 2003/0133976 A1 | 7/2003 | Pather et al. |
| 2003/0203055 A1 | 10/2003 | Rao et al. |
| 2003/0224051 A1 | 12/2003 | Fink et al. |
| 2004/0010000 A1 | 1/2004 | Ayer et al. |
| 2004/0028733 A1 | 2/2004 | Tracy et al. |
| 2004/0091529 A1 | 5/2004 | Edgren et al. |
| 2004/0102476 A1 | 5/2004 | Chan et al. |
| 2004/0115262 A1 | 6/2004 | Jao et al. |
| 2004/0151772 A1 | 8/2004 | Andersen et al. |
| 2004/0202717 A1 | 10/2004 | Mehta |
| 2004/0204474 A1 | 10/2004 | Decker et al. |
| 2004/0213849 A1 | 10/2004 | Sowden et al. |
| 2004/0220250 A1 | 11/2004 | Oh et al. |
| 2004/0224020 A1 | 11/2004 | Schoenhard |
| 2004/0234602 A1 | 11/2004 | Fischer et al. |
| 2004/0253310 A1 | 12/2004 | Fischer et al. |
| 2005/0019399 A1 | 1/2005 | Fischer et al. |
| 2005/0019405 A1 | 1/2005 | Bar-Shalom |
| 2005/0020613 A1 | 1/2005 | Boehm et al. |
| 2005/0053655 A1 | 3/2005 | Yang et al. |
| 2005/0074493 A1 | 4/2005 | Mehta et al. |
| 2005/0089569 A1 | 4/2005 | Bar-Shalom |
| 2005/0089570 A1 | 4/2005 | Cruz et al. |
| 2005/0106249 A1 | 5/2005 | Hwang et al. |
| 2005/0152843 A1 | 7/2005 | Bartholomaus et al. |
| 2005/0158382 A1 | 7/2005 | Cruz et al. |
| 2005/0163837 A1 | 7/2005 | Boehm et al. |
| 2005/0169992 A1 | 8/2005 | Jao et al. |
| 2005/0236741 A1 | 10/2005 | Arkenau et al. |
| 2006/0002860 A1 | 1/2006 | Bartholomous et al. |
| 2006/0039864 A1 | 2/2006 | Barthlomaus et al. |
| 2006/0110327 A1 | 5/2006 | Emigh et al. |
| 2006/0165790 A1 | 7/2006 | Walden et al. |
| 2006/0177380 A1 | 8/2006 | Emigh et al. |
| 2006/0177507 A1 | 8/2006 | Faour et al. |
| 2006/0188447 A1 | 8/2006 | Arkenau-Maric et al. |
| 2006/0193782 A1 | 8/2006 | Bartholomaus et al. |
| 2006/0193912 A1 | 8/2006 | Ketsela et al. |
| 2006/0193914 A1 | 8/2006 | Ashworth et al. |
| 2007/0003616 A1 | 1/2007 | Arkenau-Maric et al. |
| 2007/0003617 A1 | 1/2007 | Fischer et al. |
| 2007/0003620 A1 | 1/2007 | Marechal et al. |
| 2007/0004797 A1 | 1/2007 | Weyers et al. |
| 2007/0020331 A1 | 1/2007 | Gold et al. |
| 2007/0042044 A1 | 2/2007 | Fischer et al. |
| 2007/0048228 A1 | 3/2007 | Arkenau-Maric et al. |
| 2007/0065510 A1 | 3/2007 | Odidi et al. |
| 2007/0122455 A1 | 5/2007 | Myers et al. |
| 2007/0190142 A1 | 8/2007 | Breitenbach et al. |
| 2007/0224129 A1 | 9/2007 | Guimberteau et al. |
| 2007/0231268 A1 | 10/2007 | Emigh et al. |
| 2007/0259033 A1 | 11/2007 | Cruz et al. |
| 2007/0259045 A1 | 11/2007 | Mannion et al. |
| 2007/0264326 A1 | 11/2007 | Guimberteau et al. |
| 2007/0264346 A1 | 11/2007 | Guimberteau et al. |
| 2007/0275062 A1 | 11/2007 | Oshlack et al. |
| 2007/0281003 A1 | 12/2007 | Fuisz et al. |
| 2008/0026052 A1 | 1/2008 | Schoenhard |
| 2008/0031901 A1 | 2/2008 | Qiu et al. |
| 2008/0044454 A1 | 2/2008 | Yang et al. |
| 2008/0063725 A1 | 3/2008 | Guimberteau et al. |
| 2008/0069891 A1 | 3/2008 | Habib et al. |
| 2008/0075771 A1 | 3/2008 | Vaughn et al. |
| 2008/0102121 A1 | 5/2008 | Devane et al. |
| 2008/0113025 A1 | 5/2008 | Devane et al. |
| 2008/0152595 A1 | 6/2008 | Emigh et al. |
| 2008/0166407 A1 | 7/2008 | Shalaby et al. |
| 2008/0193540 A1 | 8/2008 | Soula et al. |
| 2008/0200493 A1 | 8/2008 | Drewes et al. |
| 2008/0234352 A1 | 9/2008 | Fischer et al. |
| 2008/0247959 A1 | 10/2008 | Bartholomaus et al. |
| 2008/0248110 A1 | 10/2008 | Pettersson et al. |
| 2008/0248113 A1 | 10/2008 | Bartholomaus et al. |
| 2008/0254122 A1 | 10/2008 | Fischer et al. |
| 2008/0254123 A1 | 10/2008 | Fischer et al. |
| 2008/0254124 A1 | 10/2008 | Bar-Shalom |
| 2008/0268057 A1 | 10/2008 | Andersen et al. |
| 2008/0299199 A1 | 12/2008 | Bar-Shalom et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0022790 A1 | 1/2009 | Flath et al. |
| 2009/0022798 A1 | 1/2009 | Rosenberg et al. |
| 2009/0041838 A1 | 2/2009 | Guimberteau et al. |
| 2009/0081290 A1 | 3/2009 | McKenna et al. |
| 2009/0099151 A1 | 4/2009 | Jain et al. |
| 2009/0155357 A1 | 6/2009 | Muhuri |
| 2009/0169631 A1 | 7/2009 | Zamloot et al. |
| 2009/0202634 A1 | 8/2009 | Jans et al. |
| 2009/0274759 A1 | 11/2009 | Bar-Shalom et al. |
| 2009/0298862 A1 | 12/2009 | Yum et al. |
| 2009/0317355 A1 | 12/2009 | Roth et al. |
| 2010/0099696 A1 | 4/2010 | Soscia et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Andersen et al. |
| 2010/0204259 A1 | 8/2010 | Tygesen et al. |
| 2010/0266701 A1 | 10/2010 | Guimberteau et al. |
| 2010/0291205 A1 | 11/2010 | Downie et al. |
| 2011/0008424 A1 | 1/2011 | Chang et al. |
| 2011/0020451 A1 | 1/2011 | Bartholomaus et al. |
| 2011/0038930 A1 | 2/2011 | Barnscheid et al. |
| 2011/0077238 A1 | 3/2011 | Leech et al. |
| 2011/0104214 A1 | 5/2011 | Oshlack et al. |
| 2011/0136847 A1 | 6/2011 | Chan et al. |
| 2011/0142905 A1 | 6/2011 | Naelappa et al. |
| 2011/0159100 A1 | 6/2011 | Andersen et al. |
| 2011/0195989 A1 | 8/2011 | Rudnic et al. |
| 2011/0200681 A1 | 8/2011 | Habib et al. |
| 2011/0200715 A1 | 8/2011 | Fuisz et al. |
| 2011/0229526 A1 | 9/2011 | Rosenberg et al. |
| 2011/0229533 A1 | 9/2011 | Edgren et al. |
| 2011/0287093 A1 | 11/2011 | Schoenhard |
| 2012/0009129 A1 | 1/2012 | Brzeczko |
| 2012/0015007 A1 | 1/2012 | Bredenberg et al. |
| 2012/0059065 A1 | 3/2012 | Barnscheid et al. |
| 2012/0065220 A1 | 3/2012 | Barnscheid et al. |
| 2012/0135075 A1 | 5/2012 | Mohammad |
| 2012/0136021 A1 | 5/2012 | Barnscheid et al. |
| 2012/0164220 A1 | 6/2012 | Huang |
| 2012/0201761 A1 | 8/2012 | Sackler |
| 2012/0202838 A1 | 8/2012 | Ghosh et al. |
| 2012/0202839 A1 | 8/2012 | Emigh et al. |
| 2012/0214777 A1 | 8/2012 | Crowley et al. |
| 2012/0225122 A1 | 9/2012 | Hamed et al. |
| 2012/0251637 A1 | 10/2012 | Bartholomaus et al. |
| 2012/0321674 A1 | 12/2012 | Vachon et al. |
| 2012/0321713 A1 | 12/2012 | Han et al. |
| 2012/0321716 A1 | 12/2012 | Vachon et al. |
| 2013/0005823 A1 | 1/2013 | Emigh et al. |
| 2013/0011479 A1 | 1/2013 | Angeli et al. |
| 2013/0012533 A1 | 1/2013 | Oshlack et al. |
| 2013/0022646 A1 | 1/2013 | Rudnic et al. |
| 2013/0028177 A1 | 1/2013 | Koskela et al. |
| 2013/0028970 A1 | 1/2013 | Schwier et al. |

(56) References Cited

U.S. PATENT DOCUMENTS

| | | |
|---|---|---|
| 2013/0028972 A1 | 1/2013 | Schwier et al. |
| 2013/0030561 A1 | 1/2013 | Imanari et al. |
| 2013/0084333 A1 | 4/2013 | Dick et al. |
| 2013/0090349 A1 | 4/2013 | Geibler et al. |
| 2013/0122087 A1 | 5/2013 | Habib et al. |
| 2013/0122101 A1 | 5/2013 | Habib et al. |
| 2013/0129825 A1 | 5/2013 | Billoet et al. |
| 2013/0129826 A1 | 5/2013 | Geibler et al. |
| 2013/0171075 A1 | 7/2013 | Arkenau-Maric et al. |
| 2013/0171257 A1 | 7/2013 | Kumar et al. |
| 2013/0195981 A1 | 8/2013 | Pettersson |
| 2013/0195982 A1 | 8/2013 | Pettersson |
| 2013/0209557 A1 | 8/2013 | Barnscheid |
| 2013/0209560 A1 | 8/2013 | Hamed et al. |
| 2013/0217716 A1 | 8/2013 | Wright et al. |
| 2013/0225697 A1 | 8/2013 | Barnscheid et al. |
| 2013/0230596 A1 | 9/2013 | Mehta |
| 2013/0245055 A1 | 9/2013 | Wright et al. |
| 2013/0251759 A1 | 9/2013 | Jans et al. |
| 2013/0251796 A1 | 9/2013 | McKenna et al. |
| 2013/0251798 A1 | 9/2013 | McKenna et al. |
| 2013/0251799 A1 | 9/2013 | McKenna et al. |
| 2013/0251801 A1 | 9/2013 | McKenna et al. |
| 2013/0251802 A1 | 9/2013 | McKenna et al. |
| 2013/0251806 A1 | 9/2013 | Andrade de Freitas et al. |
| 2013/0259939 A1 | 10/2013 | McKenna et al. |
| 2013/0259940 A1 | 10/2013 | McKenna et al. |
| 2013/0260015 A1 | 10/2013 | McKenna et al. |
| 2013/0261143 A1 | 10/2013 | Wright et al. |
| 2013/0273162 A1 | 10/2013 | Li et al. |
| 2013/0280176 A1 | 10/2013 | Diezi et al. |
| 2013/0280338 A1 | 10/2013 | Wening et al. |
| 2013/0281480 A1 | 10/2013 | Yum et al. |
| 2013/0287845 A1 | 10/2013 | Yum et al. |
| 2013/0287849 A1 | 10/2013 | Andersen et al. |
| 2013/0295168 A1 | 11/2013 | Yum et al. |
| 2013/0303494 A1 | 11/2013 | Wright et al. |
| 2013/0303623 A1 | 11/2013 | Barnscheid et al. |
| 2013/0317049 A1 | 11/2013 | Yum et al. |
| 2013/0317051 A1 | 11/2013 | Oshlack et al. |
| 2013/0320592 A1 | 12/2013 | Arkenau-Maric et al. |
| 2013/0337059 A1 | 12/2013 | Yum et al. |
| 2013/0337060 A1 | 12/2013 | Yum et al. |
| 2013/0344142 A1 | 12/2013 | Rahmouni et al. |
| 2013/0344143 A1 | 12/2013 | Rosenberg et al. |
| 2014/0004191 A1 | 1/2014 | Rahmouni et al. |
| 2014/0030327 A1 | 1/2014 | McKenna et al. |
| 2014/0120164 A1 | 5/2014 | Fischer et al. |
| 2014/0155388 A1 | 6/2014 | Brzeczko et al. |
| 2014/0193490 A1 | 7/2014 | Schoenhard |
| 2014/0220126 A1 | 8/2014 | Tygesen et al. |
| 2014/0221416 A1 | 8/2014 | Guido et al. |
| 2014/0271848 A1 | 9/2014 | Guido et al. |
| 2014/0271849 A1 | 9/2014 | Shmeis et al. |
| 2014/0271896 A1 | 9/2014 | Shmeis et al. |
| 2014/0275143 A1 | 9/2014 | Devarakonda et al. |
| 2014/0294947 A1 | 10/2014 | Reilly et al. |
| 2014/0356426 A1 | 12/2014 | Barnscheid et al. |
| 2014/0356428 A1 | 12/2014 | Barnscheid et al. |
| 2015/0024048 A1 | 1/2015 | Hemmingsen et al. |
| 2015/0037417 A1 | 2/2015 | Fischer et al. |

FOREIGN PATENT DOCUMENTS

| | | |
|---|---|---|
| EP | 0406315 | 11/1992 |
| EP | 0 908 181 | 4/1999 |
| EP | 1 027 888 | 8/2000 |
| EP | 0 335 560 | 1/2002 |
| EP | 1213014 | 6/2002 |
| EP | 1 371 360 | 5/2005 |
| GB | 1430684 | 3/1976 |
| GB | 2170104 | 7/1986 |
| GB | 2182559 | 5/1987 |
| JP | 60/255719 | 12/1985 |
| JP | 07/100191 | 4/1995 |
| WO | WO 86/04817 | 8/1986 |
| WO | WO 89/09066 | 10/1989 |
| WO | WO 90/08536 | 8/1990 |
| WO | WO 91/04015 | 4/1991 |
| WO | WO 92/09270 | 6/1992 |
| WO | WO 93/10765 | 6/1993 |
| WO | WO 95/22962 | 8/1995 |
| WO | WO 96/00066 A1 | 1/1996 |
| WO | WO 96/08253 A1 | 3/1996 |
| WO | WO 97/33566 A2 | 9/1997 |
| WO | WO 99/05105 | 2/1999 |
| WO | WO 99/44591 A1 | 9/1999 |
| WO | WO 99/51208 | 10/1999 |
| WO | WO 00/41704 | 7/2000 |
| WO | WO 01/35958 | 5/2001 |
| WO | WO 01/51035 | 7/2001 |
| WO | WO 01/51036 | 7/2001 |
| WO | WO 01/74357 | 10/2001 |
| WO | WO 02/056861 A2 | 7/2002 |
| WO | WO 02/065834 | 8/2002 |
| WO | WO 02/087512 A1 | 11/2002 |
| WO | WO 02/092078 | 11/2002 |
| WO | WO 03/026613 | 4/2003 |
| WO | WO 03/039521 | 5/2003 |
| WO | WO 2003/075897 | 9/2003 |
| WO | WO 03/082204 | 10/2003 |
| WO | WO 03/092648 A1 | 11/2003 |
| WO | WO 03/101384 A2 | 12/2003 |
| WO | WO 2004/002447 A2 | 1/2004 |
| WO | WO 2004/047839 A1 | 6/2004 |
| WO | WO 2004/054542 A2 | 7/2004 |
| WO | WO 2004/056337 A2 | 7/2004 |
| WO | WO 2004/091512 A2 | 10/2004 |
| WO | WO 2004/093819 | 11/2004 |
| WO | WO 2004/093843 | 11/2004 |
| WO | WO 2005/000310 A1 | 1/2005 |
| WO | WO 2005/007074 | 1/2005 |
| WO | WO 2005/016313 | 2/2005 |
| WO | WO 2005/016314 A1 | 2/2005 |
| WO | WO 2005/027878 | 3/2005 |
| WO | WO 2005/034859 A2 | 4/2005 |
| WO | WO 2005/053587 A1 | 6/2005 |
| WO | WO 2005/063206 A1 | 7/2005 |
| WO | WO 2005/063214 A1 | 7/2005 |
| WO | WO 2005/102286 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/026504 | 3/2006 |
| WO | WO 2006/030402 A2 | 3/2006 |
| WO | WO 2006/031209 A1 | 3/2006 |
| WO | WO 2006/058249 A2 | 6/2006 |
| WO | WO 2006/088305 A1 | 8/2006 |
| WO | WO 2006/089843 A2 | 8/2006 |
| WO | WO 2006/103418 A1 | 10/2006 |
| WO | WO 2006/103551 | 10/2006 |
| WO | WO 2006/106344 | 10/2006 |
| WO | WO 2007/014061 A2 | 2/2007 |
| WO | WO 2007/030754 A2 | 3/2007 |
| WO | WO 2007/053698 | 5/2007 |
| WO | WO 2007/082757 A2 | 7/2007 |
| WO | WO 2007/085024 A2 | 7/2007 |
| WO | WO 2007/106550 A2 | 9/2007 |
| WO | WO 2007/112285 A2 | 10/2007 |
| WO | WO 2007/112286 A2 | 10/2007 |
| WO | WO 2007/133583 A2 | 11/2007 |
| WO | WO 2007/135193 A2 | 11/2007 |
| WO | WO 2007/150074 A2 | 12/2007 |
| WO | WO 2007/150075 A2 | 12/2007 |
| WO | WO 2008/023261 | 2/2008 |
| WO | WO 2008/023261 A1 | 2/2008 |
| WO | WO 2008/027442 A2 | 3/2008 |
| WO | WO 2008/028047 A2 | 3/2008 |
| WO | WO 2008/033523 A1 | 3/2008 |
| WO | WO 2008/068471 A1 | 6/2008 |
| WO | WO 2008/100375 A2 | 8/2008 |
| WO | WO 2008/107149 A2 | 9/2008 |
| WO | WO 2009/035474 A1 | 3/2009 |

(56) References Cited

FOREIGN PATENT DOCUMENTS

| WO | WO 2009/075782 A1 | 6/2009 |
|---|---|---|
| WO | WO 2009/076236 A2 | 6/2009 |
| WO | WO 2009/076764 A1 | 6/2009 |
| WO | WO 2009/088414 A2 | 7/2009 |
| WO | WO 2009/092601 A1 | 7/2009 |
| WO | WO 2009/104838 A1 | 8/2009 |
| WO | WO 2009/114648 A1 | 9/2009 |
| WO | WO 2010/017821 A1 | 2/2010 |
| WO | WO 2010/032128 | 3/2010 |
| WO | WO 2010/032128 A1 | 3/2010 |
| WO | WO 2010/066034 A1 | 6/2010 |
| WO | WO 2010/069050 A1 | 6/2010 |
| WO | WO 2010/083894 A1 | 7/2010 |
| WO | WO 2010/140007 A2 | 12/2010 |
| WO | WO 2010/151741 A1 | 12/2010 |
| WO | WO 2011/009602 A1 | 1/2011 |
| WO | WO 2011/009603 A1 | 1/2011 |
| WO | WO 2011/009604 A1 | 1/2011 |
| WO | WO 2011/041414 A1 | 4/2011 |
| WO | WO 2011/068723 A1 | 6/2011 |
| WO | WO 2011/079248 A1 | 6/2011 |
| WO | WO 2011/106416 A2 | 9/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/040651 A1 | 3/2012 |
| WO | WO 2012/061779 A1 | 5/2012 |
| WO | WO 2012/076907 A2 | 6/2012 |
| WO | WO 2012/080833 A2 | 6/2012 |
| WO | WO 2012/085656 A2 | 6/2012 |
| WO | WO 2012/085657 A2 | 6/2012 |
| WO | WO 2012/112952 A1 | 8/2012 |
| WO | WO 2012/131463 A2 | 10/2012 |
| WO | WO 2013/017234 A1 | 2/2013 |
| WO | WO 2013/017242 A1 | 2/2013 |
| WO | WO 2013/030177 | 3/2013 |
| WO | WO 2013/038267 A1 | 3/2013 |
| WO | WO 2013/038268 A1 | 3/2013 |
| WO | WO 2013/050539 A2 | 4/2013 |
| WO | WO 2013/057570 A2 | 4/2013 |
| WO | WO 2013/072395 A1 | 5/2013 |
| WO | WO 2013/077851 A1 | 5/2013 |
| WO | WO 2013/084059 A1 | 6/2013 |
| WO | WO 2013/128276 A2 | 9/2013 |
| WO | WO 2013/171146 | 11/2013 |
| WO | WO 2014/091437 | 6/2014 |

OTHER PUBLICATIONS

Miyazaki et al., "In situ-gelling gellan formulations as vehicles for oral drug delivery," *J. Control Release*, vol. 60, pp. 287-295 (1999).

Rowe et al., "Glycerin," *Handbook of Pharmaceutical Excipients*, Pharmaceutical Presse, 4$^{th}$ edition, pp. 257-258 (2003).

Yamakita et al., "In Vitro/In Vivo Evaluation of Two Series of TA5707F Controlled Release Matrix Tablets Prepared with Hydroxypropyl Methyl Cellulose Derivates with Entero-Soluble or Gel-Formation Properties," *Biol. Pharm. Bull*, vol. 18, No. 10, pp. 1409-1416 (1995).

Marvola et al., "Enteric polymers as binders and coating materials in multiple-unit site-specific drug delivery systems," *European Journal of Pharmaceutical Sciences*, vol. 7, pp. 259-267, 1999.

Varshosaz et al., "Use of enteric polymers for production of microspheres by extrusion-spheronization," *Pharmaceutica Acta Helvetiae*, vol. 72, pp. 145-152. 1997.

Wanka et al., "Phase Diagrams and Aggregation Behavior of Poly(oxyethylene)-Poly(oxypropylene)-Poly(oxyethylene) Triblock Copolymers in Aqueous Solutions," vol. 27, pp. 4145-4159, 1994.

Katikaneni et al., "Ethylcellulose matrix controlled release tablets of a water-soluble drug," International Journal of Pharmaceutics, vol. 123, pp. 119-125, 1995.

Polysciences, Inc., "Monomers & Polymers," http://www.polysciences.com/Catalog/Department/Product/98/categoryid-298/productid--422/, published Apr. 3, 2004.

Brannan et al., "Affine Geometry," Geometry, 2$^{nd}$ ed., p. 78, 2012.

Camu et al., "Pharmacology of systemic analgesics," Best Practice & Research Clinical Anaesthesiology, vol. 16, No. 4, pp. 475-488, 2002.

Dahlstrom et al., "Patient-controlled Analgesic Therapy, Part IV: Pharmacokinetics and Analgesic Plasma Concentration of Morphine," Clinical Pharmacokinetics, vol. 7, pp. 266-279, 1982.

Graves et al., "Relationship between plasma morphine concentrations and pharmacologic effects in postoperative patients using patient-controlled analgesia," Clinical Pharmacy, vol. 4, pp. 41-47, Jan.-Feb. 1985.

Hemmingson et al., "Drug Abuse Resistant, Controlled Release, Using Egalet Dosage Units," poster, published Jun. 28, 2007.

Raehal et al., "Mu Opioid 'Receptor' Regulation and Opiate Responsiveness," The AAPS Journal, vol. 7, No. 3, pp. E587-E591, 2005.

Qui et al., "Design of a core-shelled polymer cylinder for potential programmable drug delivery," International Journal of Pharmaceutics, vol. 219, pp. 151-160, 2001.

Haahr et al., "Drug abuse resistant, controlled release, using Egalet® dosage units," Proceedings of the 34$^{th}$ Annual Meeting Exposition of the Controlled Release Society, Poster, Jul. 7-11, 2007.

"MiraLAX®, MiraLAX® Drug Description," Oct. 19, 2011.

Fischer et al., "Nonmedical Use of Prescription Opioids: Furthering a Meaningful Research Agenda," The Journal of Pain, vol. 9, No. 6, pp. 490-493, Jun. 2008.

Meyer et al., "Awareness Topic: Mitigating the Risks of Ethanol Induced Dose Dumping from Oral Sustained/Controlled Release Dosage Forms," FDA's ACPS meeting, Oct. 2005.

National Institute on Drug Abuse, "Prescription Medications," http://www.nida.nih.gov/drugpages/prescription.html, accessed on Jul. 15, 2008.

National Institute on Drug Abuse, "Monitoring the Future: National Results on Adolescent Drug Use," http://www.samhsa.gov, May 2009.

Office Action issued on Dec. 1, 2011 in U.S. Appl. No. 12/701,248 (U.S. Pat. No. 9,005,660).

Office Action issued on Feb. 24, 2012 in U.S. Appl. No. 12/701,248 (U.S. Pat. No. 9,005,660).

Office Action issued on Jul. 20, 2012 in U.S. Appl. No. 12/701,248 (U.S. Pat. No. 9,005,660).

Notice of Allowance issued on Aug. 19, 2014 in U.S. Appl. No. 12/701,248 (U.S. Pat. No. 9,005,660).

Notice of Allowance issued on Jan. 23, 2015 in U.S. Appl. No. 12/701,248 (U.S. Pat. No. 9,005,660).

Office Action issued on Sep. 10, 2015 in U.S. Appl. No. 14/446,234 (US 2015/0024048).

Office Action issued on Jul. 29, 2015 U.S. Appl. No. 14/496,561 (US 2015/0079150).

Office Action issued on Oct. 29, 2015 in U.S. Appl. No. 14/331,833 (US 2015/0037417).

Krögel et al., "Pulsatile Drug Release from an Insoluble Capsule Body Controlled by an Erodible Plug," Pharmaceutical Research, vol. 15, No. 3, pp. 474-481, 1998.

IMMEDIATE RELEASE COMPOSITION RESISTANT TO ABUSE BY INTAKE OF ALCOHOL

FIELD OF THE INVENTION

The present invention provides a pharmaceutical composition for oral administration that are resistant to abuse by intake of alcohol. The pharmaceutical compositions are in the form of matrix compositions or coated matrix compositions, wherein the matrix compositions comprise one or more low molecular weight polyglycols combined with one or more effervescent agents. The pharmaceutical compositions have a relatively high hardness due to the ingredients and the manufacturing method.

The pharmaceutical compositions may also contain a disintegrant.

The pharmaceutical compositions are typically prepared by injection moulding or heat extrusion but can also be in form of compressed tablets.

BACKGROUND OF THE INVENTION

In recent years, a tendency has emerged among people, especially young people, to increase the effect of alcohol and/or specific drug substances by intake of for example pain relievers or fever reducers in combination with alcohol. Many pharmaceutical compositions for oral use release the drug substance with a faster release rate in the presence of alcohol and, accordingly, the drug substance is available for absorption at a faster rate than intended by the manufacturer. Such a faster release rate may lead to unwanted and potentially dangerous effects. This may lead to unwanted effects similar to the effect denoted "dose dumping".

Unintended, rapid drug release in a short period of time of the entire amount or a significant fraction of the drug substance retained in a controlled release dosage form is often referred to as "dose dumping". It has been reported that some modified-release oral dosage forms contain drug substances and excipients that exhibit higher solubility in ethanolic solutions compared to aqueous media. Such products can be expected to exhibit a more rapid drug dissolution and release rate in the presence of ethanol. Therefore, in theory, concomitant consumption of alcoholic beverages along with these products might be expected to have the potential to induce dose dumping (FDA's ACPS Meeting 2005). However, the problem is not only of relevance for controlled release dosage form, but also for conventional oral dosage forms and for immediate release dosage forms.

Moreover, in the 1990s, Food and Drug Administrations in USA (FDA) announced that for example over-the-counter (OTC) pain relievers and fever reducers must carry a warning label advising consumers who consume three or more alcoholic drinks every day to consult a physician before using these drugs. FDA issued this final rule after considering public comments and data on the effect of combining chronic alcohol ingestion and the use of various OTC analgesics. The action also followed the recommendations of the Nonprescription Drugs Advisory Committee and the Arthritis Drugs Advisory Committee which concluded that chronic alcohol users should be warned that they may be at an increased risk of liver damage or stomach bleeding from use of these drugs. Relevant drug substances are for example aspirin, other salicylates, acetaminophen, ibuprofen, naproxen sodium, or ketoprofen.

A number of controlled release pharmaceutical compositions have been developed that are said to be resistant towards abuse by intake of alcohol. However, there is still a need for developing pharmaceutical compositions with immediate release of a drug substance (analgesics, antipyretics etc.) that also are resistant to abuse by intake of alcohol.

FIGURES

FIG. 1. PEG 3350S without disintegrant or effervescence. Dissolution-profiles % release versus time in minutes (n=3) in HCl solution-buffer (pH 1.2) and 40% (v/v) alcohol/pH 1.2.

Figure 2:
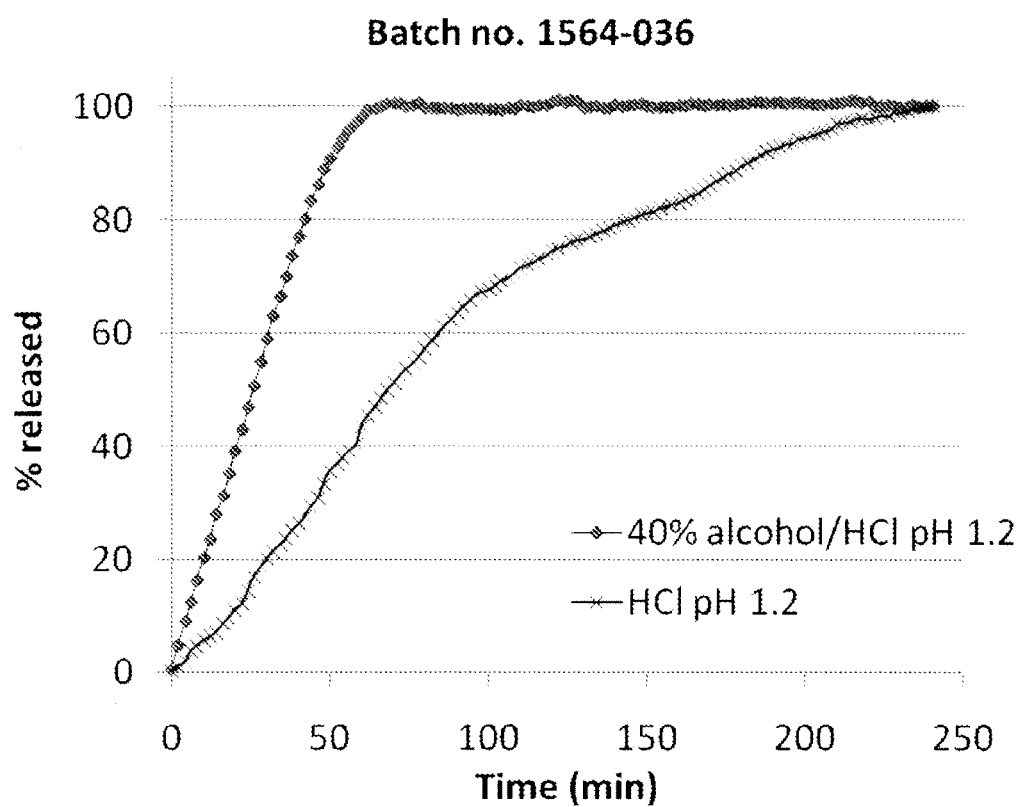

FIG. 2. PEG 6000 without disintegrant or effervescence. Dissolution-profiles % release versus time in minutes (n=3) in HCl solution (pH 1.2) and 40% (v/v) alcohol/pH 1.2.

Figure 3:
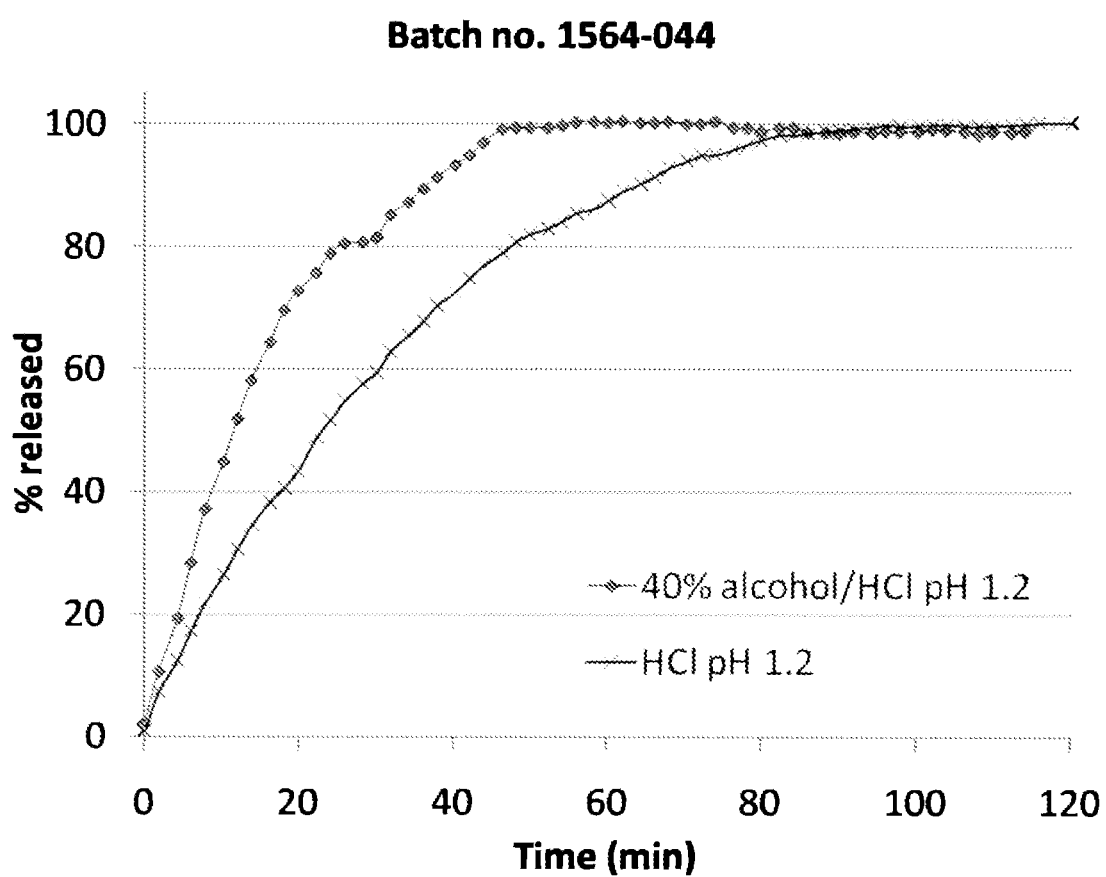

FIG. 3. PEG 17,000 without disintegrant or effervescence. Dissolution-profiles % release versus time in minutes (n=3) in HCl solution (pH 1.2) and 40% (v/v) alcohol/pH 1.2.

Figure 4:
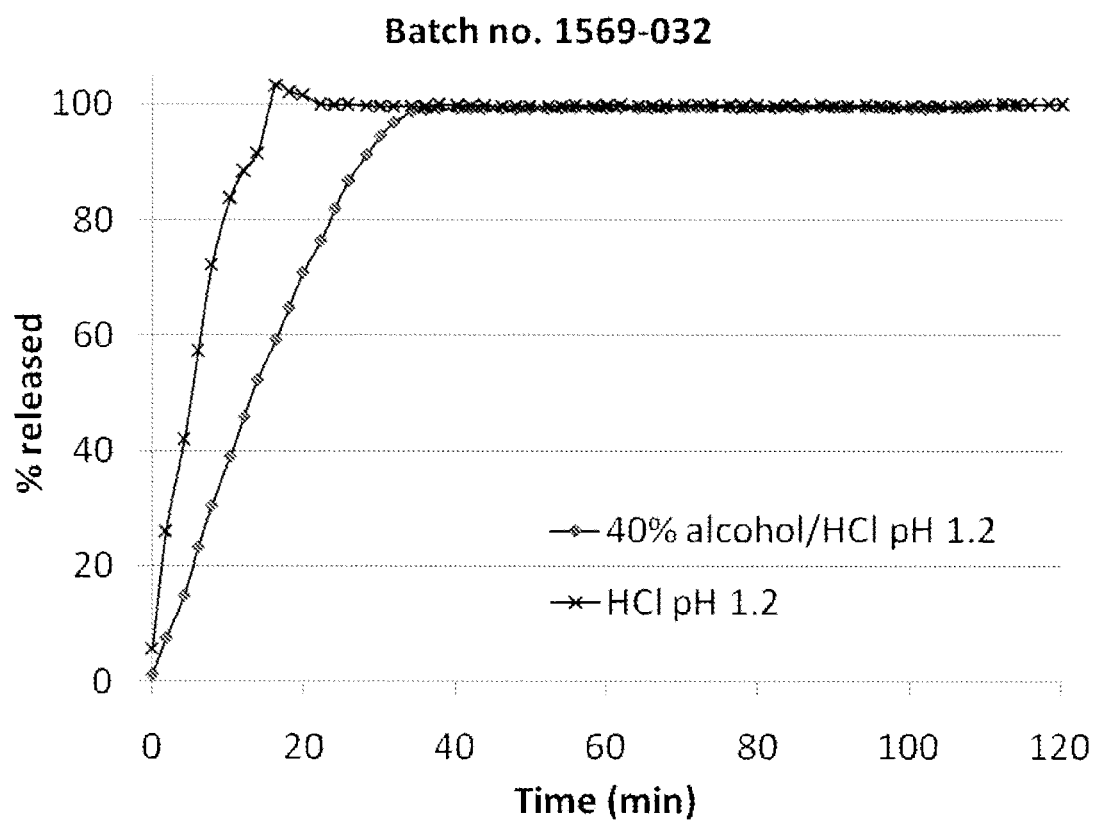

FIG. 4. PEG 3350 with a combination of 2% w/w citric acid and 5% w/w $NaHCO_3$ as effervescent agent. Dissolution-profiles % release versus time in minutes (n=3) in HCl solution (pH 1.2) and 40% (v/v) alcohol/pH 1.2.

Figure 5:
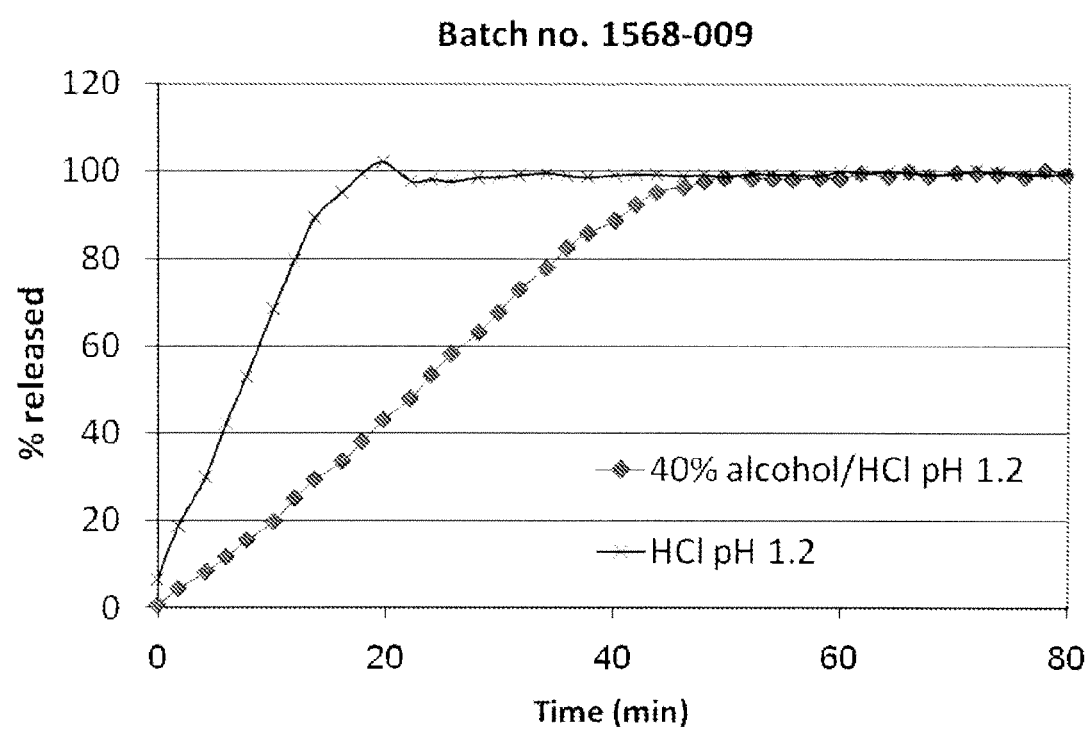

FIG. 5. PEG 6000 with a combination of 2% w/w citric acid and 5% w/w $NaHCO_3$ as effervescent agent. Dissolution-profiles % release versus time in minutes (n=3) in HCl solution (pH 1.2) and 40% (v/v) alcohol/pH 1.2.

Figure 6:
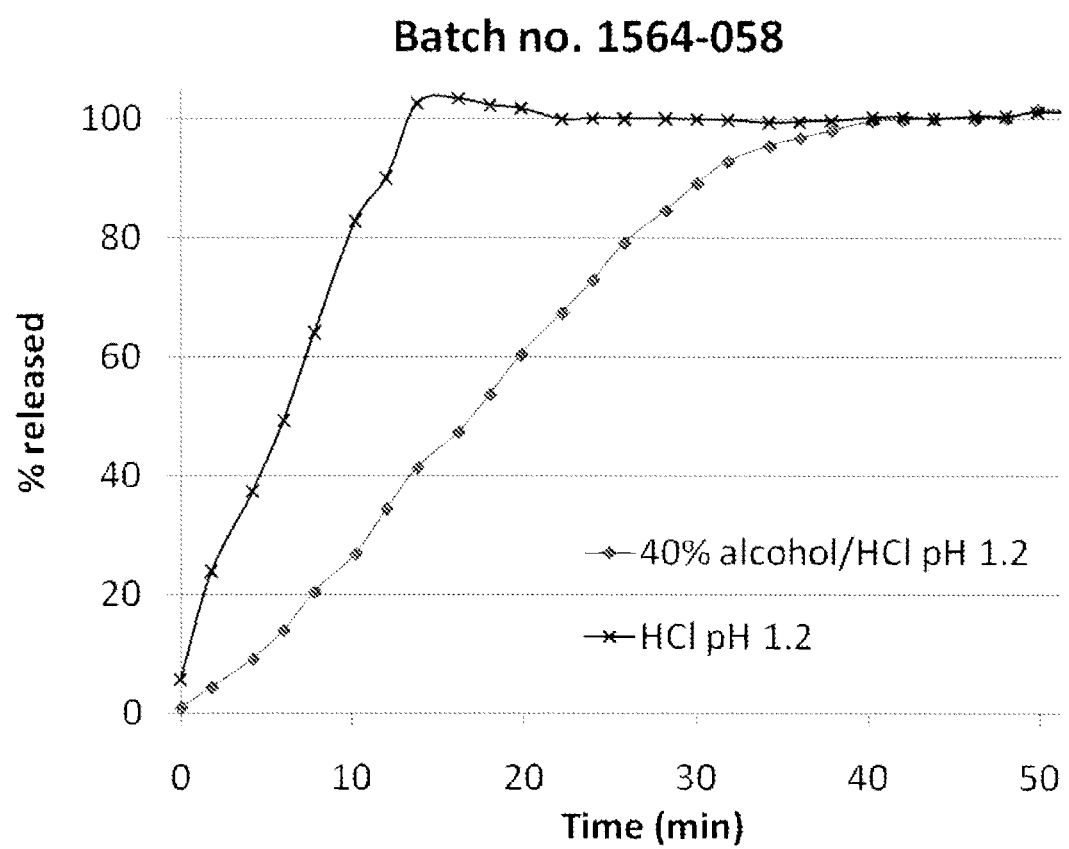

FIG. 6. PEG 17,000 with a combination of 4% w/w citric acid and 10% w/w $NaHCO_3$ as effervescent agent. Dissolution-profiles % release versus time in minutes (n=3) in HCl solution (pH 1.2) and 40% (v/v) alcohol/pH 1.2.

Figure 7:
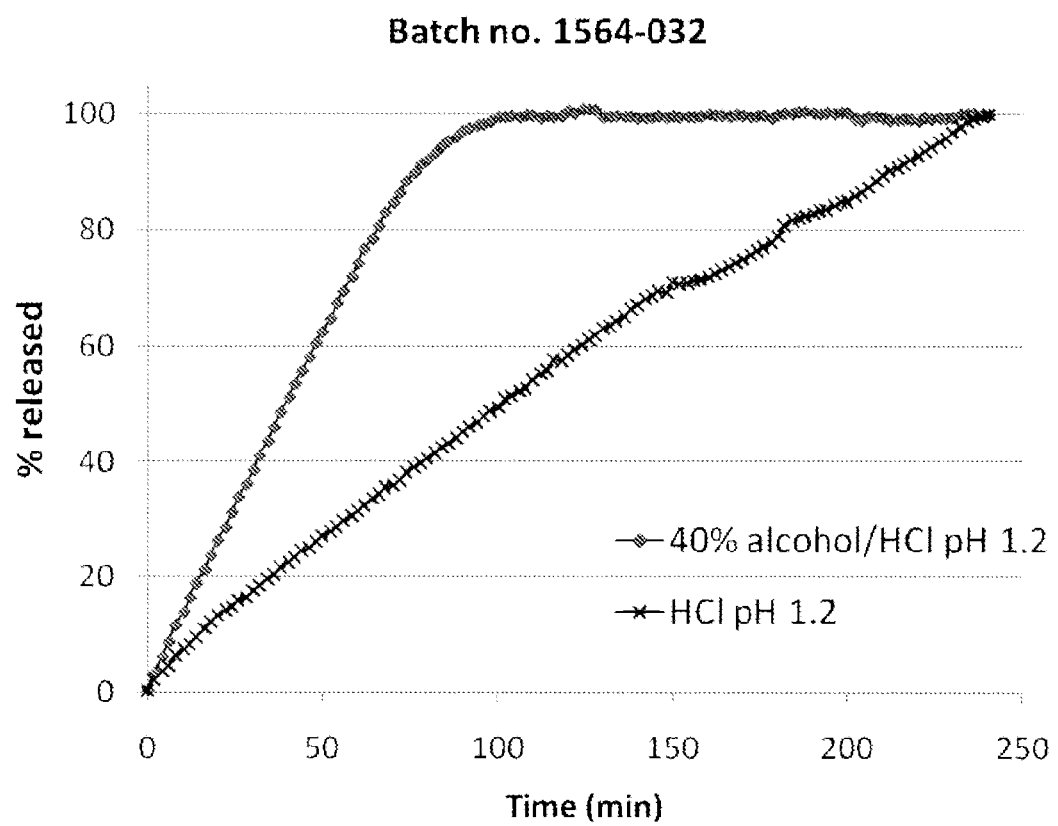

FIG. 7. PEG 6000 with 10% w/w Cross-caramellose Na as disintegrant. Dissolution-profiles % release versus time in minutes (n=3) in HCl solution (pH 1.2) and 40% (v/v) alcohol/pH 1.2.

Figure 8:
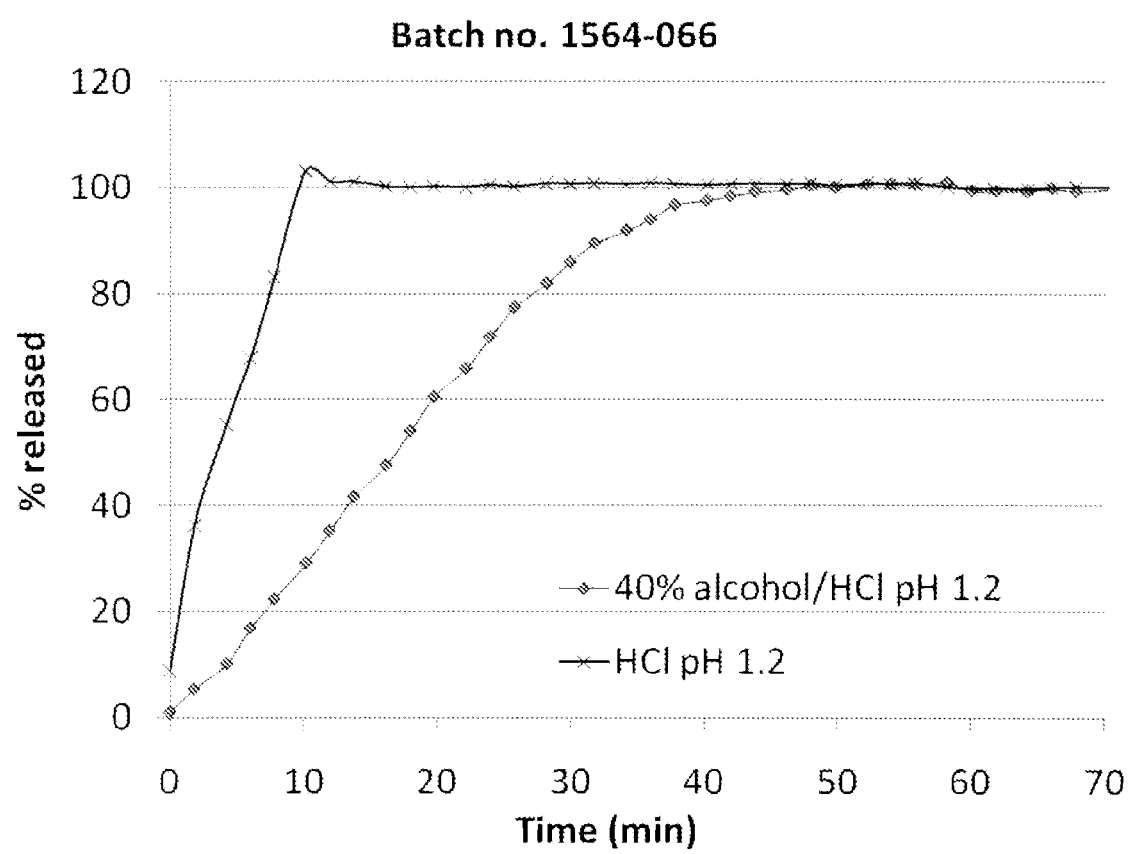

FIG. 8. PEG 17,000 with a combination of 4% w/w citric acid and 10% w/w $NaHCO_3$ as effervescent agent and 5% w/w Cross-caramellose Na as disintegrant. Dissolution-profiles % release versus time in minutes (n=3) in HCl solution (pH 1.2) and 40% (v/v) alcohol/pH 1.2.

Figure 9:
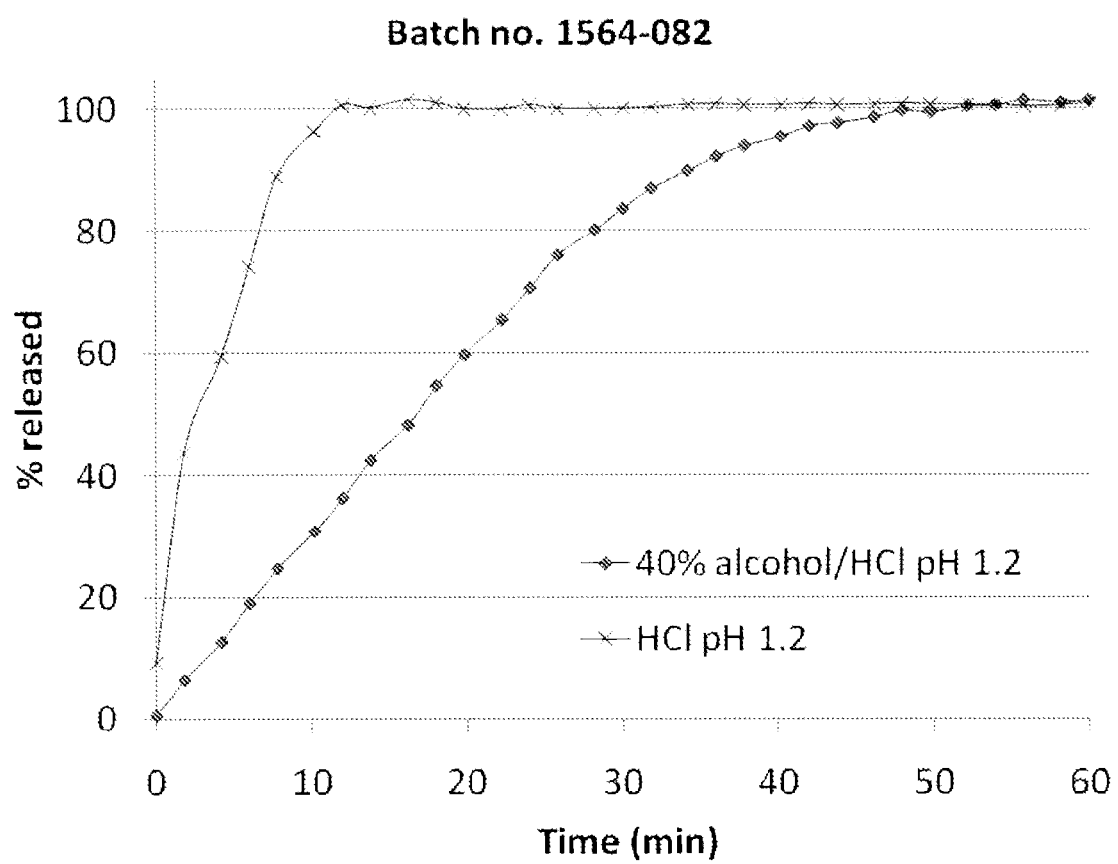

FIG. 9. PEG 14,000 with a combination of 3% w/w citric acid and 7.5% w/w $NaHCO_3$ as effervescent agent and 12.5% w/w Cross-caramellose Na as disintegrant. Dissolution-profiles % release versus time in minutes (n=3) in HCl solution (pH 1.2) and 40% (v/v) alcohol/pH 1.2.

Figure 10:
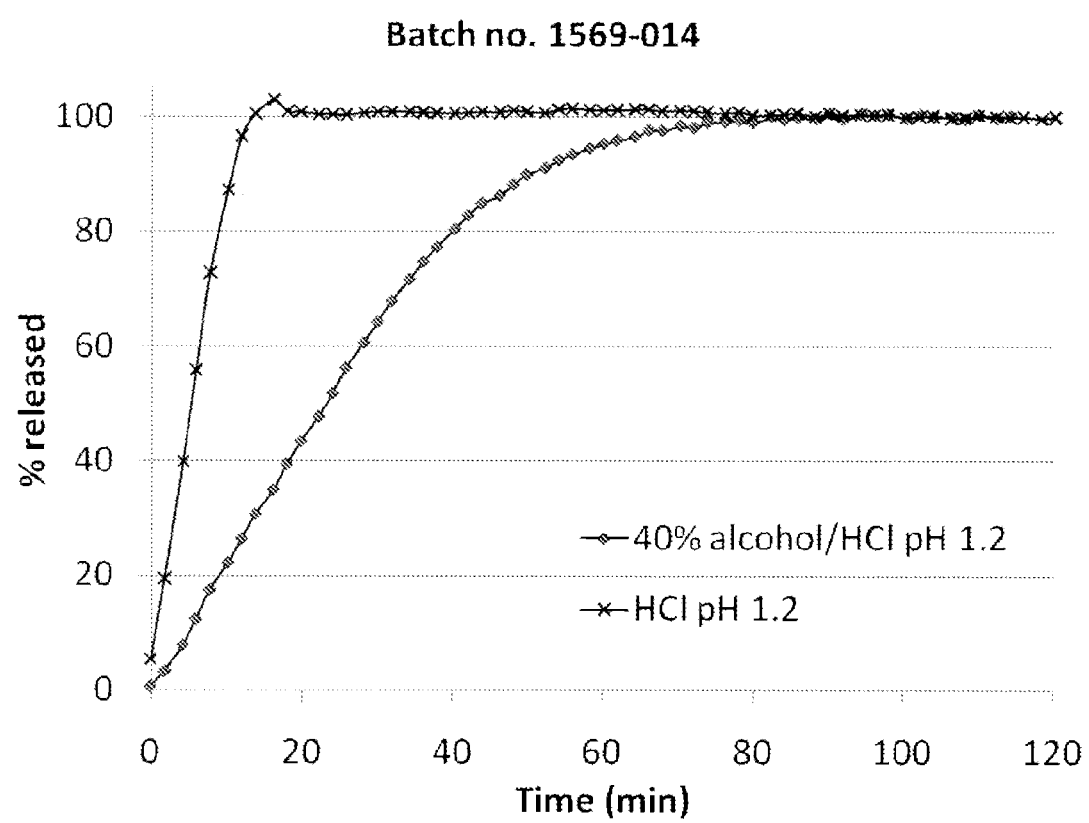

FIG. 10. PEG 10,000 with a combination of 2.5% w/w citric acid and 6.25% w/w $NaHCO_3$ as effervescent agent and 12.5% w/w Cross-caramellose Na as disintegrant. Dissolution-profiles % release versus time in minutes (n=3) in HCl solution (pH 1.2) and 40% (v/v) alcohol/pH 1.2.

Figure 11:
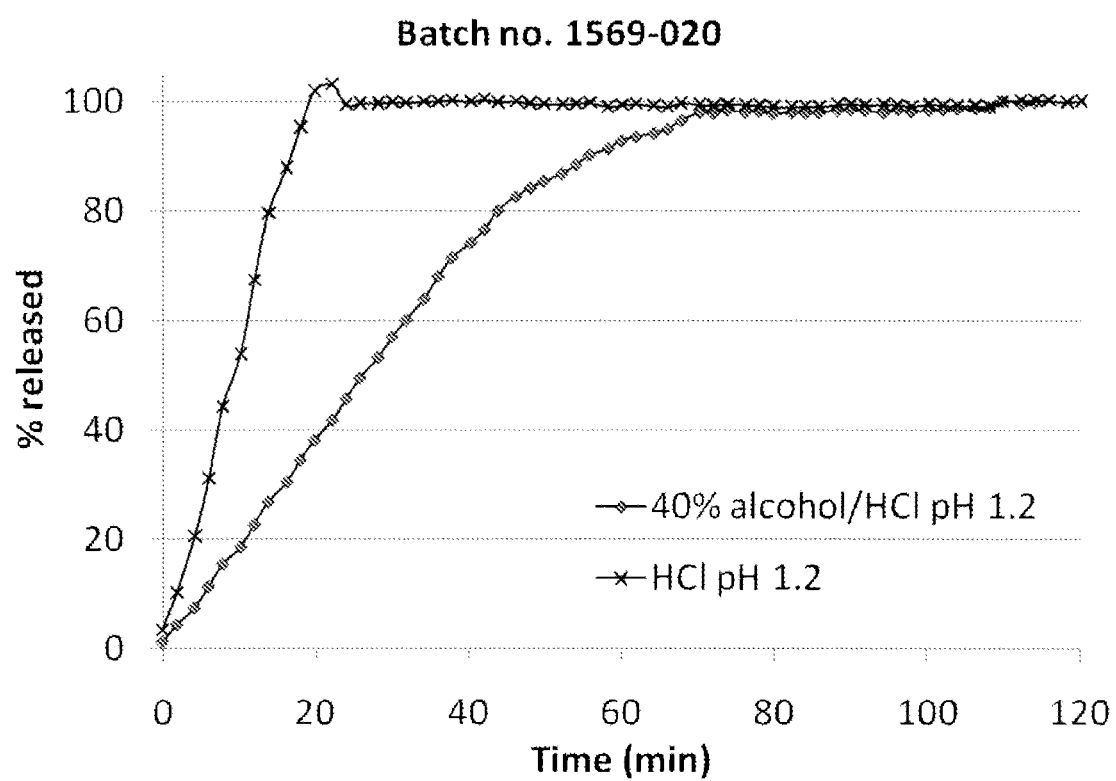

FIG. 11. PEG 6000 with a combination of 2% w/w citric acid and 5% w/w $NaHCO_3$ as effervescent agent and 12.5% w/w Cross-caramellose Na as disintegrant. Dissolution-profiles % release versus time in minutes (n=3) in HCl solution (pH 1.2) and 40% (v/v) alcohol/pH 1.2.

Figure 12:
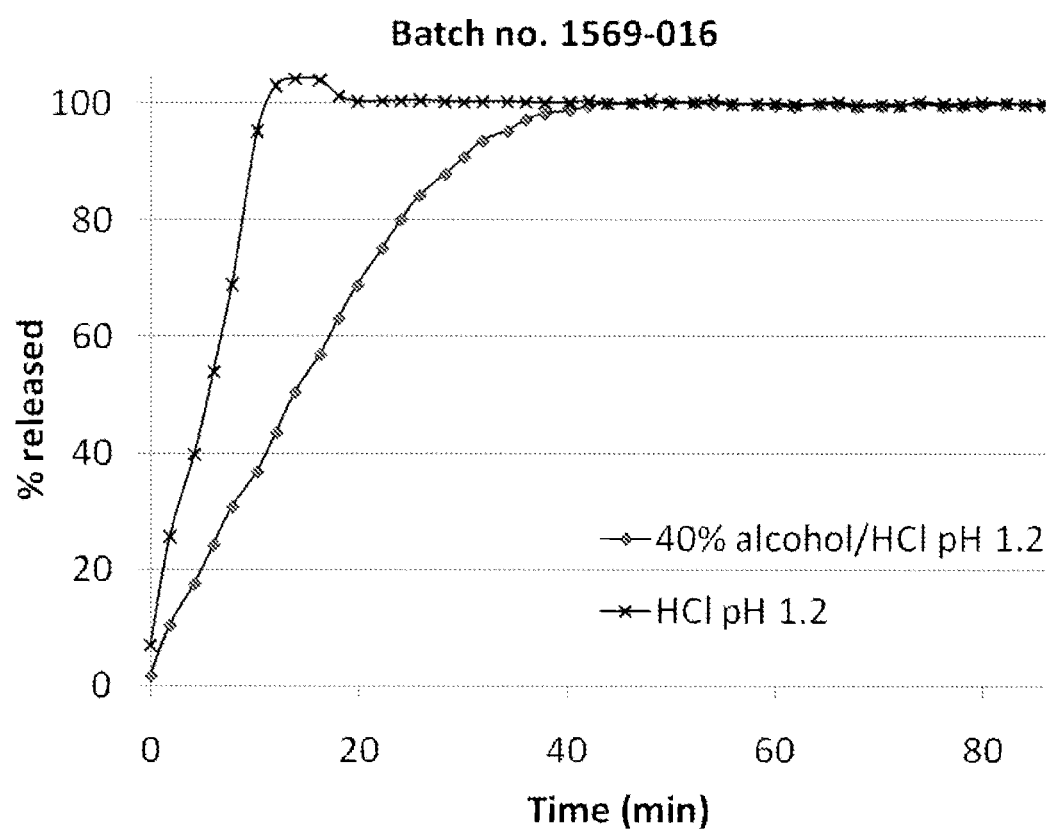

FIG. 12. PEG 3350 with a combination of 2% w/w citric acid and 5% w/w $NaHCO_3$ as effervescent agent and 12.5% w/w Cross-caramellose Na as disintegrant. Dissolution-profiles % release versus time in minutes (n=3) in HCl solution (pH 1.2) and 40% (v/v) alcohol/pH 1.2.

Figure 13:
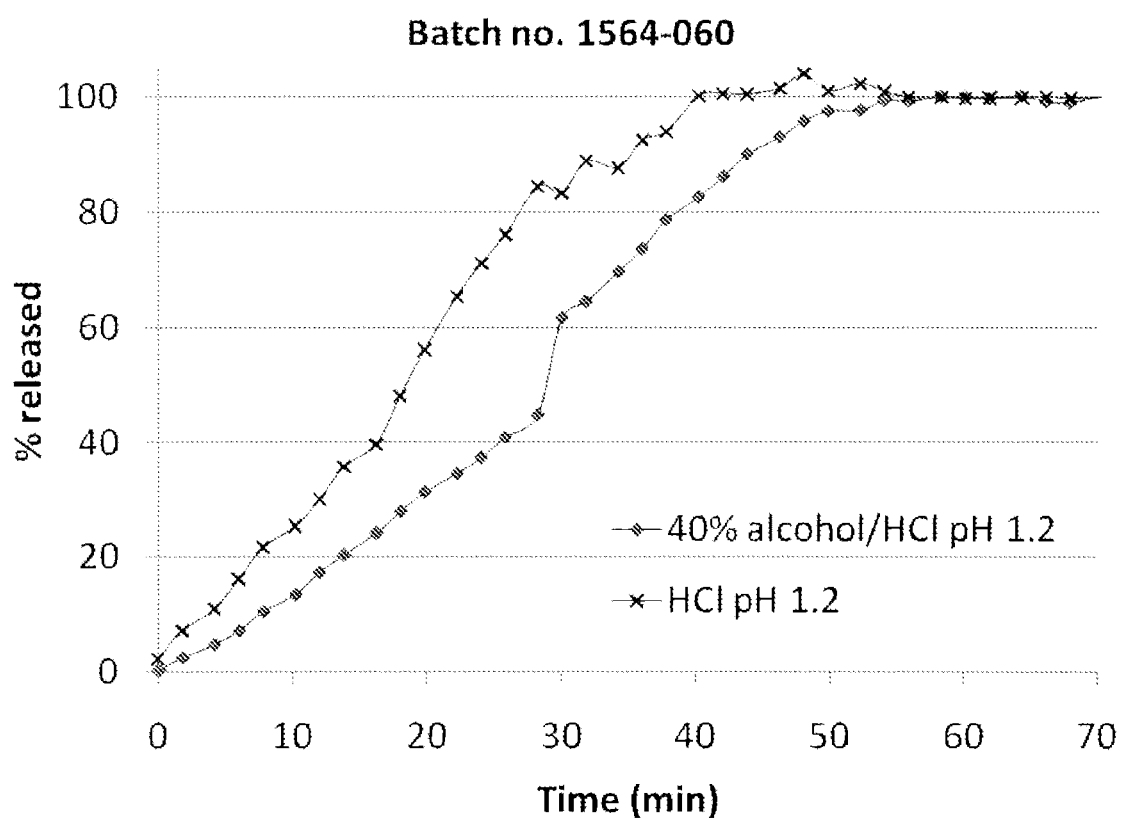

FIG. 13. PEG 6000 with a combination of 2% w/w tartaric acid and 5% w/w $NaHCO_3$ as effervescent agent. No disintegrant added. Dissolution-profiles % release versus time in minutes (n=3) in HCl solution (pH 1.2) and 40% (v/v) alcohol/pH 1.2.

Figure 14:
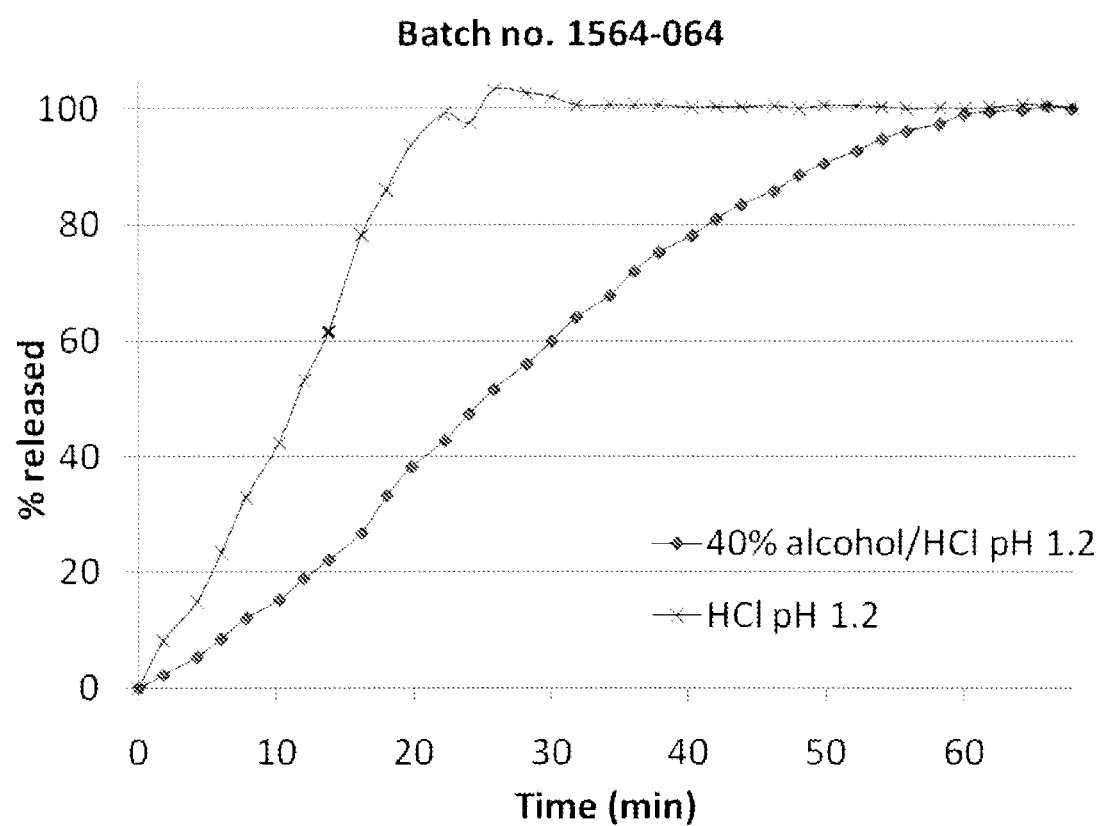

FIG. 14. PEG 6000 with a combination of added 4% w/w tartaric acid and 5% w/w $NaHCO_3$ as effervescent agent. No disintegrant added. Dissolution-profiles % release versus time in minutes (n=3) in HCl solution (pH 1.2) and 40% (v/v) alcohol/pH 1.2.

Figure 15:
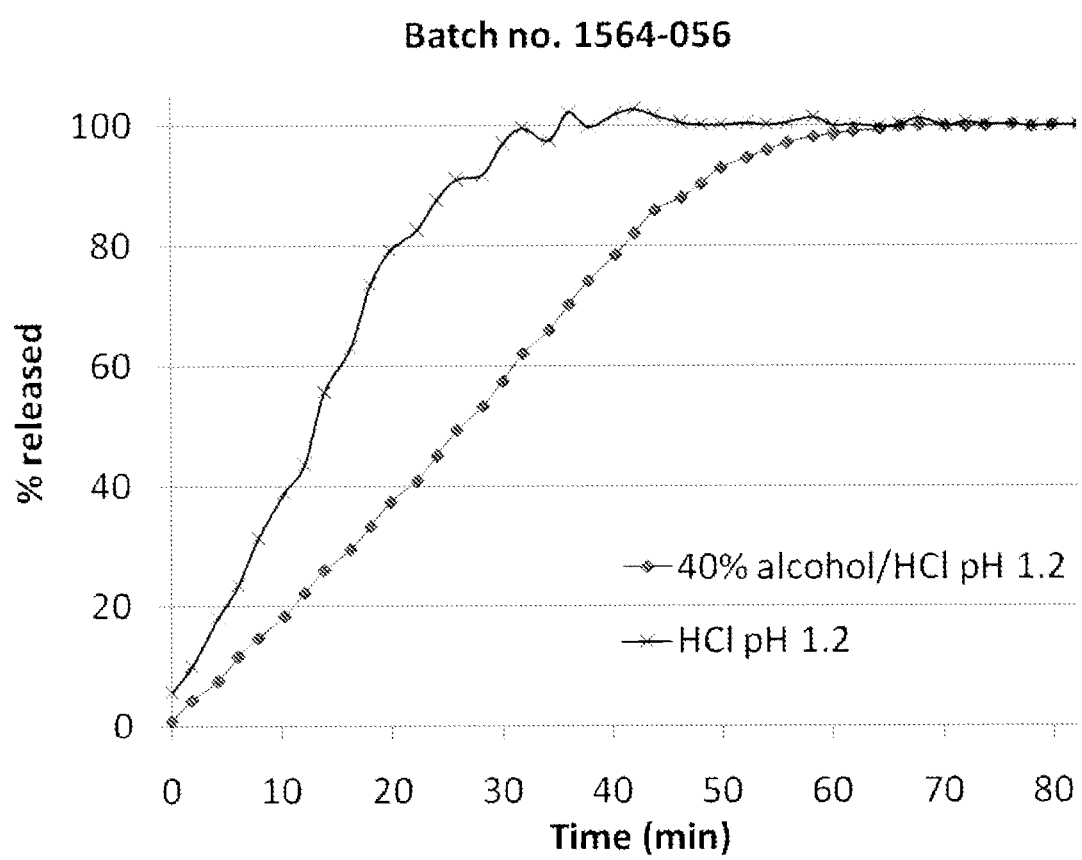

FIG. 15. PEG 6000 with a combination of added 2% w/w succinic acid and 5% w/w $NaHCO_3$ as effervescent agent. No disintegrant added. Dissolution-profiles % release versus time in minutes (n=3) in HCl solution (pH 1.2) and 40% (v/v) alcohol/pH 1.2.

Figure 16:
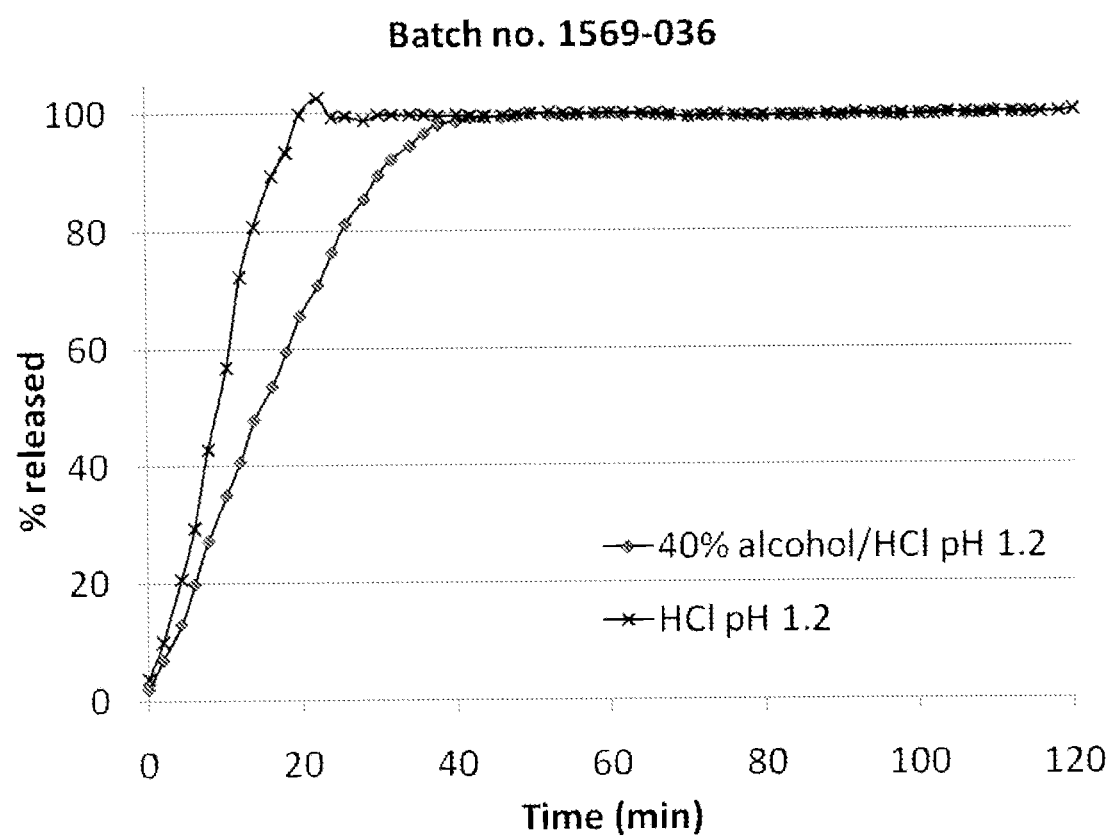

FIG. 16. PEG 6000 with a combination of added 4% w/w malonic acid and 5% w/w $NaHCO_3$ as effervescent agent. No disintegrant added. Dissolution-profiles % release versus time in minutes (n=3) in HCl solution (pH 1.2) and 40% (v/v) alcohol/pH 1.2.

Figure 17:
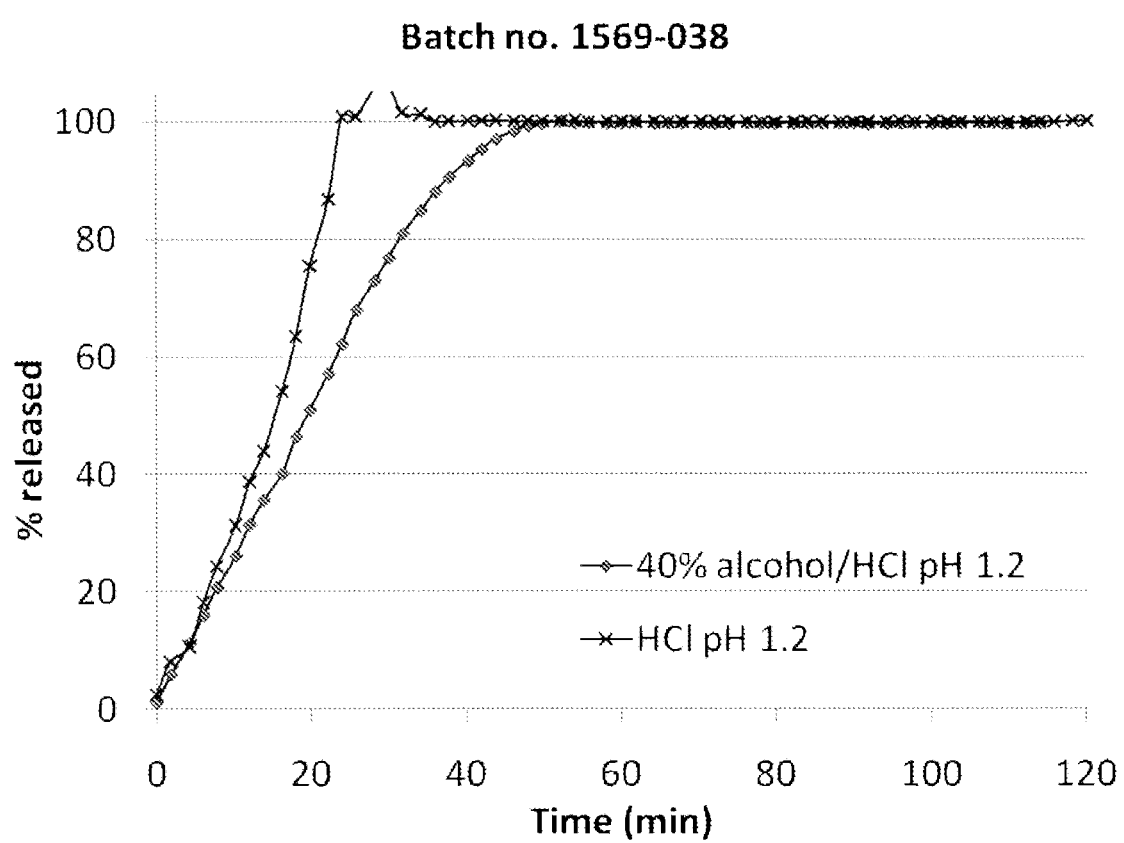

FIG. 17. PEG 6000 with a combination of added 4% w/w benzoic acid and 5% w/w $NaHCO_3$ as effervescent agent. No disintegrant added. Dissolution-profiles % release versus time in minutes (n=3) in HCl solution (pH 1.2) and 40% (v/v) alcohol/pH 1.2.

Figure 18:
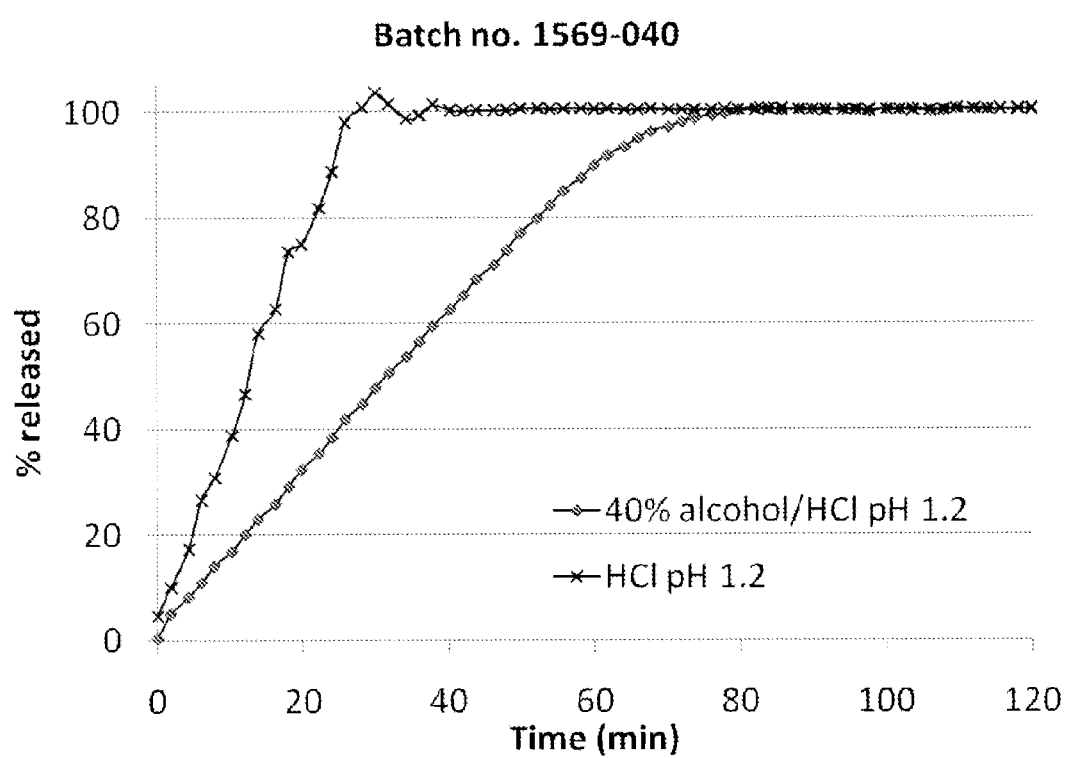

FIG. 18. PEG 6000 with a combination of added 4% w/w Oxalic acid and 5% w/w $NaHCO_3$ as effervescent agent. No disintegrant added. Dissolution-profiles % release versus time in minutes (n=3) in HCl solution (pH 1.2) and 40% (v/v) alcohol/pH 1.2.

Figure 19:
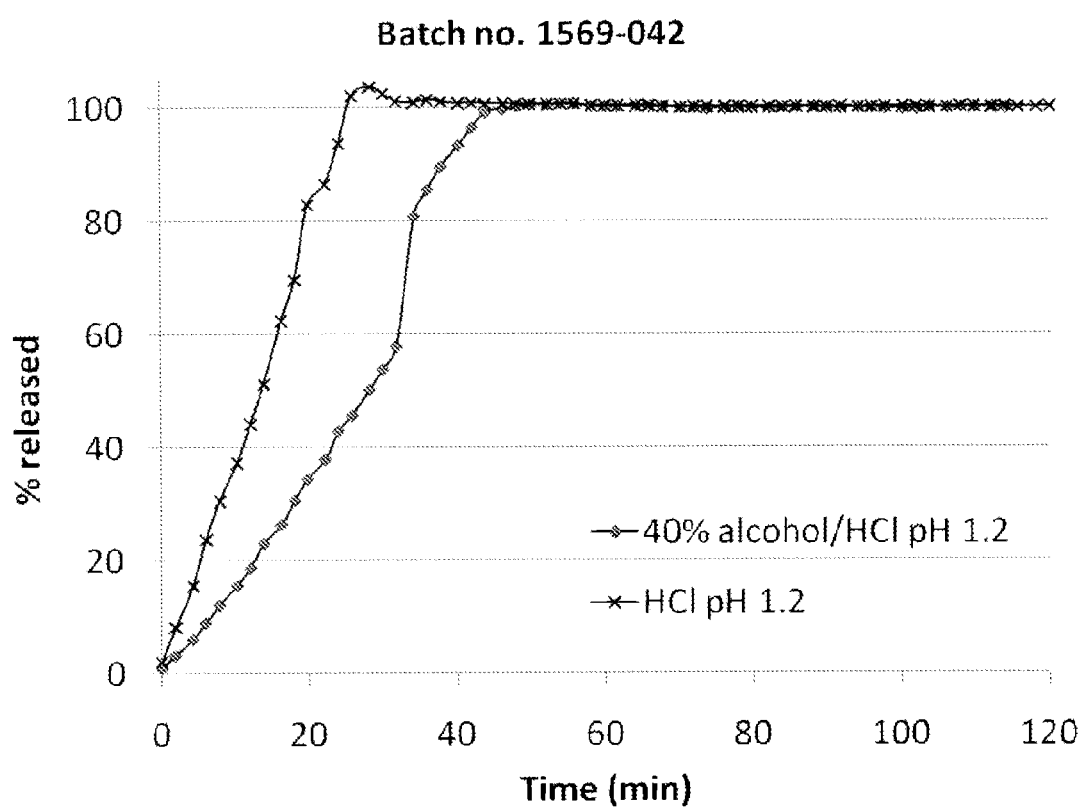

FIG. 19. PEG 6000 with a combination of added 4% w/w Malic acid and 5% w/w $NaHCO_3$ as effervescent agent. No disintegrant added. Dissolution-profiles % release versus time in minutes (n=3) in HCl solution (pH 1.2) and 40% (v/v) alcohol/pH 1.2.

Figure 20:
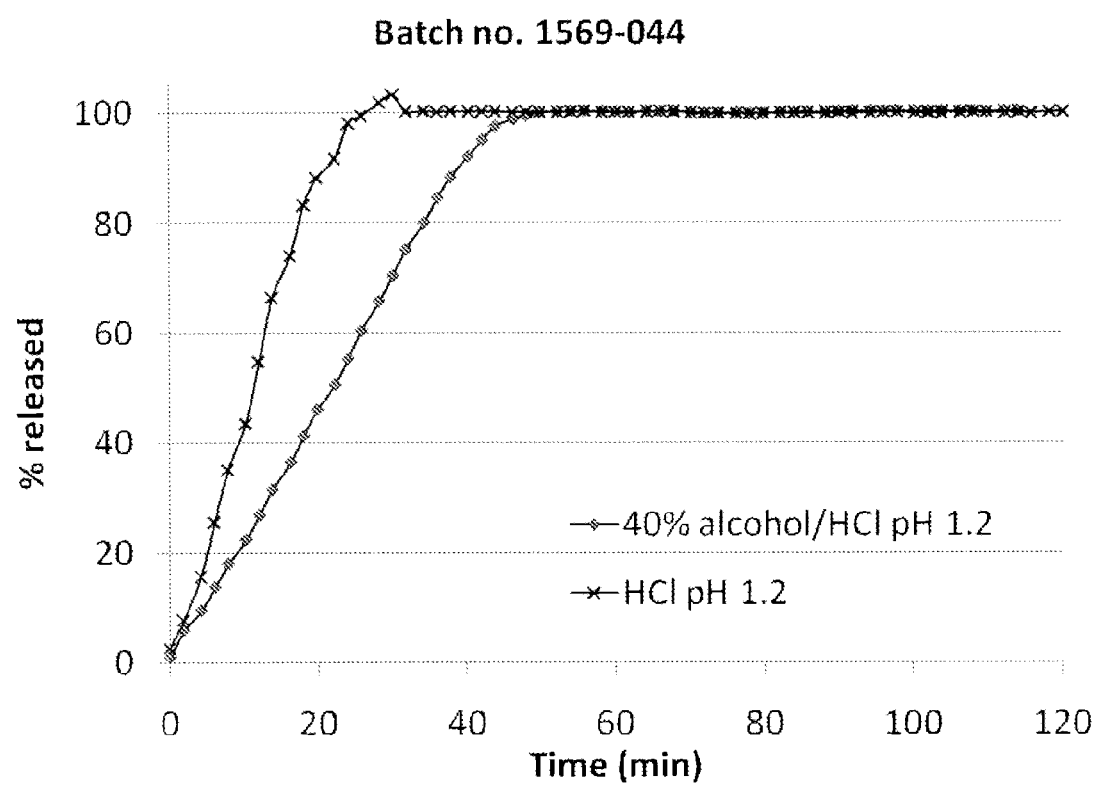

FIG. 20. PEG 6000 with a combination of added 4% w/w glutaric acid and 5% w/w $NaHCO_3$ as effervescent agent. No disintegrant added. Dissolution-profiles % release versus time in minutes (n=3) in HCl solution (pH 1.2) and 40% (v/v) alcohol/pH 1.2.

Figure 21:
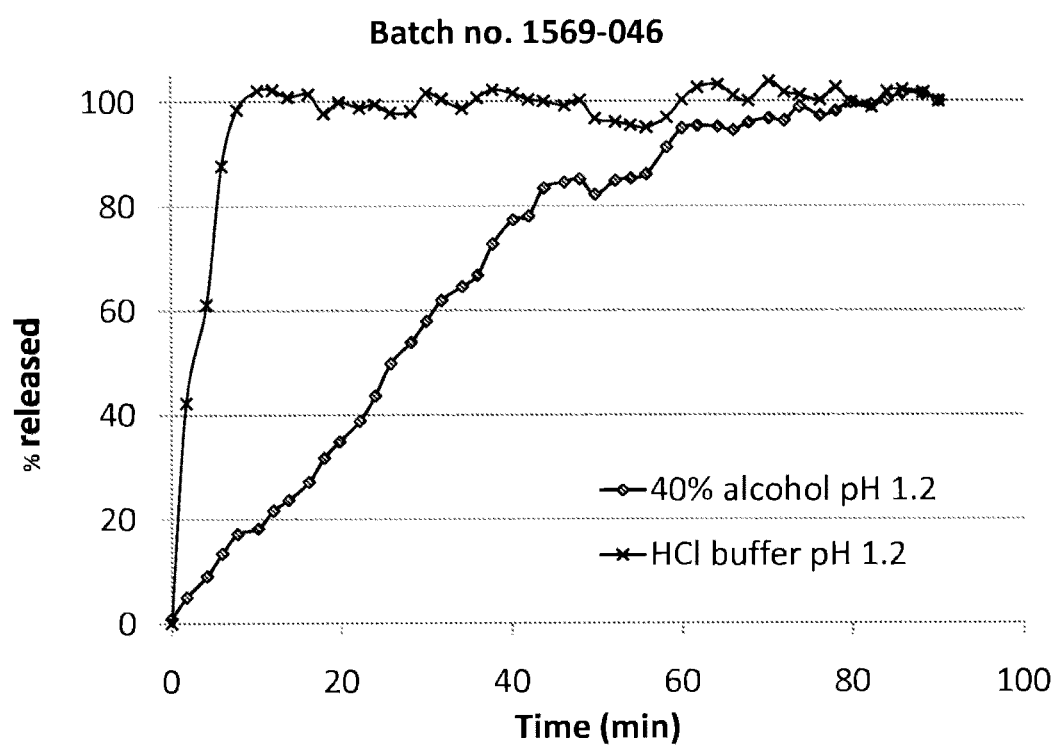

FIG. 21. PEG 6,000 with a combination of 2.5% w/w citric acid and 6.25% w/w $NaHCO_3$ as effervescent agent and 12.5% w/w Cross-caramellose Na as disintegrant. Dissolution-profiles % release versus time in minutes (n=3) in HCl solution (pH 1.2) and 40% (v/v) alcohol/pH 1.2.

Figure 22:
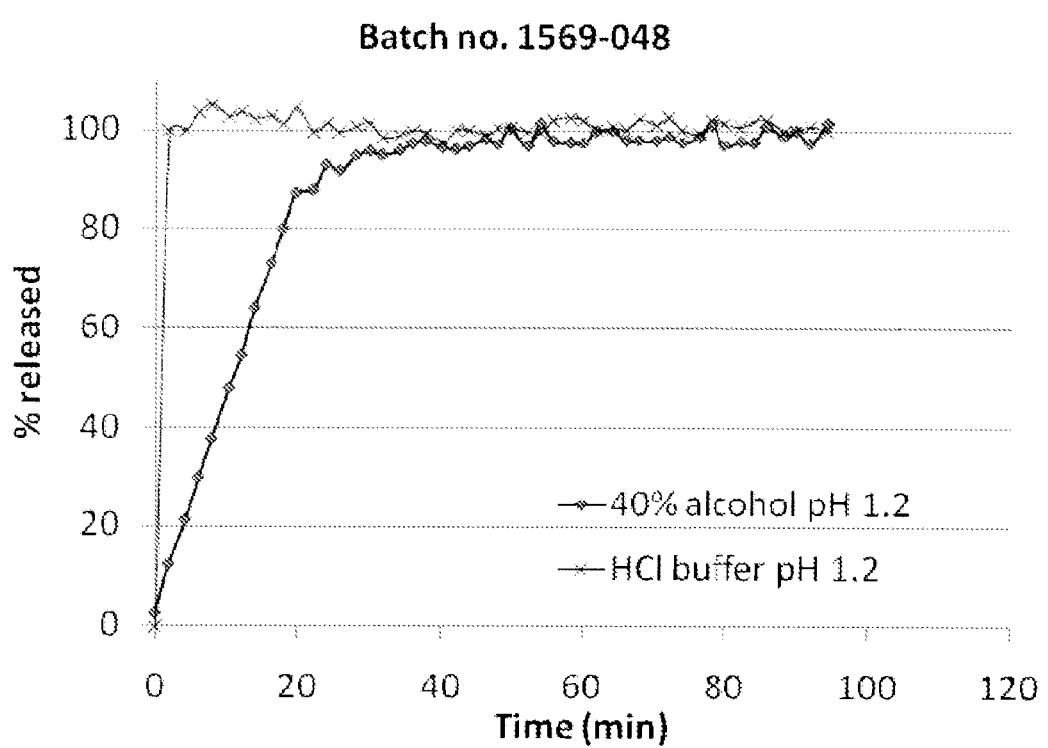

FIG. 22. PEG 6,000 with a combination of 6% w/w citric acid and 15% w/w $NaHCO_3$ as effervescent agent and 12.5% w/w Cross-caramellose Na as disintegrant. Dissolution-profiles % release versus time in minutes (n=3) in HCl solution (pH 1.2) and 40% (v/v) alcohol/pH 1.2.

Figure 23:
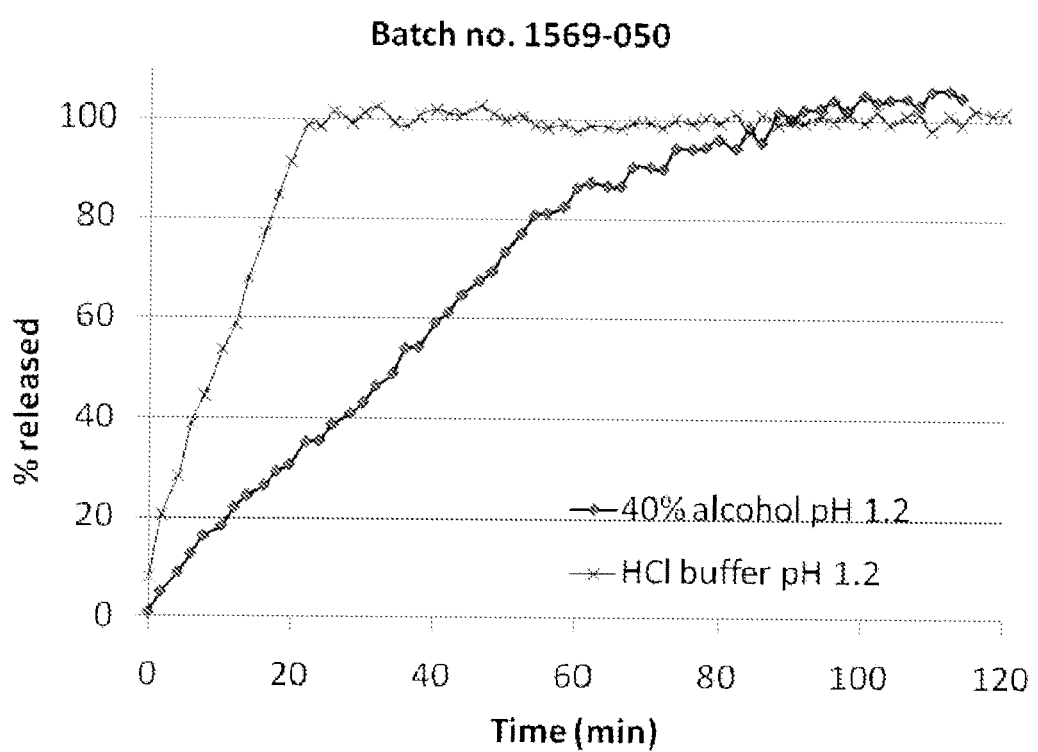

FIG. 23. PEG 17,000 with a combination of 2.5% w/w citric acid and 6.25% w/w $NaHCO_3$ as effervescent agent and 12.5% w/w Cross-caramellose Na as disintegrant. Dissolution-profiles % release versus time in minutes (n=3) in HCl solution (pH 1.2) and 40% (v/v) alcohol/pH 1.2.

DISCLOSURE OF THE INVENTION

The present invention provides immediate release compositions, wherein the release of the drug substance is decreased when the immediate release composition is tested in the in vitro dissolution test described herein using a dissolution medium containing 40% v/v ethanol compared with the release of the drug substance, when the immediate release composition is tested in the in vitro dissolution test described herein using the same dissolution medium, but without any content of ethanol.

Such immediate release compositions are obtained by using a polyglycol having a molecular weight of from 900 to 17,000 Daltons in a concentration of at least 5% w/w, one or more effervescent agents and optionally one or more disintegrants. The polyglycol and effervescent agent are both essential ingredients.

The present inventors have found that a suitable method for preparing such immediate release compositions are by means of injection moulding or heat extrusion but also by compression by using tabletting machines. Accordingly, the lower limit for suitable polyglycols is set by the melting point of the polyglycols, as the final immediate release composition should be in solid form, wherein the drug substance is dispersed in the matrix. It should be mentioned that the present applicant in several patents and patent applications (see for example WO 89/09066, WO 91/004015, WO 95/22962, WO 99/51208, WO 03/024429, WO 03/024426, WO 03/024430, WO 2004/041252, WO 2004/084869, WO 2004/084868, WO 2006/128471, WO 2008/086804, WO 2008/148798) has described the use of polyglycols with a molecular weight of from 20,000 and above for the preparation of a controlled release pharmaceutical composition.

In contrast thereto, the present invention provides ethanol-resistant immediate release compositions comprising a polyglycol having a molecular weight of from 900 to 17,000 Daltons in a concentration of 5% w/w or more, a drug substance, one or more effervescent agents and optionally one or more disintegrants for the preparation of an immediate release composition that is resistant to abuse by intake of alcohol.

In a specific embodiment, the present invention thus provides for the use of a polyglycol having a molecular weight of from 900 to 17,000 Daltons, a drug substance, one or more effervescent agents and optionally one or more disintegrants for the preparation of an immediate release composition that is resistant to abuse by intake of alcohol. In another embodiment, said immediate release composition is resistant to abuse by intake of alcohol when the composition is ingested with alcohol. In a further embodiment, said immediate release composition is formulated to exhibit a hardness that renders the composition resistant to crushing.

In an even further embodiment, the immediate release composition according to the present invention are resistant to abuse by intake of alcohol when said alcohol is ingested either:
  a. together with the immediate release composition, or
  b. within a period of up to 60 minutes before and up to 60 minutes after ingesting the immediate release composition.

In another embodiment, the invention provides a immediate release composition comprising a polyethylene glycol having a molecular weight of from 900 to 17,000 Daltons, one or more effervescent agents, optionally one or more disintegrants and one or more drug substances selected from anaesthetics, analgesics, opioids, antipyretics, antimigraine agents, antiepileptics, anti-parkinson agents, dopaminergic agents, antipsychotics, anxiolytics, sedatives, antidepressants, psychostimulating agents used for ADHD, nootropics and agents used in addictive disorders.

A immediate release composition according to the invention may also be used
  i) to prevent abuse of said drug substance, when the immediate release composition is ingested with alcohol,
  ii) to prevent dose dumping of said drug substance, when the immediate release composition is ingested with alcohol, and/or
  iii) to treat a patient suffering from a disease, disorder or condition to which the drug substance is therapeutically effective, wherein the patient ingests 3 or more alcoholic beverages daily. In particular embodiments, the patient to be treated ingests an alcoholic beverage either:
  a. together with the immediate release composition, or
  b. within a period of up to 60 minutes before and up to 60 minutes after ingesting the immediate release composition.

The present invention also provides for the use of a immediate release composition comprising a drug substance, a polyglycol having a molecular weight of from 900 to 17,000 Daltons, one or more effervescent agents and optionally one or more disintegrants to prevent abuse of said drug substance when the immediate release composition is ingested with alcohol. In a further embodiment, the invention provides for the use of an immediate release composition comprising a polyglycol having a molecular weight of from 900 to 17,000 Daltons, a drug substance, one or more effervescent agents and optionally one or more disintegrants to prevent dose dumping of said drug substance when the immediate release composition is ingested with alcohol.

Methods for preparing immediate release compositions resistant to abuse by intake of alcohol or by crushing are also provided herein.

The present invention also relates to a method for the preparation of an immediate release composition as defined above, the method comprising:
i) mixing a drug substance and a polyglycol having a molecular weight of from 900 to 17,000 Daltons with one or more effervescent agents and optionally one or more disintegrants,
ii) processing an injection moulding machine, an extruder or a tablet compression machine with the mixture obtained in step i)

According to the present invention, the drug substance is released from the immediate release composition in the stomach of a patient with a release profile that is dependent on the concentration of ethanol, such that an increased ethanol concentration results in a decreased rate of drug release.

Polymers

Suitable polymers for use according to the invention typically comprise a polyglycol, typically in the form of a homopolymer. In a specific embodiment the polymer is substantially water-soluble, thermoplastic, crystalline, semicrystalline or amorphous or a mixture of substantially water-soluble, crystalline, semi-crystalline or amorphous polymers. Suitable polymers for use in an immediate release composition according to the invention are polyethylene glycols, including derivatives such as mono- and dimethoxypolyethylene glycols (mPEGs) and polyethylene oxides. The immediate release compositions described herein may be prepared as matrix compositions formed using the polyglycol polymers described herein.

Polyethylene glycols (PEGs) are linear polydisperse polymers composed of repeating units of ethylene glycol. Their chemical formula is $HOCH_2[CH_2OCH_2]_mCH_2OH$ where m represents the average number of repeating units. Alternatively, the general formula $H[OCH_2CH_2]_nOH$ may be used to represent polyethylene glycol, where n is a number m in the previous formula+1. See the structural presentations of polyethylene glycol below. n is the average number of oxyethylene groups. n equals m+1.

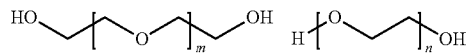

Polyethylene oxides (PEOs) are linear polydisperse nonionic polymers composed of repeating units of ethylene oxide. Their chemical formula is $HO[CH_2CH_2O]_nH$ where n represents the average number of oxyethylene groups. See the structural presentation of polyethylene oxide below. n is the average number of oxyethylene groups.

Depending on the preparation method, high molecular weight PEO may have one terminal methyl group.

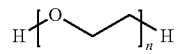

Polyethylene glycols are mixtures of addition of ethylene glycol. In general PEG refers to polymers chains with molecular weights below 20,000, while PEO refers to higher molecular weights polymers. However, because of the similarities between PEO and PEG, the terms are often used interchangeably for the same compound.

Polyethylene glycols and/or polyethylene oxides, which are suitable for use in the matrix compositions of the present invention, are those having molecular weights of from 900 Daltons, to 17,000 Daltons. Commercially available PEG/PEO's relevant for the present invention have the following average molecular weights: 1000, 1100, 1900, 2000, 2800, 2900, 3350, 4400, 5800, 6000, 8000, 8400, 10,000, 12,000, 14,600 or 17,000 Daltons.

In specific embodiments of the invention, an immediate release composition according to the present invention thus comprises a polyglycol having a molecular weight of 1000, 1100, 1900, 2000, 2800, 2900, 3350, 4400, 5800, 6000, 8000, 8400, 10,000, 12,000, 14,600 or 17,000 Daltons.

In one or more embodiments of the invention, the immediate release composition comprises a polyglycol selected from PEG 3350 S, PEG 6000, PEG 10 000, PEG 14 000 and PEG 17 000.

As described in patent applications/patent in the name of the Applicant (see above), PEG's/PEO's have been used in the preparation of coated matrix compositions with controlled release. However, in order to ensure controlled release, it is important to choose PEG's/PEO's with a relatively high molecular weight, i.e. 20,000 or more. Compositions of the present invention are in contrast hereto immediate release compositions, which the Applicant has found to function best using PEG's/PEO's having a molecular weight of from 900 to 17,000 Daltons.

Mixtures of PEO with different average molecular weights can be used in order to obtain a PEO with a desirable average molecular weight. The same applies to PEG.

The polymer has a melting point higher than the body temperature of the human in which the immediate release composition is to be used. Thus, the polymer(s) employed in the matrix composition will suitably have a melting point of between 30° C.-120° C. such as, for example from 35° C. to 100° C. or from 40° C. to 80° C.

In addition to a polymer of a polyglycol type as described above other polymers may be suitable for use in an immediate release composition provided that the solubility and/or release rate of the drug substance from the composition in aqueous media is higher than the solubility and/or release rate of the composition in an aqueous media containing 40% v/v ethanol as is tested in the in vitro dissolution test described herein using a aqueous media containing 40% v/v ethanol. More specifically, the solubility or release is at least 1.5 times higher, at least 2 times higher in aqueous media than in alcohol, notably 5 times, 10 times, 25 times, 50 times or 100 times higher. Thus, in other embodiments of the invention, the polymer or an additional polymer to the polyglycol may be selected from one or more of the following polymers: modified or unmodified water soluble natural polymers such as glucomannan, galactan, glucan, polygalacturonic acid, polyxylane, polygalactomannans, rhanogalacturonan, polyxyloglycan, arabinogalactan, and starch, cellulose, chitosan, alginate, fibrin, collagen, gelatin, hyaluronic acid, amylopectin, pectin including low methylated or methoxylated pectins, dextran and fatty acids and alcohols; synthetic polymers such as polyvinylpyrrolidone (PVP), PVA, PVB, Eudragit L methyl ester, Eudragit L, Eudragit RL, Eudragit E, Eudragit S, PHPV, PHA, PCL, PLGA and PLA; and hydrogels made from the polymers or combined polymers mentioned above and or from polymers originated from: HEMA, HEEMA, MEMA, MEEMA, EDGMA, NVP, VAc, AA, acrylamide, MAA, HPMA, PEGA, PEGMA, PEGDMA, PEGDA, and PEGDMA.

One or more polymers are typically present in an immediate release composition of the invention in a concentration amount of from 5% w/w to 99.9% w/w such as from 10% w/w to 95% w/w such as from 15% w/w to 90% w/w, such as from 20% w/w to 85% w/w, such as from 30% w/w to 85% w/w calculated as w/w % of the composition.

Disintegrants and Effervescent Agents

As mentioned above, an immediate release composition according to the invention comprises one or more effervescent agents and may comprise one or more disintegrants. In some situations (as mentioned above) it is important that the disintegrant and/or the effervescent agent are swellable or soluble in aqueous media and inswellable or insoluble in an aqueous dissolution medium containing 40% v/v of ethanol. Normally, with respect to disintegrants, disintegrants are high molecular weight materials, where it is more relevant to discuss the ability to swell than the solubility. Accordingly, for such substances it is important that they exert their disintegration properties in water or aqueous solutions, whereas the disintegration properties are eliminated or markedly reduced in aqueous solutions containing 40% v/v of ethanol. When solubility is important, the solubility in aqueous solutions containing 40% v/v of ethanol is at the most sparingly soluble, cf. the definitions below. The dissolution medium or aqueous medium is either a phosphate buffer medium pH 6.8 or hydrochloride solution pH 1.2.

Solubility definitions; Parts of solvent needed to dissolve 1 part of solute at ambient temperature—Very soluble <1; Freely soluble 1-10, Soluble 10-30; Sparingly soluble 30-100; Slightly soluble 100-1000; Very slightly soluble 1000-10,000, Insoluble >10,000.

The applicant has surprisingly found that a significant slower release rate in alcoholic media is noticed when a formulation according to the present invention based on PEG contains one or more effervescent agents alone or contains a particular combination of effervescent and disintegrant. This effect was not observed using a disintegrant alone. This behavior may have an in vivo effect, so that potential abusers would not achieve an enhancing effect when taking the tablet in combination with alcohol.

An immediate release composition having a time delay of at least 20 minutes for example at least 30 minutes, such as at least 40 minutes, for example such as at least 50 minutes and such as at least 60 minutes in alcohol (40% v/v of alcohol) has been developed. Alcohol generally enhances penetration of the epithelia by drug substances, but the time delay provided by immediate release compositions described herein may offset the increase in permeability normally associated by the presence of alcohol such that the desired in vivo effect of the immediate release composition is substantially maintained (for example, absorption rate of the drug from the immediate release composition is substantially maintained), even in the presence of alcohol.

The effervescent agent preferably is at least one component of an effervescent couple that includes an acid and a base. The effervescent couple is activated when contacted with water. The water liberates the acid and base and enables the acid and base to react with each other to produce carbon dioxide gas.

Examples of useful acids include water soluble organic acids. Further specific examples include citric acid, ascorbic acid, glutaric acid, malic acid, malonic acid, adipic acid, clavulanic acid, oxalic acid, tartaric acid, fumaric acid, succinic acid, sodium acid pyrophosphate, sorbic acid, sodium citrate dehydrate, lactic acid, hexamic acid, benzoic acid, etianic acids, disphosphonoic acids and acidic salts and acid anhydrides thereof, and mixtures thereof. Examples of useful acid anhydrides include citraconic anhydride, glucono-D-lactone, sulphuric acid, hyaluronic acid and succinic anhydride. Examples of useful acid salts include potassium bitartrate, acid citrate salts, sodium dihydrogen phosphate, disodium dihydrogen phosphate, and combinations thereof. The acid is present in the immediate release composition in an amount of from 1% by weight to 60% by weight or from 2% by weight to 30% by weight.

The base preferably is capable of generating carbon dioxide. Examples of useful bases include water soluble carbonates and bicarbonates. Further specific examples of suitable bases include sodium bicarbonate such as "Effer-Soda", sodium carbonate, sodium sesqui-carbonate, potassium carbonate, potassium bicarbonate, ammonium bicarbonate, calcium carbonate, magnesium carbonate, sodium glycine carbonate, L-lysine carbonate, arginine carbonate, zinc carbonate, and mixtures thereof. The base is present in the immediate release composition in an amount of from 1% by weight to 60% by weight or from 2% by weight to 50% by weight.

In one or more embodiments the effervescent couple is selected from citric acid+NaHCO$_3$, Tartaric acid+NaHCO$_3$, Succinic acid+NaHCO$_3$, Malonic acid+NaHCO$_3$, Benzoic acid+NaHCO$_3$, Oxalic acid+NaHCO$_3$, Malic acid+NaHCO$_3$ and Glutaric acid+NaHCO$_3$ Examples of suitable disintegrants include Sodium starch glycolate, Povidone, Sodium alginate, Alginic acid, Calcium alginate, Carboxymethylcellulose calcium, Carboxymethylcellulose sodium, Powdered cellulose, Chitosan, Croscarmellose sodium (Croscarmellose Na), Crospovidone, Cross-linked polyvinylpyrrolidone, Hydroxypropyl starch, Hydroxypropyl cellulose low-substituted, Magnesium aluminium silicate, Methylcellulose, Microcrystalline cellulose, pregelatinized starch, Docusae sodium, Guar gum, Polacrilin potassium. The disintegrant is present in the immediate release composition in an amount of from 1% by weight to 60% by weight, from 5% by weight to 50% by weight.

In one or more embodiments, the disintegrant is Croscarmellose sodium.

Normally, the concentration of the one or more disintegrants, and/or effervescent agent is from 1% w/w to 80% w/w such as, for example, from 5% w/w to 70% w/w, from 10% w/w to 60% w/w.

One or more pharmaceutically acceptable excipients or additives may also be present (see the section "Pharmaceutically acceptable excipients").

Pharmaceutically Acceptable Excipients

The immediate release composition may also contain other excipients as well, for example in order to improve the technical properties of the immediate release composition so that it may be easier to produce or in order to improve the properties of the immediate release composition such as release rate of the drug substance, stability of the drug substance or of the composition itself etc.

A suitable pharmaceutically acceptable excipient for use in an immediate release composition of the invention may be selected from fillers, diluents, disintegrants, glidants, pHadjusting agents, viscosity adjusting agents, solubility increasing or decreasing agents, osmotically active agents and solvents.

Normally excipients like glidants/lubricants are included in a concentration of from 0 to 5% w/w, binders in a concentration of from 0 to 25% w/w, solubility increasing agents in a concentration of from 0 to 15% w/w, stabilizers in a concentration of 0 to 15% w/w and modifiers in a concentration of 0 to 15% w/w.

Suitable excipients include conventional tablet or capsule excipients. These excipients may be, for example, diluents such as dicalcium phosphate, calcium sulphate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as alginic acid, calcium alginate, sodium alginate, starch, gelatin, saccharides (including glucose, sucrose, dextrose and lactose), molasses, panwar gum, ghatti gum, mucilage of isapol husk, carboxymethylcellulose, methylcellulose, veegum, larch arabolactan, polyethylene glycols, ethylcellulose, water, alcohols, waxes, polyvinylpyrrolidone such as, for example, PVP K90 or mixtures thereof; lubricants such as talc, silicium dioxide, magnesium stearate, calcium stearate, stearic acid, hydrogenated vegetable oils, sodium benzoate, sodium chloride, leucine, carbowax 4000, magnesium lauryl sulphate, Sodium laurylsulphate, Stearyl alcohol, Polysorbate 20, Polysorbate 60, Polysorbate 80, Macrogol stearate, Macrogol lauryl ether, Stearoyl macrogolglycerides, Sorbitan stearate, Sorbitan laurate, Macrogol glycerol hydroxystearat, colloidal silicon dioxide and mixtures thereof, disintegrants such as starches, clays, cellulose derivatives including microcrystalline cellulose, methycellulose, carboxymethycellulose calcium, carboxymethylcellulose sodium, cellulose, crosscarmellose sodium, gums, aligns, various combinations of hydrogencarbonates with weak acids (for example sodium hydrogencarbonate/tartaric acid or citric acid) crosprovidone, sodium starch glycolate, agar, alginic acid, calcium alginate, sodium alginate, chitosan, colloidal silicon dioxide, docusate sodium, guar gum, low-substituted hydroxypropyl cellulose, hydroxypropyl starch, magnesium aluminium silicate, polacrilin potassium, povidone, sodium starch glycolate, pregelatinized starch, cation exchange resins, citrus pulp, veegum, glycollate, natural sponge, bentonite, sucralfate, calcium hydroxyl-apatite or mixtures thereof, effervescent agents (carbonate release) such as citric acid, anhydrous, citric acid, monohydrate, dextrates, fumaric acid, potassium bicarbonate, sodium bicarbonate, sodium citrate, dehydrate, tartaric acid or mixtures thereof.

Furthermore, the immediate release composition may comprise one or more agents selected from sweetening agents, flavouring agents and colouring agents, in order to provide an elegant and palatable preparation. Examples are maltol, citric acid, water soluble FD&C dyes and mixtures thereof with corresponding lakes and direct compression sugars such as Di-Pac from Amstar. In addition, coloured dye migration inhibitors such as tragacanth, acacia or attapulgite talc may be added. Specific examples include Calcium carbonate, 1,3,5-trihydroxybenzene, Chromium-cobalt-aluminium oxide, ferric ferrocyanide, Ferric oxide, Iron ammonium citrate, Iron (III) oxide hydrated, Iron oxides, Carmine red, Magnesium carbonate and Titanium dioxide.

Plasticizer may be incorporated in the immediate release composition. A suitable plasticizer is selected from such as for example mono- and di-acetylated monoglycerides, diacetylated monoglycerides, acetylated hydrogenated cottonseed glyceride, glycerol cocoate, Polyethylene glycols or polyethylene oxides (for example with a molecular weight of 1,000-500,000 Daltons), dipropylene glycol salicylate glycerin, fatty acids and esters, phthalate esters, phosphate esters, amides, diocyl phthalate, phthalyl glycolate, mineral oils, hydrogenated vegetable oils, vegetable oils, acetylated hydrogenated soybean oil glycerides, Castor oil, acetyl tributyl citrate, acetyl triethyl citrate, methyl abietate, nitrobenzene, carbon disulfide, β-naphtyl salicylate, sorbitol, sorbitol glycerol tricitrate, fatty alcohols, cetostearyl alcohol, cetyl alcohol, stearyl alcohol, oleyl alcohol, myristyl alcohol, sucrose octaacetate, alfa-tocopheryl polyethylene glycol succinate (TPGS), tocopheryl derivative, diacetylated monoglycerides, diethylene glycol monostearate, ethylene glycol monostearate, glycerol monooleate, glycerol monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters, amyl oleate, butyl oleate, butyl stearate, diethylene glycol monolaurate, glycerol tributyrate, Cumar W-1, Cumar MH-1, Cumar V-1, Flexol B-400, monomeric polyethylene ester, Piccolastic A-5, Piccalastic A-25, Beckolin, Clorafin 40, acetyl tributyl citrate, acetyl triethyl citrate, benzyl benzoate, butoxyethyl stearate, butyl and glycol esters of fatty acids, butyl diglycol carbonate, butyl ricinoleate, butyl phthalyl butyl glycolate, camphor, dibutyl sebacate, dibutyl tartrate, diphenyl oxide, glycerine, HB-40, hydrogenated methyl ester of rosin, methoxyethyl oleate, monoamylphthalate, Nevillac 10, Paracril 26, technical hydroabietyl alcohol, triethylene glycol dipelargonate, solid aliphatic alcohols, nitrobenzene, carbon disulfide, β-naphtyl salicylate, phthalyl glycolate, dioctyl phthalate and mixtures thereof.

Chemical stabilizers may be incorporated in the immediate release composition. A suitable chemical stabilizer is selected from TPG for example in the form of TPGS due to surfactant properties, BHA, BHT, t-butyl hydroquinone, calcium ascorbate, gallic acid, hydroquinone, maltol, octyl gallate, sodium bisulfite, sodium metabisulfite, tocopherol and derivates thereof, citric acid, tartaric acid, and ascorbic acid. Other stabilisers include trivalent phosphorous like e.g. phosphite, phenolic antioxidants, hydroxylamines, lactones such as substituted benzofuranones. Hindered phenols, thiosynergists and/or hindered amines, acids (ascorbic acid, erythorbic acid, etidronic acid, hypophosphorous acid, nordihydroguaiaretic acid, propionic acid), phenols, dodecyl gallate, octyl gallate, 1,3,5-trihydroxybenzene, organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol, D-α-tocopherol, DL-α-tocopherol, tocopheryl acetate, d-α-tocopheryl acetate, dl-α-tocopheryl acetate. However, other anti-oxidative agents known in the art may be used according to the present invention. Other suitable stabilizer is selected from such as for example sorbitol glycerol tricitrate, sucrose octaacetate.

A release modifier may be incorporated in the immediate release composition. A suitable release modifier is selected from such as for example fatty acids and esters, fatty alcohols, cetyl alcohol, stearyl alcohol, mineral oils, hydrogenated vegetable oils, vegetable oils, acetylated hydrogenated soybean oil glycerides, Castor oil, phosphate esters, amides, phthalate esters, glycerol cocoate, oleyl alcohol, myristyl alcohol, sucrose octaacetate, diacetylated monoglycerides, diethylene glycol monostearate, ethylene glycol monostearate, glycerol monooleate, glycerol monostearate, propylene glycol monostearate, macrogol esters, macrogol stearate 400, macrogol stearate 2000, polyoxyethylene 50 stearate, macrogol ethers, cetomacrogol 1000, lauromacrogols, poloxamers, polyvinyl alcohols, sorbitan monolaurate, sorbitan monooleate, sorbitan monopalmitate, sorbitan monostearate, sorbitan sesquioleate, sorbitan trioleate, sorbitan tristearate, ethylcellulose, cellulose acetate, cellulose propionate, cellulose nitrate, cellulose derivative selected from methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose, cellulose acetate, polylactic acid or polyglycolic acid and copolymers thereof, methacrylates, a co-polymer of methacrylate-galactomannan, Polyvinyl alcohols, glycerinated gelatin, cocoa butter.

Other suitable release modifiers may be selected from inorganic acids, inorganic bases, inorganic salts, organic acids or bases and pharmaceutically acceptable salts thereof, saccharides, oligosaccharides, polysaccharides, polyethylene glycol derivatives and cellulose and cellulose derivatives.

Alternatively or additionally, a suitable pharmaceutically acceptable excipient is a mono-, di-, oligo, polycarboxylic acid or amino acids such as, for example acetic acid, succinic acid, citric acid, tartaric acid, acrylic acid, benzoic acid, malic acid, maleic acid, sorbic acid, aspartic acid, glutamic acid.

Examples of suitable organic acids include acetic acid/ethanoic acid, adipic acid, angelic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, oxamic acid, pimelic acid, and pyruvic acid.

Examples of suitable inorganic acids include pyrophosphoric, glycerophosphoric, phosphoric such as ortho- and meta phosphoric acid, boric acid, hydrochloric acid, and sulfuric acid.

Examples of suitable inorganic compounds include aluminium.

Examples of organic bases are p-nitrophenol, succinimide, benzenesulfonamide, 2-hydroxy-2cyclohexenone, imidazole, pyrrole, diethanolamine, ethyleneamine, tris(hydroxymethyl)aminomethane, hydroxylamine and derivates of amines, sodium citrate, aniline, hydrazine.

Examples of inorganic bases include aluminium oxide such as, for example, aluminium oxide trihydrate, alumina, sodium hydroxide, potassium hydroxide, calcium carbonate, ammonium carbonate, ammonium hydroxide, and the like.

Suitable pharmaceutically acceptable salts of an organic acid is for example an alkali metal salt or an alkaline earth metal salt such as, for example sodium phosphate, sodium dihydrogenphosphate, disodium hydrogenphosphate, potassium phosphate, potassium dihydrogenphosphate, potassium hydrogenphosphate, calcium phosphate, dicalcium phosphate sodium sulphate, potassium sulphate, calcium sulphate, sodium carbonate, sodium hydrogencarbonate, potassium carbonate, potassium hydrogencarbonate, calcium carbonate, magnesium carbonate, sodium acetate, potassium acetate, calcium acetate, sodium succinate, potassium succinate, calcium succinate, sodium citrate, potassium citrate, calcium citrate, sodium tartrate, potassium tartrate, calcium tartrate.

A suitable inorganic salt for use in an immediate release composition of the invention is sodium chloride, potassium chloride, calcium chloride, magnesium chloride.

Saccharides such as glucose, ribose, arabinose, xylose, lyxose, xylol, allose, altrose, inosito, glucose, sorbitol, mannose, gulose, Glycerol, idose, galactose, talose, maltose, mannitol, erythritol, ribitol, xylitol, maltitol, isomalt, lactitol, sucrose, fructose, lactose, dextrin, dextran, amylose, xylan.

Cellulose and cellulose derivative selected from methylcellulose, carboxymethylcellulose and salts thereof, microcrystalline cellulose, ethylhydroxyethylcellulose, ethylcellulose, cellulose acetate, cellulose proprionate, cellulose nitrate, cellulose acetate phthalate, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose.

Drug Substances for Use in an Immediate Release Composition of the Invention

An immediate release composition according to the invention comprises one or more drug substances. The amount of substance is determined by the therapeutic index of the indication for which the drug substance is intended. Typically, the amount of the drug substance corresponds to a daily or part of a daily therapeutic dose.

An immediate release composition according to the invention is suitable for use for both water soluble as well as slightly soluble or insoluble drug substances.

Thus, an immediate release composition according to the invention may comprise one or more drug substances, i.e. substances, which are therapeutically, prophylactically, diagnostically and/or biologically drug substance. The term "drug substance" as used herein broadly includes any compound, or mixture thereof, that can be delivered from the immediate release composition to produce a beneficial result, such as, for example, but not limited to, an anti-inflammatory effect, an antirheumatic effect, an analgesic effect, an antimigraine effect, an antiepileptic effect, an anticholinergic effect, a dopaminergic effect, an antipsychotic effect, an anxiolytic effect, a hypnotic and/or sedative effect or an antidepressant effect, depending on the specific drug substance comprised by the immediate release composition.

Examples of specific drug substances suitable for use in an immediate release composition of the invention are:

Antiinflammatory and antirheumatic drug substances, such as, for example; Butylpyrazolidines, Phenylbutazone, Mofebutazone, Oxyphenbutazone, Clofezone, Kebuzone, Acetic acid derivatives and related substances, Indometacin, Sulindac, Tolmetin, Zomepirac, Diclofenac, Alclofenac, Bumadizone, Etodolac, Lonazolac, Fentiazac, Acemetacin, Difenpiramide, Oxametacin, Proglumetacin, Ketorolac, Aceclofenac, Bufexamac, Oxicams, Piroxicam, Tenoxicam, Droxicam, Lornoxicam, Meloxicam, Propionic acid derivatives, Ibuprofen, Naproxen, Ketoprofen, Fenoprofen, Fenbufen, Benoxaprofen, Suprofen, Pirprofen, Flurbiprofen, Indoprofen, Tiaprofenic acid, Oxaprozin, Ibuproxam, Dexibuprofen, Flunoxaprofen, Alminoprofen, Dexketoprofen, Fenamates, Mefenamic acid, Tolfenamic acid, Flufenamic acid, Meclofenamic acid, Coxibs, Celecoxib, Rofecoxib, Valdecoxib, Parecoxib, Etoricoxib, Lumiracoxib, Nabumetone, Niflumic acid, Azapropazone, Glucosamine, Benzydamine, Glucosaminoglycan polysulphate, Proquazone, Orgotein, Nimesulide, Feprazone, Diacerein, Morniflumate, Tenidap, Oxaceprol, Chondroitin sulphate, Feprazone, Dipyrocetyl, Acetylsalicylic acid, Quinolines, Oxycinchophen, Gold preparations, Sodium aurothiomalate, Sodium aurotiosulphate, Auranofin, Aurothioglucose, Aurotioprol, Penicillamine, Bucillamine.

Analgesics, such as, for example; Opioids, Natural opium alkaloids, semi-synthetic opium alkaloids, Morphine, Opium, Hydromorphone, Nicomorphine, Oxycodone, Dihydrocodeine, Diamorphine, Papaveretum, Codeine, Phenylpiperidine derivatives, Ketobemidone, Pethidine, Fentanyl, Diphenylpropylamine derivatives, Dextromoramide, Piritramide, Dextropropoxyphene, Bezitramide, Methadone, Benzomorphan derivatives, Pentazocine, Phenazocine, Oripavine derivatives, Buprenorphine, Morphinan derivatives, Butorphanol, Nalbuphine, Tilidine, Tramadol, Dezocine, Salicylic acid and derivatives, Acetylsalicylic acid, Aloxiprin, Choline salicylate, Sodium salicylate, Salicylamide, Salsalate, Ethenzamide, Morpholine salicylate, Dipyrocetyl, Benorilate, Diflunisal, Potassium salicylate, Guacetisal, Carbasalate calcium, Imidazole salicylate, Pyrazolones, Phenazone, Metamizole sodium, Aminophenazone, Propyphenazone, Nifenazone, Anilides, Paracetamol, Phenacetin, Bucetin, Propacetamol, Other analgesics and antipyretics, Rimazolium, Glafenine, Floctafenine, Viminol, Nefopam, Flupirtine, Ziconotide.

Anesthetics, such as, for example; Ethers, Diethyl ether, Vinyl ether, Halogenated hydrocarbons, Halothane, Chloroform, Methoxyflurane, Enflurane, Trichloroethylene, Isoflurane, Desflurane, Sevoflurane, Barbiturates, Methohexital, Hexobarbital, Thiopental, Narcobarbital, Opioid anesthetics, Fentanyl, Alfentanil, Sufentanil, Phenoperidine, Anileridine, Remifentanil, Other general anesthetics, Droperidol, Ketamine, Propanidid, Alfaxalone, Etomidate, Propofol, Hydroxybutyric acid, Nitrous oxide, Esketamine, Xenon, Esters of aminobenzoic acid, Metabutethamine, Procaine, Tetracaine, Chloroprocaine, Benzocaine, Amides, Bupivacaine, Lidocaine, Mepivacaine, Prilocaine, Butanilicaine, Cinchocaine, Etidocaine, Articaine, Ropivacaine, Levobupivacaine, Esters of benzoic acid, Cocaine, Other local anesthetics, Ethyl chloride, Dyclonine, Phenol, Capsaicin.

Antimigraine drug substances, such as, for example; Ergot alkaloids, Dihydroergotamine, Ergotamine, Methysergide, Lisuride, Corticosteroid derivatives, Flumedroxone, Selective serotonin (5HT1) agonists, Sumatriptan, Naratriptan, Zolmitriptan, Rizatriptan, Almotriptan, Eletriptan, Frovatriptan, Other antimigraine preparations, Pizotifen, Clonidine, Iprazochrome, Dimetotiazine, Oxetorone.

Antiepileptic drug substances such as, for example; Barbiturates and derivatives, Methylphenobarbital, Phenobarbital, Primidone, Barbexaclone, Metharbital, Hydantoin derivatives, Ethotoin, Phenytoin, Amino(diphenylhydantoin) valeric acid, Mephenytoin, Fosphenytoin, Oxazolidine derivatives, Paramethadione, Trimethadione, Ethadione, Succinimide derivatives, Ethosuximide, Phensuximide, Mesuximide, Benzodiazepine derivatives, Clonazepam, Carboxamide derivatives, Carbamazepine, Oxcarbazepine, Rufinamide, Fatty acid derivatives, Valproic acid, Valpromide, Aminobutyric acid, Vigabatrin, Progabide, Tiagabine, Other antiepileptics, Sultiame, Phenacemide, Lamotrigine, Felbamate, Topiramate, Gabapentin, Pheneturide, Levetiracetam, Zonisamide, Pregabalin, Stiripentol, Lacosamide, Beclamide.

Anticholinergic drug substances, such as, for example; Tertiary amines, Trihexyphenidyl, Biperiden, Metixene, Procyclidine, Profenamine, Dexetimide, Phenglutarimide, Mazaticol, Bornaprine, Tropatepine, Ethers chemically close to antihistamines, Etanautine, Orphenadrine (chloride), Ethers of tropine or tropine derivatives, Benzatropine, Etybenzatropine.

Dopaminergic ative substances, such as, for example; Dopa and dopa derivatives, Levodopa, Melevodopa, Etilevodopa, Adamantane derivatives, Amantadine, Dopamine agonists, Bromocriptine, Pergolide, Dihydroergocryptine mesylate, Ropinirole, Pramipexole, Cabergoline, Apomorphine, Piribedil, Rotigotine, Monoamine, oxidase B inhibitors, Selegiline, Rasagiline, other dopaminergic agents, Tolcapone, Entacapone, Budipine.

Antipsychotic drug substances, such as, for example; Phenothiazines with an aliphatic side-chain, Chlorpromazine, Levomepromazine, Promazine, Acepromazine, Triflupromazine, Cyamemazine, Chlorproethazine, Phenothiazines with piperazine structure, Dixyrazine, Fluphenazine, Perphenazine, Prochlorperazine, Thiopropazate, Trifluoperazine, Acetophenazine, Thioproperazine, Butaperazine, Perazine, Phenothiazines with piperidine structure, Periciazine, Thioridazine, Mesoridazine, Pipotiazine, Butyrophenone derivatives, Haloperidol, Trifluperidol, Melperone, Moperone, Pipamperone, Bromperidol, Benperidol, Droperidol, Fluanisone, Indole derivatives, Oxypertine, Molindone, Sertindole, Ziprasidone, Thioxanthene derivatives, Flupentixol, Clopenthixol, Chlorprothixene, Tiotixene, Zuclopenthixol, Diphenylbutylpiperidine derivatives, Fluspirilene, Pimozide, Penfluridol, Diazepines, oxazepines and thiazepines, Loxapine, Clozapine, Olanzapine, Quetiapine, Neuroleptics, in tardive dyskinesia, Tetrabenazine, Benzamides, Sulpiride, Sultopride, Tiapride, Remoxipride, Amisulpride, Veralipride, Levosulpiride, Lithium, Other antipsychotics, Prothipendyl, Risperidone, Clotiapine, Mosapramine, Zotepine, Aripiprazole, Paliperidone.

Anxiolytic drug substances, such as, for example; Benzodiazepine derivatives, Diazepam, Chlordiazepoxide, Medazepam, Oxazepam, Potassium clorazepate, Lorazepam, Adinazolam, Bromazepam, Clobazam, Ketazolam, Prazepam, Alprazolam, Halazepam, Pinazepam, Camazepam, Nordazepam, Fludiazepam, Ethyl loflazepate, Etizolam, Clotiazepam, Cloxazolam, Tofisopam, Diphenylmethane derivatives, Hydroxyzine, Captodiame, Carbamates, Meprobamate, Emylcamate, Mebutamate, Dibenzo-bicyclo-octadiene derivatives, Benzoctamine, Azaspirodecanedione derivatives, Buspirone, Other anxiolytics, Mephenoxalone, Gedocarnil, Etifoxine.

Hypnotic and sedative drug substances, such as, for example; Barbiturates, Pentobarbital, Amobarbital, Butobarbital, Barbital, Aprobarbital, Secobarbital, Talbutal, Vinylbital, Vinbarbital, Cyclobarbital, Heptabarbital, Reposal, Methohexital, Hexobarbital, Thiopental, Etallobarbital, Allobarbital, Proxibarbal, Aldehydes and derivatives, Chloral hydrate, Chloralodol, Acetylglycinamide chloral hydrate, Dichloralphenazone, Paraldehyde, Benzodiazepineemepronium derivatives, Flurazepam, Nitrazepam, Flunitrazepam, Estazolam, Triazolam, Lormetazepam, Temazepam, Midazolam, Brotizolam, Quazepam, Loprazolam, Doxefazepam, Cinolazepam, Piperidinedione derivatives, Glutethimide, Methyprylon, Pyrithyldione, Benzodiazepine related drugs, Zopiclone, Zolpidem, Zaleplon, Ramelteon, Other hypnotics and sedatives, Methaqualone, Clomethiazole, Bromisoval, Carbromal, Scopolamine, Propiomazine, Triclofos, Ethchlorvynol, Valerian, Hexapropymate, Bromides, Apronal, Valnoctamide, Methylpentynol, Niaprazine, Melatonin, Dexmedetomidine, Dipiperonylaminoethanol.

Antidepressant drug substances, such as, for example; Non-selective monoamine reuptake inhibitors, Desipramine, Imipramine, Imipramine oxide, Clomipramine, Opipramol, Trimipramine, Lofepramine, Dibenzepin, Amitriptyline, Nortriptyline, Protriptyline, Doxepin, Iprindole, Melitracen, Butriptyline, Dosulepin, Amoxapine, Dimetacrine, Aminneptine, Maprotiline, Quinupramine, Selective serotonin reuptake inhibitors, Zimeldine, Fluoxetine, Citalopram, Paroxetine, Sertraline, Alaproclate, Fluvoxamine, Etoperidone, Escitalopram, Monoamine oxidase inhibitors, non-selective, Isocarboxazid, Nialamide, Phenelzine, Tranylcypromine, Iproniazide, Iproclozide, Monoamine oxidase A inhibitors, Moclobemide, Toloxatone, Other antidepressants, Oxitriptan, Tryptophan, Mianserin, Nomifensine, Trazodone, Nefazodone, Minaprine, Bifemelane, Viloxazine, Oxaflozane, Mirtazapine, Medifoxamine, Tianeptine, Pivagabine, Venlafaxine, Milnacipran, Reboxetine, Gepirone, Duloxetine, Agomelatine, Desvenlafaxine, Centrally acting sympathomimetics, Amphetamine, Dexamphetamine, Metamphetamine, Methylphenidate, Pemoline, Fencamfamin, Modafinil, Fenozolone, Atomoxetine, Fenetylline, Xanthine derivatives, Caffeine, Propentofylline, Other psychostimulants and nootropics, Meclofenoxate, Pyritinol, Piracetam, Deanol, Fipexide, Citicoline, Oxiracetam, Pirisudanol, Linopirdine, Nizofenone, Aniracetam, Acetylcarnitine, Idebenone, Prolintane, Pipradrol, Pramiracetam, Adrafinil, Vinpocetine.

Anti-dementia drug substances, such as, for example; Anticholinesterases, Tacrine, Donepezil, Rivastigmine, Galantamine, Other anti-dementia drugs, Memantine, Ginkgo biloba.

Other nervous system drug substances, such as, for example; Parasympathomimetics, Anticholinesterases, Neostigmine, Pyridostigmine, Distigmine, Ambenonium, Choline esters, Carbachol, Bethanechol, Other parasympathomimetics, Pilocarpine, Choline alfoscerate.

Drug substances used in addictive disorders, such as, for example; Nicotine, Bupropion, Varenicline, Disulfiram, Calcium carbimide, Acamprosate, Naltrexone, Buprenorphine, Methadone, Levacetylmethadol, Lofexidine. Antivertigo drug substances, such as, for example; Betahistine, Cinnarizine, Flunarizine, Acetylleucine, other nervous system drugs, Gangliosides and ganglioside derivatives, Tirilazad, Riluzole, Xaliproden, Hydroxybutyric acid, Amifampridine.

Opium alkaloids and derivatives, such as, for example, Ethylmorphine, Hydrocodone, Codeine, Opium alkaloids with morphine, Normethadone, Noscapine, Pholcodine, Dextromethorphan, Thebacon, Dimemorfan, Acetyldihydrocodeine, Benzonatate, Benproperine, Clobutinol, Isoaminile, Pentoxyverine, Oxolamine, Oxeladin, Clofedanol, Pipazetate, Bibenzonium bromide, Butamirate, Fedrilate, Zipeprol, Dibunate, Droxypropine, Prenoxdiazine, Dropropizine, Cloperastine, Meprotixol, Piperidione, Tipepidine, Morclofone, Nepinalone, Levodropropizine, Dimethoxanate.

In preferred embodiments, the drug substance is selected from the therapeutic classes including non-steroids anti-inflammatory and antirheumatic drug substances.

In preferred embodiments, the drug substance is from the therapeutic classes including analgesics, opioids, antipyretics, anaesthetics, antimigraine agents, antiepileptics, antiparkinson agents, dopaminergic agents, antipsychotics, anxiolytics, sedatives, antidepressants, psychostimulants agents, dopamine, noradrenaline, nicotinic, alfa-andrenergic, serotonin, $H_3$ antagonist used for ADHD and nootropics agents used in addictive disorders.

In preferred embodiments, the drug substance is from the therapeutic classes including anaesthetics, centrally-acting analgesics, sedative-hypnotics, anxiolytics; appetite suppressants, decongestants, antitussives, antihistamines, antiemetics, antidiarrheals, and drugs used to treat narcolepsy and attention deficit hyperactivity disorder.

In preferred embodiments, the drug substance is associated with abuse syndromes include opioids, CNS depressants, CNS stimulants, cannabinoids, nicotine-like compounds, glutamate antagonists and N-methyl-D-aspartate (NMDA) antagonists.

In preferred embodiments, the drug substance is buprenorphine, codeine, dextromoramide, dihydrocodeine, fentanyl, hydrocodone, hydromorphone, morphine, pentazocine, oxycodeine, oxycodone, oxymorphone and tramadol.

In preferred embodiments, the drug substance is amphetamine, metamphetamine dexamphetamine, lisdexamphetamine, methylphenidate and dexmethylphenidate.

In preferred embodiments, the drug substances have abuse potential or safety risk. In principle, the use of an immediate release composition to avoid alcohol dose dumping can be of relevance for any drug substance. However, the main interest is with respect to drug substances with abuse potential or safety risk.

Examples of drug substances with abuse potential or safety risk suitable for use according to the present invention are:

1-(1-Phenylcyclohexyl)pyrrolidine, 1-(2-Phenylethyl)-4-phenyl-4-acetoxypiperidine, 1-[1-(2-Thienyl)-cyclohexyl]piperidine, 1-[1-(2-Thienyl)cyclohexyl]pyrrolidine, 1-Methyl-4-phenyl-4-propionoxy-piperidine, 1-Phenylcyclohexylamine, 1-Piperidinocyclohexane-carbonitrile, 2,5-Dimethoxy-4-ethylamphetamine, 2,5-Dimethoxyamphetamine, 2C-B (i.e. 4-bromo-2,5-dimethoxypenethylamine), 2C-D (i.e. 2,5-dimethoxy-4-methylphenethylamine), 2C-I (i.e. 4-iodo-2,5-dimethoxyphenethylamine), 2C-T-2 (i.e. 2,5-dimethoxy-4-ethylthiophenethylamine), 2C-T-4 (i.e. 2,5-dimethoxy-4-isopropyl thiophenethylamine), 2C-T-7 (i.e. 2,5-dimethoxy-4-(n)-propylthiopenethylamine), 3,4-Methylenedioxymethamphetamine, 3,4,5-Trimethoxyamphetamine, 3,4-Methylenedioxyamphetamine, 3,4-Methylenedioxy-N-ethylamphetamine, 3-Methylfentanyl, 3-Methylthiofentanyl, 4-Bromo-2,5-dimethoxyamphetamine, 4-Bromo-2,5-dimethoxy-phenethylamine, 4-Methoxyamphetamine, 4-Methyl-2,5-dimethoxyamphetamine, 4-Methylaminorex (cis isomer), 5-MeO-DIPT (i.e. 5-Methoxy-N,N-diisopropyltryptamine), 5-MeO-DMT (i.e. 5-Methoxy-N,N-dimethyltryptamine), 5-Methoxy-3,4-methylenedioxyamphetamine, Acetorphin, Acetorphine, Acetyl-alpha-methylfentanyl, Acetyldihydrocodeine, Acetylmethadol, Alfentanil, Allobarbital, Allylprodin, Allylprodine, Alphacetylmethadol, levo-alphacetylmethadol, Alpha-ethyltryptamine, Alphameprodine, Alphamethadol, Alpha-Methylfentanyl, Alpha-Methylthiofentanyl, Alphaprodine, Alprazolam, Amfepramon, Amfetaminil, Amineptin, Aminorex, Amobarbital, Amphetamine, Dexamphetamine, Lisdexamphetamine, Amylnitrit (all isomers of the amyl group), Anabolic steroids, Anileridine, Aprobarbital, Barbital, Barbituric acid derivative, BDB (i.e. 3,4-methylenedioxyphenyl)-2-butanamine), Benzethidin, Benzethidine, Benzoylecgonine, Benzphetamine, Benzphetamine, Benzylmethylketon, Benzylmorphine, Betacetylmethadol, Beta-Hydroxy-3-methylfentanyl, Beta-Hydroxyfentanyl, Betameprodine, Betameprodine, Betamethadol, Betaprodine, Bezitramide, Bezitramide, Boldenone, Brolamfetamin, Bromazepam, Brotizolam, Bufotenine, Buprenorphine, Butabarbital, Butalbital, Butobarbital, Butorphanol, BZP (A 2)(i.e. 1-benzylpiperazin), Camazepam, Cannabis, Carfentanil, Catha edulis, Cathine, Cathinone, Chloral betaine, Chloral hydrate, Chlordiazepoxide, Chlorhexadol, Chlorotestosterone (same as clostebol), Chlorphentermine, Clobazam, Clonazepam, Clonitazene, Clonitazene, Clorazepate, Clortermine, Clostebol, Clotiazepam, Cloxazolam, Coca Leaves, Cocaine, Codeine, Codeine & isoquinoline alkaloid, Codeine methylbromide, Codeine-N-oxide, Codoxim, Cyclobarbital (Hexemal NFN), Cyprenorphine, Dehydrochlormethyltestosterone, Delorazepam, Desomorphine, Dexamphetamine, Dexfenfluramine, Dextromoramide, Dextropropoxyphene, Diacetylmorphine, Diampromide, Diazepam, Dichloralphenazone, Diethylpropion, Diethylthiambutene, Diethyltryptamine, Difenoxin, Dihydrocodeine, Dihydroetorphine, Dihydromorphine, Dihydrotestosterone, Dimenoxadol, Dimepheptanol, Dimethylthiambutene, Dimethyltryptamine, Dioxaphetyl butyrate, Diphenoxylate, Dipipanone, Diprenorphine, Dronabinol, Drostanolone, Drotebanol, Ecgonine, Estazolam, Ethchlorvynol, Ethinamate, Ethyl loflazepate, Ethylestrenol, Ethylmethylthiambutene, Ethylmorphine, Ethylmorphine, Eticyclidin, Etilamphetamine, Etonitazene, Etorphine, Etoxeridine, Etryptamine, Fencamfamin, Fenethylline, Fenetylline, Fenfluramine, Fenproporex, Fentanyl, Fludiazepam, Flunitrazepam, Fluoxymesterone, Flurazepam, Formebolone, Fungi and Spores of the species *Psilocybe Semilanceata*, Furethidine, Gammahydroxybutanic acid, Glutethimide, Halazepam, Haloxazolam, Heroine, Hydrocodone, Hydrocodone & isoquinoline alkaloid, Hydromorphinol, Hydromorphone, Hydroxypethidine, Ibogaine, Isobutylnitrit, Isomethadone, Ketamine, Ketazolam, Ketobemidone, Levamphetamine, Levo-alphacetylmethadol, Levo-methamphetamine, Levomethorphan, Levomoramide, Levophenacylmorphan, Levorphanol, Loprazolam, Lorazepam, Lormetazepam, Lysergic acid, Lysergic acid amide, Lysergic acid diethylamide, Marijuana, Mazindol, MBDN (i.e. N-methyl-1-(3,4-methylenedioxyphenyl)-2-butanamine), mCPP (i.e. 1-(3-chlorophenyl)piperazine), Mebutamate, Mecloqualone, Medazepam, Mefenorex, MeOPP (i.e. 1-(4-methoxyphenyl)piperazine), Meperidine, Meperidine intermediate, Meprobamate, Mescaline, Mesocarb, Mesterolone, Metamphetamine, Metazocine, Methadone, Methadone intermediate, Methamphetamine, Methandienone, Methandranone, Methandriol, Methandrostenolone, Methaqualone, Methcathinone, Methenolone, Methohexital, Methyldesorphine, Methyldihydromorphine, Methylphenidate, Dexmethylphenidate, Methylphenobarbital (mephobarbital), Methyltestosterone, Methyprylone, Metopone, Mibolerone, Midazolam, Modafinil, Moramide-intermediate, Morpheridine, Morphine, Morphine methylbromide, Morphine methylsulfonate, Morphine-N-oxide, Myrophine, N,N-Dimethylamphetamine, Nabilone, Nalorphine, Nandrolone, N-Ethyl-1-phenylcyclohexylamine, N-Ethyl-3-piperidyl benzilate, N-Ethylamphetamine, N-Hydroxy-3,4-methylenedioxyamphetamine, Nicocodeine, Nicocodine, Nicodicodine, Nicomorphine, Nimetazepam, Nitrazepam, N-Methyl-3-piperidyl benzilate, Noracymethadol, Norcodeine, Nordiazepam, Norethandrolone, Norlevorphanol, Normethadone, Normorphine, Norpipanone, Norpipanone, Opium, Oxandrolone, Oxazepam, Oxazolam, Oxycodone, Oxymesterone, Oxymetholone, Oxymorphone, Para-Fluorofentanyl, Parahexyl, Paraldehyde, Pemoline, Pentazocine, Pentobarbital, Petrichloral, Peyote, Phenadoxone, Phenampromide, Phenazocine, Phencyclidine, Phendimetrazine, Phenmetrazine, Phenobarbital, Phenomorphan, Phenoperidine, Phentermine, Phenylacetone, Pholcodine, Piminodine, Pinazepam, Pipradrole, Piritramide, PMMA (param-ethyxymethyl amphetamine), Prazepam, Proheptazine, Properidine, Propiram, Psilocybine, Psilocyn, Pyrovalerone, Quazepam, Racemethorphane, Racemoramide, Racemorphane, Remifentanil, Salvia divinorum, Salvinorin A, Secobarbital, Secobarbital, Sibutramine, SPA, Stanolone, Stanozolol, Sufentanil, Sulfondiethylmethane, Sulfonethylmethane, Sulfonmethane, Talbutal, Temazepam, Tenamfetamin, Testolactone, Testosterone, Tetrahydrocannabinols, Tetrazepam, TFMPP (i.e. 1-(3-trifluormethylphenyl)piperazine), Thebacon, Thebaine, Thiamylal, Thiofentanyl, Thiopental, Tiletamine & Zolazepam in Combination, Tilidine, Trenbolone, Triazolam, Trimeperidine, Vinbarbital, Zaleplon, Zipeprol, Zolpidem, Zopiclon.

Other suitable examples include alfentanil, allylprodine, alphaprodine, aniloridine, benzylmorphine, bezitramide, buprenorphine, butophanol, clonitazene, codeine, cyclazocine, desomorphine, dextromoramide, dezocine, diapromide, dihydrocodeine, dihydromorphine, dimenoxadol, dimephetanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narccine, nicomorphine, norlevorphanol, normethadone, nalorphine, normorphine, norpipanone, opium, oxycodone, oxycodeine, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, thebaine, levo-alphacetylmethadol (LAAM), remifentanil, carfentanyl, ohmefentanyl, MPPP (ie. 1-methyl-4-phenyl-4-propionoxypiperidine), prodine, PEPAP (i.e. 4-phenyl-1-(2-phenyl-ethyl)piperidin-4-yl acetate), levomethorphan, etorphine, lefetamine, loperamide, diphenoxylate, pethidine.

Other suitable examples also include Anabolic steroids, cannabis, cocaine and diazepam.

The above mentioned drug substances may also be in the form of pharmaceutically acceptable salts, uncharged or charged molecules, molecular complexes, solvates or anhydrates thereof, and, if relevant, isomers, enantiomers, racemic mixtures, and mixtures thereof.

Furthermore, the drug substance may be in any of its crystalline, polymorphous, semi-crystalline, and amorphous or polyamorphous forms.

The drug substance may by modified to change physical-chemical properties of the drug substance, which may be by increasing or decreasing lipophilicity to modify the release characteristics of the drug substance.

The term "pharmaceutically acceptable salts" of a drug substance includes alkali metal salts such as, for example, sodium or potassium salts, alkaline earth metal salts such as, for example, calcium and magnesium salts, and salts with organic or inorganic acid like for example hydrochloric acid, hydrobromic acid, nitric acid, sulfuric acid, phosphoric acid, citric acid, formic acid, maleic acid, succinic acid, tartaric acid, methane sulphonic acid, toluene sulphonic acid.

The term "solvates" includes hydrates or solvates wherein other solvates than water are involved such as, for example, organic solvents like chloroform and the like.

The concentration of the drug substance in an immediate release composition for use according to the invention depends on several factors, including, for example the specific drug substance, the disease to be treated, the condition of the patient, the age and gender of the patient etc. The above-mentioned drug substances are well-known drug substances and a person skilled in the art will be able to find information as to the dosage of each drug substance and, accordingly, will know how to determine the amount of each drug substance in an immediate release composition.

The drug substance may be a new chemical entity for which the amount of dosing information is limited. In such cases the dosage regimen has to be evaluated based on available preclinical and clinical data.

The drug substance is typically present in an immediate release composition of the invention in a concentration amount of from 0.01% w/w-99% w/w such as, for example, from 0.01% w/w to 90% w/w, from 0.01% w/w to 80% w/w, from 0.01% w/w to 70% w/w, from 0.01% w/w to 50% w/w or from 0.01% w/w to 40% w/w.

In an embodiment of the invention, the drug substance is typically a pharmaceutically active powder. The powder typically has a particle size of from 0.1 µm to 500 µm, typically from 0.5 µm to 300 µm, more typically from 1 µm to 200 µm, especially from 5 µm to 100 µm.

In an embodiment of the invention, the drug substance is a pharmaceutically active crystal. The crystal typically has a particle size of from about 0.1 µm to 1000 µm such as, for example, 0.1 µm to 750 µm, 0.1 µm to 500 µm, typically from 0.5 µm to 500 µm, more typically from 1 µm to 500 µm, especially from 5 µm to 500 µm.

In another embodiment of the invention, an immediate release composition comprises a drug substance that at least partially is present in amorphous form with a mean particle size of at least 0.01 µm such as, for example, from 0.01 µm to 500 µm, from 0.05 µm to 500 µm, from 0.1 µm to 500 µm, from 0.5 µm to 500 µm, 1 µm to 500 µm, typically from 0.5 µm to 300 µm, more typically from 1 µm to 200 µm, especially from 1 µm to 100 µm.

An immediate release composition according to the invention containing a drug substance is typically for oral administration. Due to the possibility of controlling the release rate of the drug substance, the immediate release composition may be adapted for oral administration 1-6 times a day, normally 1-4 times daily such as 1-3 times, 1-2 times or once daily.

Pharmaceutical Compositions

A number of pharmaceutical compositions were developed to reduce the likelihood of improper administration of drugs in combination with alcohol, especially drugs such as opioids or combinations of opioids and relevant drug compounds such as paracetamol or ibuprofen. In general drug substances belonging to the group analgesics, antipyretics or CNS drug substances are of interest. Specific examples are mentioned above.

The drug substance or combination of drug substances may be dispersed in the immediate release composition and, especially in those cases where the immediate release composition contains a polyglycol, the composition is a matrix composition. The immediate release composition according to the invention has a lower solubility and/or release rate in alcohol containing media (for example ethanol) than in aqueous media (for example water, buffer, hydrochloride solution). As demonstrated in the examples herein, the alcohol containing medium may include, for example ethanol in a wide concentration range. Thus, the medium may contain from 2.5% v/v to 80% v/v of alcohol, the remaining part being a water-based medium (i.e. water, aqueous buffer or hydrochloride solution).

More specifically, the invention relates to the use of a polymer and a drug substance for the preparation of an immediate release composition that is without alcohol induced dose dumping. Typically, the solubility or release rate of the immediate release composition is lower in alcohol than that in aqueous media. More specifically, the solubility or release is at least 1.5 times lower, at least 2 times lower in alcohol than in aqueous media, notably 5 times, 10 times, 25 times, 50 times or 100 times lower.

As illustrated in the Examples herein, an immediate release composition of the invention may be a coated matrix composition. The release from such an immediate release composition may be governed by erosion of a specific surface. Erosion based release from a matrix composition depends on the exposed area of the matrix. In this case the area may be manipulated by employment of a coat that is not subject to erosion and thus covering the areas of the matrix that hence will not be a releasing site. For such immediate release compositions the geometric form of the composition is very important for the achieving a desired rate of release. Thus, in one embodiment of the invention, the matrix composition has a geometric shape, which enables a substantially constant surface area to become exposed during erosion of the matrix.

In a specific example, the matrix compositions employed are coated in such a manner that the surface has a substantially constant or controlled surface area during release or erosion. In the present context controlled surface area relates to a predetermined surface area typically predicted from the shape of the coat of the unit dosage system. It may have a simple uniform cylindrical shape or the cylindrical form can have one or more tapered ends in order to decrease (or increase) the initial release period.

As another example, in diffusion based immediate release compositions the release will furthermore depend on the thickness of the diffusion layer and in this case the release will depend both on the diffusion area and thickness of the diffusion composition.

As yet another example the release mechanism of dissolving/solubilisation also depends on the releasing area and the release rate and may be controlled by covering parts of the releasing matrix composition by a coat.

The immediate release composition may be partly covered by a coat with specific properties in such a way that the exposed area of the matrix may be controlled by the use of a coat.

Controlling the coverage of the immediate release composition by the coat hence preferably refers to covering from 0 to 99% w/w of the composition by a coat.

An immediate release composition of the invention is normally prepared for oral intake, preferably for oral intake by swallowing. Accordingly, the size of the immediate release composition should be in a range that allows oral intake by swallowing.

In the following are given illustrative examples of the invention. More specific examples are mentioned in the Examples herein.

In general, the concentration of the polyglycol is from 5% w/w to 90% w/w, the concentration of the drug substance depends on the amount required to have a dose; thus the amount of high potency drug substances is much less than a low potency drug substance. A person skilled in the art is able to find information of suitable doses and adjust the immediate release composition to that effect. Normally, the concentrations of polyglycol and inert pharmaceutically active excipients are lower for immediate release compositions containing a low potency drug substance than for immediate release compositions containing a high potency drug substance.

Geometry

Preferably, the immediate release compositions of the invention are cylindrical compositions optionally with tapered end(s). It follows that the matrix composition also preferably is of a cylindrical shape (optionally with tapered end(s)), which preferably is surrounded by a coating having at least one opening exposing one surface of said matrix.

The cylindrical shape may be any geometrical shape having the same cross section area throughout the length of the geometrical shape. Within the present context, cross sections are perpendicular to the axis of the cylinder. By way of example, if the cylindrical shape is elongated then the cross sections are perpendicular to the longitudinal axis. Preferably, the cylindrical shape is elongated. The cross section of a cylinder within the meaning of the present invention may have any two-dimensional shape, for example the cross section may be circular, oval, parabola, hyperbola, rectangular, triangular, otherwise angular, star shaped or an irregular shape. The immediate release compositions according to the invention preferably have a cylindrical shape, wherein the end(s) may be tapered.

Accordingly, the cylindrical shape may for example be an elliptic cylinder, a parabolic cylinder, a hyperbolic cylinder or a prism. A prism within the present context is a cylinder whose cross-section is a polygon.

The immediate release composition as well as the matrix composition according to the invention may be a cylindrical shape with one tapered end or two tapered ends.

Preferably, the matrix composition is being surrounded by a coating having at least one opening, for example one opening, such as two openings each exposing one surface of said matrix. Preferably, said at least one opening is exposing one end of the cylindrical shape, more preferably the coating has two openings each exposing an end of the cylindrical shape.

Coating

The immediate release composition may be partly covered by a coat with specific properties in such a way that the exposed area of the matrix may be controlled by the use of a coat.

For the present purpose, it is important to ensure that the coating is impermeable to an aqueous medium, such as water. This ensures that the matrix is only in contact with the surrounding aqueous media via the openings in the coating. In addition it is preferred that the coating is also substantially insoluble in an aqueous medium; preferably the coating is insoluble in an aqueous medium.

In a specific example the coating is substantially insoluble, non-erodable and impermeable to aqueous media leaving only the exposed areas of the matrix for release.

Within the present context, the coating is considered substantially insoluble in an aqueous medium if the coating dissolves so much slower in an aqueous medium than the matrix composition that the coating remains intact until the matrix has eroded and/or released the active drug substance.

In an embodiment of the invention, the coating biodegrades, disintegrates crumbles, or dissolves after erosion of the matrix and/or during the release of the drug substance. In certain embodiments, a coating applied to a matrix composition as described herein will remain intact as long as it is supported by the matrix composition containing the drug substance. In specific embodiments, the coating may be is formulated to lose the ability to remain intact after erosion of the matrix composition. For example, the coating may be formulated to biodegrades, disintegrates or crumbles upon erosion of the matrix composition, so that the coating will not remain in a subject to whom the immediate release composition is administered, for example, a human, for any significant amount of time after the complete erosion of the matrix and the release of the drug substance.

In a one embodiment, the coating may biodegrade, disintegrate, crumble or dissolve after erosion of the matrix composition and/or during the release of the drug substance in the matrix composition.

The coating may in general comprise or even consist of one or more polymers. Polymers suited for forming the coating that substantially covers the matrix composition may be selected from thermoplastic polymers. In one embodiment, the coating is formed entirely of thermoplastic polymers. Thus, in one embodiment of the invention all the polymers included in the coating are thermoplastic polymers. As used herein, the term "thermoplastic polymer" refers to polymer(s) that is/are an elastic and flexible liquid when heated, but freezes to a solid state when cooled (for example, cooled to 20° C. or to ambient temperature).

The coating may be made of a material comprising one or more of the polymers described herein in this section, such as, for example, a material comprising one or more starch based polymers, one or more cellulose based polymers, one or more synthetic polymers, one or more biodegradable polymers or a combination thereof, such as mixtures of starch and synthetic polymers or mixtures of starch and biodegradable polymers. In certain embodiments, the coating may be made of a material comprising one or more polymers selected from Ethyl cellulose grade 20 and 100, polylactic acid (PLA), Cornpack 200, polycaprolactone, PEO 7000000 and polyhydroxybuturate.

Starch Based Polymers

The coating may comprise one or more starch based polymers. The starch based polymer may be starch as such or a polymer having a high starch content, preferably more than 70%, such as more than 80%, for example more than 90%. Starch is a linear polysaccaride made up of repeating glucose groups with glycosidic linkages in the 1-4 carbon positions with chain lengths of 500 to 2,000 glucose units. There are two major polymer molecules in starch—amylose and amylopectin.

The starch based polymers to be used according to the present invention may preferably be thermoplastic starch biodegradable plastics (TPS). TPS have a starch (amylose) content greater than 70% and are in general based on gelatinized vegetable starch. Said vegetable starch may for example be selected from potato starch, rice starch, maize starch, tapioca starch, wheat starch, dextrin, carrageenan and chitosan. Said vegetable starch may also as such be suitable polymers used in the coating composition. The group of starch based polymer in general do not have a specified melting point, but changes phase within a temperature range of 90° C. to 260° C. typically depending upon the chain length of the starch based polymer, water content, and their branching and added sidegroups as does the degree of crystallinity of the starch. Long chained-starches are usually completely amorphous, while shorter length starches may be semi-crystalline (20-80% crystalline). Long polymer chains are preferable because it contributes to the hardness, while not being too brittle.

Starch-based polymers are in general fully biodegradable as they are product of plant materials. The degradation rate varies and can be further induced by addition of other biodegradable polymers as listed herein.

One example of a preferred starch based polymer, which may be comprised in the coating or coating according to the present description is maize starch. Maize starch is a linear polysaccaride made up of repeating glucose groups with glycosidic linkages in the 1-4 carbon positions with chain lengths of 500 to 2,000 glucose units. There are two major polymer molecules in starch—amylose and amylopectin. A preferred maize starch is cornpack. Cornpack is the maize starch used in some examples described herein below.

Starch is widely used in food and pharmaceutical industry as binder and diluent. It is edible and essentially nontoxic. Starch is in general cheap and obtains a good hardness when molded and thermoformed. Starch may in general also be reheated several times without losing its thermodynamic properties. Accordingly, in certain embodiments, the coating comprises at least one starch based polymer, and more preferably a starch, because starch may be a great advantage when applying injection molding or co-extrusion as a production process.

Starch based polymers are in general decomposable, and usually have a fast disintegration rate, especially in mixture with biodegradable polymers. These polymers are in generally recognized as stabile and inert in solid dosage forms.

Cellulose Based Polymers

The coating may also comprise one or more cellulose based polymers. In certain embodiments of the invention the coating may even consist of one or more cellulose based polymers (such as ethyl cellulose) and plasticizers (such as any of the plasticizers described in this section below) and UV stabilizers (such as any of the UV stabilizers described in this section below).

Cellulose based polymers are useful in the coating composition because cellulose based polymers for example ethyl cellulose (particularly grade 100-300) frequently have increased hardness and high ductility.

Therefore the coatings used over the matrix composition may include a cellulose based polymer. Where a cellulose based polymer is used in the coating, it is preferably a cellulose based polymer that is substantially insoluble or insoluble in an aqueous medium. Suitable cellulose based polymers include cellulose polymers wherein one or more of the free —OH groups have been substituted with an R-group to form a —O—R group. In this context, R may be, for example, a linear or branched lower alkyl, linear or branched lower alkyl-OH, linear or branched lower alkyl-COOH, —CO-(linear or branched lower alkyl), nitrate, aromatic rings or combinations of the aforementioned. Lower alkyl is preferably a $C_{1-10}$ alkyl, more preferably $C_{1-6}$ alkyl.

Accordingly, where a cellulose based polymer is used in a coating as described herein, the cellulose based polymer may, for example, be one or more selected from ethylcellulose, cellulose acetate, cellulose propionate, cellulose nitrate, methylcellulose, carboxymethylcellulose and salts thereof, cellulose acetate phthalate, ethylhydroxyethylcellulose, ethylmethylcellulose, hydroxymethylcellulose, hydroxyethylmethylcellulose, hydroxypropylcellulose, hydroxypropylmethylcellulose, hydroxymethylcellulose and hydroxymethylpropylcellulose and cellulose acetate.

The coating may also comprise one or more cellulose based polymers selected from cellulose acetate, cellulose propionate, silicified microcrystalline cellulose, cellulose nitrate, methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxylpropylcellulose, hydroxypropylmethylcellulose, hydroxymethylcellulose phthalate, hydroxymethylcellulose and hydroxymethylpropylcellulose, cellulose acetate, ceratonia (high molecular-weight 310 000).

Cellulose based polymers are in general fully biodegradable, as they are typically products of plant materials. The degradation rate of cellulose based polymers is generally slower than for starch based polymers. The degradation rate of cellulose based polymers, however, can be induced by addition of other biodegradable polymers as listed herein. Such additional polymers may be polymers susceptible to degradation by one or more microorganisms, which can result in quicker degradation of the coating composition into smaller pieces, giving rise to an increased surface area, and, thereby, resulting in faster degradation.

It is especially preferred that the coating comprises ethyl cellulose. Ethyl cellulose is a long-chain polymer of β-anhydroglucose units joined together by acetal linkages, in which some of the hydroxyl groups on the repeating glucose units have been converted to ethoxy groups. Ethyl cellulose has the generic formula $C_{12}H_{23}O_6(C_{12}H_{22}O_5)_nC_{12}H_{23}O_5$ where n can vary to provide a wide variety of molecular weights.

Ethyl cellulose comes in different grades which vary in molecular weight and number of ethoxy groups. Grades from 20-300 are suitable for use in the present context and are also readily commercially available. Grades with high molecular weights tend to be preferred because they are optimal to give a hard coating. The coating may comprise one or more ethyl celluloses with different grades, for example one ethyl cellulose with a grade of in the range of 20 to 300, preferably in the range of 20 to 100, more preferably in the range of 20 to 40, such as 20 and another ethyl cellulose with a grade of in the range of 20 to 300, preferably in the range of 50 to 200, more preferably in the range of 80 to 120, such as 100. Ethyl cellulose generally has a glass transition temperature within 129-133° C. These polymers are widely used in food and pharmaceutical industry as coater, stabilizer, matrix former and taste masking and are regarded as non toxic substances.

Cellulose based polymers are in general derived from plant material and may subsequently be modified. Many cellulose based polymers are cheap and give a good hardness when molded and thermoformed. As derivatives of plants, cellulose based polymers are in general easily decomposable when disposed. These polymers tend to be stable and inert in solid dosage.

Synthetic Polymers

The coating according to the invention may also comprise one or more synthetic polymers. Suitable synthetic polymers for use in the coating composition may, for example, be one or more selected from polyamide, polyethylene, polyethylene terephthalate, polypropylene, polyurethane, polyvinyl acetate, polyvinyl alcohol, polyvinyl butural, Eudragit L methyl ester, Eudragit RL and Eudragit E. polyvinyl chloride, silicone rubber, latex, teflon, copolymers such as ethylene vinyl acetate (EVA), styrene-butadienestyrene (SBS) and styrene-isoprene-styrene (SIS), Polyethylene glycols, polyvinylpyrrolidone, polyethylene oxide (ranging in molecular weights 100,000 to 8,000,000), carboxymethylene (Carbomer) and sugars thereof (for example allylsucrose) and co-polymers of ethylene and propylene oxide (PoloXamer).

Biodegradable Polymers

Biodegradation is the process by which microorganisms (microbes such as bacteria, fungi or algae) convert materials into biomass, carbon dioxide and water. Biomass is a general term used to refer to the cells of the microorganisms that are using the material as a carbon source to grow on.

The coating may also comprise one or more biodegradable polymers. Said biodegradable polymer(s) may be one or more selected from starch based polymers as described herein above in this section and cellulose based polymers as described herein above in this section. However, the biodegradable polymer may also one or more selected from polyhydroxybutyrate (PHB), polyhydroxyvalerate (PHV), polyhydroxyvalerate-co-hydroxyvalerate (PHV/VH), Polyhydroxyalkanoates (PHA), poly-3-hydroxy-5-phenylvalerate (PHPV), aliphatic polyesters, polycaprolactone (PCL), polylactic acid (PLA), polyglycolic acid (PGA), copolymers or block copolymers of polycaprolactone (PCL), polylactic acid (PLA) and/or polyglycolic acid (PGA), polypropylene carbonate (PPC), polyester amide (PEA), polybutylene succinate adipate (PBSA), polybutylene adipate co-terephtalate (PBAT) and polybutylene succinate-adipate (PESA).

Copolymers or block copolymers of polycaprolactone (PCL), polylactic acid (PLA) and/or polyglycolic acid (PGA)

may, for example, be selected from, poly(lactic-co-glycolic acid) (PLGA), polylactic acid and epsilon-caprolactone copolymer (PLA/CL) and polylactic acid/glycolic acid polymers) (PLA/GA), which are all commercially available.

In one embodiment, the coating comprises one or more biodegradable polymers selected from polylactic acid (PLA), polycaprolactone (PCL) and polyhydroxybutyrate (PHB). In one such embodiment, the coating comprises both polylactic acid (PLA), polycaprolactone (PCL) and polyhydroxybutyrate (PHB).

The use of polycaprolactone and other polymers in this group has been increased over the last decade, while the demand for environmental friendly plastics has grown. These polymers are regarded as nontoxic and are already used in parenteral pharmaceutical formulations. The advantages of these polymers are their ability to make a more flexible coating when molded in mixture with starch derived polymers. The somewhat rigid structure of pure thermoplastic starch is improved. Furthermore the polymers are decomposable and disintegrate by microorganisms.

Polylactic Acid

Polylactic acid or polylactide (PLA) is a biodegradable, thermoplastic, aliphatic polyester derived from renewable resources, such as corn starch. PLA belongs to the chemical family of polyesters, such as for example ε-caprolactone. PLA-caprolactone contains PLA in different ratios from 15% PLA to 100% (such as 25, 35, 50, 75, 85%), polyglycolides, polyglycolic acids (PGA) and poly(lactide-co-glycolide) in different ratios from 15 to 100% PLA (such as 25, 35, 50, 75, 85%), poly(lactide-co-glycolide)-OH in different ratios from 15% PLA to 100% (such as 25, 35, 50, 75, 85%). Each of the before mentioned polymers exist in L or D-form (making them optically active) and in equal amounts (1:1) of L- and D-forms results in an amorphous mixture, while the L- or D-form all possess a certain degree of crystallinity. The degree of crystallinity is highly related to the mechanical properties (incl. processability), physico-chemical properties related to particularly stability of the polymer. A high degree of crystallinity provides hardness, and possibly, more brittleness. This may affect the processability as well, as highly crystalline materials have a high melting temperature and therefore processing temperature, while amorphous esters have a lower melting temperature and thus a lower processing temperature.

Moreover, an increased degree of crystallinity implies that the material is more thermodynamically stable, which leads to a longer shelf-life. Materials with a lower degree of crystallinity or amorphous materials are usually softer with a lower processing temperature. The drawback of amorphous materials or materials with a lower degree of crystallinity is that their physicochemical stability is lower as the material is in a thermodynamically unstable state.

Regarding PLA, it is necessary to find the optimal degree of crystallinity. Each degree of crystallinity has different mechanical properties, thus its adhesion to the matrix will vary depending on the degree of crystallinity of the given material (PLA).

The skeletal structure of PLA is shown below.

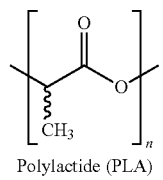

Polylactide (PLA)

Due to the chiral nature of lactic acid, several distinct forms of polylactide exist: poly-L-lactide (PLA in its L-form, see below figure) referred to as PLLA is the product resulting from polymerization of L,L-lactide (also known as L-lactide), and poly-D-lactide (PLA in its D-form) referred to as PDLA is the product resulting from polymerization of D-lactide.

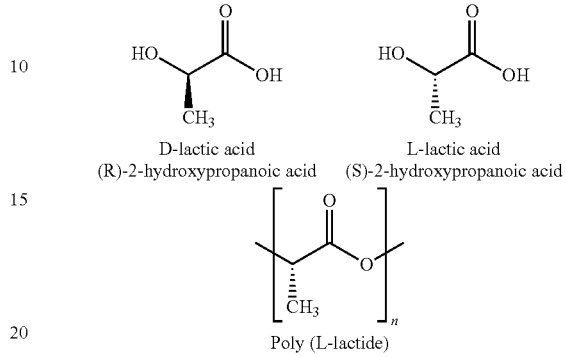

D-lactic acid
(R)-2-hydroxypropanoic acid

L-lactic acid
(S)-2-hydroxypropanoic acid

Poly (L-lactide)

Furthermore, PLLA and PDLA may be mixed using various ratios of the two stereo forms. As the L-form has stronger mechanical properties than the D-form, blends of the L- and D-forms can be prepared which have different morphological properties eg. by adding the D-form to the L-form in amounts of, for example, 5, 10, 20, 30, 40% w/w up to a ratio of 1:1, consequently making the material completely amorphous, however it may also form a highly regular stereo complex with increased crystallinity, since addition of PDLA increases the molecular energy of the mixture by forming a concentration gradient. Depending on the extent/magnitude of the temperature gradient, it may induce slow nucleation and hence crystallization. On the other hand, it may as well induce a nucleation with an incontrollable nucleation rate, which leads to an amorphous state.

PLA has in its L-form (PLLA) a crystallinity of around 35-45%, a glass transition temperature between 35-80° C. and a melting temperature between 173-178° C.

Due to the structure of PLA, PLA may be exposed to hydrolysis during its path through the gastro-intestinal tract, however PLA is impermeable and insoluble in aqueous media and in relation to applying PLA as shell material, it has been demonstrated that the shell at least macroscopically is intact within the first 48 hours of exposure. Furthermore, the possible degradation product of PLA is merely lactic acid.

Polyglycols

The coating may comprise any of the above-mentioned polyglycols in a form that erodes at a substantially slower rate than the matrix composition. The coating may thus be one which is eroded in an aqueous medium at a substantially slower rate than the matrix composition comprising the active drug substance, whereby the area of the matrix composition comprising the active drug substance that is exposed during erosion and/or release of the matrix composition is substantially controlled, and whereby the coating is substantially eroded upon erosion and/or release of the matrix composition comprising the active drug substance. Such a coating can be designed so that its longitudinal erosion rate is substantially the same as the longitudinal erosion and/or release rate of the matrix, whereby the matrix and the coating will erode longitudinally towards the centre of the composition at substantially the same rate. Thus, when the matrix composition has been completely eroded and/or released by the aqueous medium, the coating will also be substantially completely eroded. A matrix composition having such a coating has the obvious advantage of being completely biodegraded upon release of the active drug substance.

A polyglycol suitable for use within the coating is high molecular weight PEO, such as, for example, PEO with an average molecular weight which is significantly higher than the average molecular weight of any of the PEOs contained in the matrix composition. Thus, where the coating composition includes a PEO, the PEO contained in the coating can be selected to have a significantly higher average molecular weight than any PEO contained in the matrix. Examples of PEO materials suited to use in the coating include, for example, one or more PEO with an average molecular weight selected from at least 900,000, at least 2,000,000, at least 4,000,000, at least 6,000,000, or at least 7,000,000.

Mixtures of Polymers

As noted herein above the coating may comprise one or more different polymers, and in particular one or more different polymers selected from starch based polymers, cellulose based polymers, synthetic polymers and biodegradable polymers, in particular from any of the starch based polymers, cellulose based polymers, synthetic polymers and biodegradable polymers described herein above in this section.

In one embodiment of the invention, the coating comprises polymers selected from or even that all polymers of the coating are selected from starch based polymer and biodegradable polymers, such as from any of the starch based polymers and biodegradable polymers described herein above in this section. In particular, biodegradable polymers such as polycaprolactone, polyhydroxybuturate, polyhydroxyvalerate, polylactic acid, polyhydroxyalkanoates and/or polypropylene carbonate can be blended with various starches (such as any of the starches described herein above in this section) in different ratios. Suitable mixtures for use in the coating composition are for example polycaprolactone and sago and/or cassava starch, polycaprolactone or polyhydroxybuturate and pre-dried, thermoplastic starch, polycaprolactone and gelatinized starch or thermoplastic starch. Other suitable mixtures are starch-based blends with biodegradable thermoplastic components like polyester amide, polyhydroxybuturate-co-valerate or polybutylene succinate-adipate. Polymers starches can be cross-linked with maleic anhydride (MA) and dicumyl peroxide (DCP) giving harder items when molded and thermoformed.

In another embodiment, the coating comprises polymers selected from the starch based polymer and synthetic polymers described herein above in this section. In particular, suitable mixtures for use in the coating composition include, for example, native granular starch, modified starch, plasticized starch blended or grafted with many synthetic polymers such as polyethylene, polystyrene, Purified Terephthalic acid (PTA), optionally in mixture with aliphatic polyesters or polyvinyl alcohols in different ratios. Polybutylene succinate (PBS), polybutylene succinate adipate in blend with various starches in different ratios are also suitable, such as, for example, Polybutylene succinate in mixture with thermoplastic starch, alkylene oxide modified starches in combination with hydrolyzed polyvinyl alcohol.

In yet another embodiment, the coating comprises polymers selected from the cellulose based polymers and biodegradable polymers described herein above in this section. Thus, the coating may for example comprise a mixture of PLA and ethyl cellulose. In one embodiment the coating even consists of PLA, ethyl cellulose, one or more plasticizers (such as any of the plasticizers described herein below) and one or more UV stabilizers (such as any of the UV stabilizers described herein below).

UV Stabiliser

Radiation from sunlight can accelerate the degradation of plastics, such as the coating according to the invention. The packaging material to protect the immediate release compositions (for example tablets) from direct sunlight may not provide sufficient protection. Especially for a coating with high concentration of biodegradable polymers, it can be relevant to add UV-stabilizers to the compositions, due to the many unsaturated functional groups (eg. carbonyl groups). UV-stabilizers could for example be titanium dioxide, metal complexes with sulfur containing groups, hindered amine light stabilisers (HALS), benzophenones, benzotriazoles. Titanium dioxide is already widely used in pharmaceutical preparations as pigment and is considered non toxic.

Plasticizer

In addition to above mentioned polymers, the coating may comprise one or more additional components. Thus, the coating may comprise at least one selected from i) polymers which are soluble or dispersible in water,
ii) plasticizers, and
iii) fillers In a preferred embodiment the polymers, which are soluble or dispersible in water, are cellulose derivatives, which are soluble or dispersible in water. Thus, the coating material may comprise one or more plasticizers, preferably, any of the plasticizers described. Preferably, the coating material comprises one or more of the following plasticizers: Cetostearyl alcohol, castor oil, dibutyl sebacate, polyethylene oxides and/or Poloxamer; however other plasticizers may be contemplated to provide desired material properties.

Other suitable plasticizers may be selected from mono- and di-acetylated monoglycerides, diacetylated monoglycerides, acetylated hydrogenated cottonseed glyceride, glyceryl cocoate, Polyethylene glycols or polyethylene oxides (for example with a molecular weight of 1,000-500,000 daltons), dipropylene glycol salicylate glycerin, fatty acids and esters, phthalate esters, phosphate esters, amides, dioctyl phthalate, phthalyl glycolate, mineral oils, hydrogenated vegetable oils, vegetable oils, acetylated hydrogenated soybean oil glycerides, Castor oil, acetyl tributyl citrate, acetyl triethyl citrate, methyl abietate, nitrobenzene, carbon disulfide, β-naphtyl salicylate, sorbitol, sorbitol glyceryl tricitrate, fatty alcohols, cetostearyl alcohol, cetyl alcohol, stearyl alcohol, oleyl alcohol, myristyl alcohol, sucrose octaacetate, alfa-tocopheryl polyethylene glycol succinate (TPGS), tocopheryl derivative, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters, amyl oleate, butyl oleate, butyl stearate, diethylene glycol monolaurate, glycerol tributyrate, Flexol B-400, monomeric polyethylene ester, Piccolastic A-5, Piccalastic A-25, Clorafin 40, acetyl tributyl citrate, acetyl triethyl citrate, benzyl benzoate, butoxyethyl stearate, butyl and glycol esters of fatty acids, butyl diglycol carbonate, butyl ricinoleate, butyl phthalyl butyl glycolate, camphor, dibutyl sebacate, dibutyl tartrate, diphenyl oxide, glycerine, HB-40, hydrogenated methyl ester of rosin, methoxyethyl oleate, monoamylphthalate, Nevillac 10, Paracril 26, technical hydroabietyl alcohol, triethylene glycol dipelargonate, solid aliphatic alcohols and mixtures thereof.

In a preferred embodiment, the coating is made of a material wherein the concentration of plasticizer is from 0 to 30% w/w.

Accordingly it is preferred that the coating comprises or even consists of one or more plasticizer(s) and one or more polymer(s).

Furthermore, the coating may comprise sweetening agents, flavouring agents and/or colouring agents, which may be any of the sweetening agents, flavouring agents and/or colouring agents described herein.

The coating may be made of a material comprising one polymer, and wherein the concentration of the polymer is from 5% w/w to 100% w/w.

The coating may be made of a material comprising a mixture of polymers, and wherein the total concentration of polymers is from 70% w/w to 100% w/w.

Preferably, the coating comprises at least 50% w/w, more preferably at least 60% w/w, yet more preferably at least 70% w/w, even more preferably at least 80% w/w in total of polymers substantially insoluble in water as described herein above.

Thus, in preferred embodiments, wherein the coating comprises cellulose derivatives (such as ethyl cellulose), then the coating preferably comprises at least 50% w/w, more preferably at least 60% w/w, yet more preferably at least 70% w/w, even more preferably at least 80% w/w, such as at least 85% w/w, for example 87% w/w cellulose derivative (such as ethyl cellulose).

In a preferred embodiment the coating comprises at the most 19% w/w, more preferably at the most 15% w/w, such as at the most 12% w/w, for example 12% w/w plasticizer (such as cetostearyl alcohol).

Thus, in preferred embodiments, wherein the coating comprises biodegradable polymers (such as polylactic acid), then the coating preferably comprises at least 50% w/w, more preferably at least 60% w/w, yet more preferably at least 70% w/w, even more preferably at least 80% w/w, such as at least 85% w/w, for example 86% w/w biodegradable polymers (such as polylactic acid).

In a preferred embodiment the coating comprises at the most 20% w/w, more preferably at the most 17% w/w, such as at the most 15% w/w, for example 14% w/w plasticizer (polyethylene oxides 200,000 Daltons).

Outer Coat

In some cases the immediate release composition of the present invention may also comprise an outer coat that fully covers the composition, i.e. the matrix and the coating. Said outer coat may be selected from taste masking coats, coats with aqueous moisture barriers and/or oxidative barriers to improve the stability of the immediate release composition, and cosmetic coats for example a coat containing colouring agents, sweetening agents and/or flavouring agents in order to provide an elegant and palatable tablet and/or to provide easily distinguishable dose strengths. Especially, it is preferred to coat immediate release compositions having different strengths with outer coats of different colours, so that the different dose strengths are easily distinguished. Preferably, the outer coat is easily soluble in aqueous media in order to provide that the matrix comes in contact with the surrounding aqueous media via the openings in the coating immediately after administration.

Preparation

The immediate release composition as well as the matrix composition of the invention may be produced by various methods which are either known per se in the pharmaceutical industry or which, for example, are used in the production of polymer-based materials, depending upon the desired embodiment and the materials employed in the immediate release composition in question. One advantage of the immediate release composition according to the invention is that it may be produced by methods which are relatively simple and inexpensive.

Suitable preparation methods for immediate release compositions according to the invention include extrusion, injection moulding, melt-processing, tabletting, capsule filling, thermoforming, spray coating, micro encapsulation and other methods of preparing immediate release compositions. Also a combination of one or more of the aforementioned methods may be employed.

Immediate release compositions according to the invention may be prepared in numerous ways giving rise to different release mechanisms. Particularly the immediate release composition may be prepared by 1, 2 or multiple component injection mouldings, by conventional tablet compression, by micro encapsulation, by 1, 2 or multiple component extrusions, by capsule filling, by melt-processing or by thermoforming. The preparation may also comprise separate steps as for example wet granulation, dry granulation, melt granulation, pelletizing, spray coating, electrostatic coating or other forms of preparation methods.

DEFINITIONS

In the present context, the term "swellable" is intended to mean that the material increase/expand in size and volume as a result of contact with liquid.

In the present context, the term "immediate release" denotes a composition that disintegrates within at the most 60 minutes such as, for example, at the most 30 minutes or at the most 15 minutes, when subjected to a disintegration test according to Ph. Eur.

In the present context, the term "resistant to abuse by alcohol" is intended to mean that the in vitro dissolution behaviour of an immediate release composition of the invention is the same or shows a decreased release rate when the composition is tested in a dissolution medium. The ratio ($R_{50}$) between $t_{50\%\ w/w}$ (40% v/v ethanol in medium 1) and $t_{50\%\ w/w}$ (medium 1) is 1.5 or more. $t_{50\%\ w/w}$ (medium 1) denotes the time it takes to release 50% w/w of the drug substance from the immediate release composition in an in vitro dissolution test according to USP 32, NF 27, (711), Apparatus 2, paddle employing water optionally buffered/adjusted to a specific pH as dissolution medium (medium 1), and $t_{50\%\ w/w}$ (40% v/v ethanol in medium 1) denotes the time it takes to release 50% w/w of the drug substance from the immediate release composition in an in vitro dissolution test according to USP 32, NF 27, (711), Apparatus 2, paddle employing 40% v/v ethanol in medium 1 as dissolution medium.

The same may also apply for ratios determined for example when 25% w/w, 30% w/w, 40% w/w, 60% w/w, 70% w/w, 80% w/w, 90% w/w and/or 95% w/w has been released, the conditions being as described above.

In the present context, the term "abuse" is intended to denote the use of a drug in order to induce euphoria or another excitement effect, i.e. the use is not intended to cure a disease or alleviate disease symptoms, but rather for obtaining intoxication.

In the present context, the term "alcoholic beverage" is intended to mean a liquid or brew containing more than 4% v/v ethanol and the volume of an alcoholic beverage is 0.4 L or more.

In the present context, the term "ingest 3 or more alcoholic beverages daily" is intended to mean that the subject on an average daily basis ingests liquid or brew with a total content of 100% v/v ethanol of 40 ml or more. The number of alcoholic beverages is not that important, it is the total amount of alcohol ingested daily that is important. The term "average daily basis" is determined as the total intake during a week divided by 7.

The following methods and examples are intended to illustrate the invention and are not intended to limit the invention in any way.

EXPERIMENTAL

Dissolution Test

Dissolution tests were performed in accordance with USP 32, NF 27, (711), Apparatus 2 (paddle method). The dissolution medium consisted of ethanol and/or phosphate buffer solution pH 6.8, or ethanol and/or hydrochloride solution pH 1.2. The volume of the dissolution medium was 900 ml and the rotation speed of the paddles was 50 rpm throughout the dissolution run. The temperature was 37° C. Samples were withdrawn at suitable time intervals and analysed for content of drug substance by means of UV-detector or HPLC with UV-detector at a wavelength relevant for the particular drug substance. In the case of Paracetamol (Acetaminophen) a relevant wavelength is 280 nm. In the case of morphine, a relevant wavelength is 284 nm. The specific drug substances analysed for are described in the examples herein.

Methods

A general method for the preparation of an immediate release pharmaceutical composition according to the present invention is described below.

Preparation of a Matrix Composition

An accurate amount of the polymer is weighed into a beaker followed by an accurate amount of the drug substance and of other pharmaceutically acceptable excipient(s), if any. The mixing is performed on a magnetic stirrer at up to 800 rpm for a time period up to 20 minutes. The mixing is performed at room temperature throughout the mixing process. The mixture is now ready to be fed into an injection moulding machine.

3 g of the mixture is then fed into a table top injection moulding machine (Haake MiniJet II, Thermo Electron, Karlsruhe, Germany) and moulded directly into a pre-moulded shell with a weight of approximately 160 mg to receive a total tablet weight of approximately 350 mg. The settings applied in the MiniJet are: Temperature 40-65° C., pressure 150-800 bar and time 10-30 seconds.

Preparation of the Coating/Shell Composition

The coating composition is prepared by first adding the ethylcellulose then cetostearyl alcohol, and finally the titanium dioxide to a MTI-Mixer at room temperature. After mixing at around 1000 rpm the mixer is stopped when the temperature reaches 40-50° C. and the adhered material is manually incorporated into the mixture. The mixture is left to cool for about 10 minutes. The mixing is then finalized with a short high-speed mix in order to minimize lump formation. The mixture is then allowed to cool to room temperature, after which it had a suitable consistency for being fed into an injection moulding machine. The injection moulding machine used is Arburg Allrounder 420 V 800-60/35.

Example of Coat Composition
Batch: 08-0017-058

| Material | % (w/w) |
|---|---|
| Ethocel | 87 |
| Cetostearyl Alcohol | 12 |
| TiO2 | 1 |
| Total | 100 |

Preparation of a Pharmaceutical Composition in Large Scale

The shell and matrix are moulded in one process, where the shell is moulded in a first step and the matrix is moulded directly into the coat in a second step (co-moulding or 2 component moulding). The injection moulding machine used is Arburg Allrounder 420 V 800-60/35.

In all the examples 1 to 21 the immediate release composition was 9 mm long, of cylindrical shape and with oval end surfaces.

Example 1

Preparation of an Immediate Release Composition Containing Hydrocodone and Paracetamol A composition (batch No. 1049-031) according to the invention was prepared from the following ingredients:

|  | % (w/w) |
|---|---|
| Matrix | |
| Paracetamol | 70 |
| Hydrocodone | 2.1 |
| PEG 3350 S | 20.9 |
| Citric acid | 2 |
| Sodium bicarbonate | 5 |
| Shell/coat | |
| Ethylcellulose | 87 |
| Cetostearyl alcohol | 12 |
| Titanium dioxide | 1 |

The composition was prepared as described above.

The content of Hydrocodone in the formulation was 0.126 g and the content of paracetamol in the formulation was 4.2 g and the total mass was 6 gram. The mass of the matrix in the composition was approximately 180 mg.

The composition was subjected to the dissolution test described above. In addition to phosphate buffer medium, testing was performed in medium containing ethanol at the ratio 60:40 (v/v). The following results were obtained:

| Time (minutes) | % w/w release of Buffer | Paracetamol from the composition Buffer:Ethanol 60:40 |
|---|---|---|
| 15 | 100 | 29 |
| 75 | 100 | 100 |

| Ratio ($R_{50}$) | $t_{50\% w/w}$ (min) in Buffer | $t_{50\% w/w}$ (min) in Buffer:Ethanol 60:40 |
|---|---|---|
| 7.13 | 0.08 | 0.57 |

The ratio ($R_{50}$) between $t_{50\% w/w}$ (40% v/v ethanol in buffer) and $t_{50\% w/w}$ (buffer) is 7.13.

Example 2

Basic Formulation with a Low Chain Polymeric Carrier, PEG 3350

A composition (batch no. 1569-034) according to the invention was prepared from the following ingredients:

|  | % (w/w) |
| --- | --- |
| Matrix | |
| Acetaminophen | 50.0 |
| Hydrocodone | 0.5 |
| PEG3350S | 49.5 |
| Shell/coat | |
| Ethylcellulose | 87 |
| Cetostearyl alcohol | 12 |
| Titanium dioxide | 1 |

The dissolution profiles are shown in FIG. 1.

As seen in the figure, no delay in release rate was noticed when neither effervescent nor disintegrant were added to the formulation. In fact, the release in alcohol was faster compared to that in pure HCl-solution.

Example 3

Basic Formulation with a Low Chain Polymeric Carrier, PEG 6 000

A composition (batch no. 1564-036) according to the invention was prepared from the following ingredients:

|  | % (w/w) |
| --- | --- |
| Matrix | |
| Acetaminophen | 50.0 |
| Hydrocodone | 0.5 |
| PEG 6000 | 49.5 |
| Shell/coat | |
| Ethylcellulose | 87 |
| Cetostearyl alcohol | 12 |
| Titanium dioxide | 1 |

The dissolution profiles are shown in FIG. 2.

As seen in the figure, no delay in release rate was noticed when neither effervescent nor disintegrant were added to the formulation. In fact, the release in alcohol was faster compared to that in pure HCl solution.

Example 4

Basic Formulation with a High Chain Polymeric Carrier, PEG 17 000

A composition (batch no. 1564-044) according to the invention was prepared from the following ingredients:

|  | % (w/w) |
| --- | --- |
| Matrix | |
| Acetaminophen | 50.0 |
| Hydrocodone | 0.5 |
| PEG 17 000 | 49.5 |
| Shell/coat | |
| Ethylcellulose | 87 |
| Cetostearyl alcohol | 12 |
| Titanium dioxide | 1 |

The dissolution profiles are shown in FIG. 3.

As seen in the figure, no delay in release rate was noticed when neither effervescent nor disintegrant were added to the formulation. In fact, the release in alcohol is faster compared to that in pure HCl-solution. Thereby it was seen, that the polymeric carrier does not influence the release displacement in alcohol compared to HCL solution.

Example 5

Influence on Release Profile when Effervescent is Added to the Formulation, Based on a Low Chain Polymeric Carrier PEG 3350

A composition (batch no. 1569-032) according to the invention was prepared from the following ingredients:

|  | % (w/w) |
| --- | --- |
| Matrix | |
| Acetaminophen | 50.0 |
| Hydrocodone | 0.5 |
| Citric acid | 2.0 |
| NaHCO$_3$ | 5.0 |
| PEG 3350S | 42.5 |
| Shell/coat | |
| Ethylcellulose | 87 |
| Cetostearyl alcohol | 12 |
| Titanium dioxide | 1 |

The dissolution profiles are shown in FIG. 4.

As seen in the figure, a delay in release rate of approximately 30 min. in alcohol compared to HCL solution was noticed when effervescent was added to the formulation.

Example 6

Influence on Release Profile when Effervescent is Added to the Formulation, Based on a Low Chain Polymeric Carrier PEG 6000

A composition (batch no. 1568-009) according to the invention was prepared from the following ingredients:

|  | % (w/w) |
| --- | --- |
| Matrix | |
| Acetaminophen | 50.0 |
| Hydrocodone | 0.5 |
| Citric acid | 2.0 |
| NaHCO$_3$ | 5.0 |
| PEG 6000 | 42.5 |
| Shell/coat | |
| Ethylcellulose | 87 |
| Cetostearyl alcohol | 12 |
| Titanium dioxide | 1 |

The dissolution profiles are shown in FIG. 5.

As seen in the figure, a delay in release rate of approximately 30 minutes in alcohol compared to HCl solution was noticed when effervescent was added to the formulation.

Example 7

Influence on Release Profile when Effervescent is Added to the Formulation, Based on a High Chain Polymeric Carrier PEG 17 000

A composition (batch no. 1564-058) according to the invention was prepared from the following ingredients:

|  | % (w/w) |
| --- | --- |
| Matrix | |
| Acetaminophen | 50.0 |
| Hydrocodone | 0.5 |
| Citric acid | 4.0 |
| NaHCO$_3$ | 10.0 |
| PEG 17 000 | 35.5 |
| Shell/coat | |
| Ethylcellulose | 87 |
| Cetostearyl alcohol | 12 |
| Titanium dioxide | 1 |

The dissolution profiles are shown in FIG. 6.

As seen in the figure, a delay in release rate of approximately 30 minutes in alcohol compared to HCl solution was noticed when effervescent was added to the formulation.

Example 8

Influence on Release Profile when Disintegrant is Added to the Formulation, Based on a Low Chain Polymeric Carrier PEG 6000

A composition (batch no. 1564-032) according to the invention was prepared from the following ingredients:

|  | % (w/w) |
| --- | --- |
| Matrix Composition: | |
| Acetaminophen | 50.0 |
| Hydrocodone | 0.5 |
| PEG 6000 | 39.5 |
| Cross-caramellose Na | 10.0 |
| Shell/coat | |
| Ethylcellulose | 87 |
| Cetostearyl alcohol | 12 |
| Titanium dioxide | 1 |

The dissolution profiles are shown in FIG. 7.

As seen in the figure, the release in alcohol was faster compared to that in pure HCl-buffer.

Example 9

Influence on Release Profile when a Combination of Effervescent and Disintegrant is Added to the Formulation, Based on a High Chain Polymeric Carrier PEG 17 000

A composition (batch no. 1564-066) according to the invention was prepared from the following ingredients:

|  | % (w/w) |
| --- | --- |
| Matrix | |
| Acetaminophen | 50.0 |
| Hydrocodone | 0.5 |
| Citric acid | 4.0 |
| NaHCO$_3$ | 10.0 |
| Cross-caramellose Na | 5.0 |
| PEG 17 000 | 30.5 |
| Shell/coat | |
| Ethylcellulose | 87 |
| Cetostearyl alcohol | 12 |
| Titanium dioxide | 1 |

The dissolution profiles are shown in FIG. 8.

As seen in the figure, a delay in release rate of approximately 35 minutes in alcohol compared to HCl solution was noticed.

Example 10

Influence on Release Profile when a Combination of Effervescent and Disintegrant is Added to the Formulation, Based on a Medium/High Chain Polymeric Carrier PEG 14 000

A composition (batch no. 1564-082) according to the invention was prepared from the following ingredients:

|  | % (w/w) |
| --- | --- |
| Matrix | |
| Acetaminophen | 50.0 |
| Hydrocodone | 0.5 |
| Citric acid | 3.0 |
| NaHCO$_3$ | 7.5 |
| Cross-caramellose Na | 12.5 |
| PEG 14 000 | 26.5 |
| Shell/coat | |
| Ethylcellulose | 87 |
| Cetostearyl alcohol | 12 |
| Titanium dioxide | 1 |

The dissolution profiles are shown in FIG. 9.

As seen in the figure, a delay in release rate of approximately 40 minutes in alcohol compared to HCl solution was noticed.

Example 11

Influence on Release Profile when a Combination of Effervescent and Disintegrant is Added to the Formulation, Based on a Medium Chain Polymeric Carrier PEG 10 000

A composition (batch no. 1569-014) according to the invention was prepared from the following ingredients:

|  | % (w/w) |
| --- | --- |
| Matrix Composition: | |
| Acetaminophen | 50.0 |
| Hydrocodone | 0.5 |

|  | % (w/w) |
| --- | --- |
| Citric acid | 2.5 |
| NaHCO$_3$ | 6.25 |
| Cross-caramellose Na | 12.5 |
| PEG 10 000 | 28.25 |
| Shell/coat | |
| Ethylcellulose | 87 |
| Cetostearyl alcohol | 12 |
| Titanium dioxide | 1 |

The dissolution profiles are shown in FIG. 10.

As seen in the figure, a delay in release rate of approximately 60 minutes in alcohol compared to HCl solution was noticed.

Example 12

Influence on Release Profile when a Combination of Effervescent and Disintegrant is Added to the Formulation, Based on a Low/Medium Chain Polymeric Carrier PEG 6000

A composition (batch no. 1569-020) according to the invention was prepared from the following ingredients:

|  | % (w/w) |
| --- | --- |
| Matrix | |
| Acetaminophen | 50.0 |
| Hydrocodone | 0.5 |
| Citric acid | 2.0 |
| NaHCO$_3$ | 5.0 |
| Cross-caramellose Na | 12.5 |
| PEG 6 000 | 30 |
| Shell/coat | |
| Ethylcellulose | 87 |
| Cetostearyl alcohol | 12 |
| Titanium dioxide | 1 |

The dissolution profiles are shown in FIG. 11.

As seen in the figure, a delay in release rate of approximately 45 minutes in alcohol compared to HCl solution was noticed.

Example 13

Influence on Release Profile when a Combination of Effervescent and Disintegrant is Added to the Formulation, Based on a Low Chain Polymeric Carrier PEG 3350

A composition (batch no. 1569-016) according to the invention was prepared from the following ingredients:

|  | % (w/w) |
| --- | --- |
| Matrix | |
| Acetaminophen | 50.0 |
| Hydrocodone | 0.5 |
| Citric acid | 2 |
| NaHCO$_3$ | 5 |
| Cross-caramellose Na | 12.5 |
| PEG 3350 | 30 |

|  | % (w/w) |
| --- | --- |
| Shell/coat | |
| Ethylcellulose | 87 |
| Cetostearyl alcohol | 12 |
| Titanium dioxide | 1 |

The dissolution profiles are shown in FIG. 12.

As seen in the figure, a delay in release rate of approximately 30 minutes in alcohol compared to HCl solution was noticed.

Example 14

Influence on Release Profile when the Effervescent Comprises Tartaric Acid and NaHCO$_3$ Using a Low/Medium Chain Polymeric Carrier PEG 6 000

A composition (batch no. 1564-060) according to the invention was prepared from the following ingredients:

|  | % (w/w) |
| --- | --- |
| Matrix | |
| Acetaminophen | 50.0 |
| Hydrocodone | 0.5 |
| Tartaric acid | 2.0 |
| NaHCO$_3$ | 5.0 |
| PEG 6 000 | 42.5 |
| Shell/coat | |
| Ethylcellulose | 87 |
| Cetostearyl alcohol | 12 |
| Titanium dioxide | 1 |

The dissolution profiles are shown in FIG. 13.

As seen in the figure, a small delay in release rate of approximately 20 minutes in alcohol compared to HCl solution was noticed when approximately the same amount of tartaric acid was used compared to citric acid.

Example 15

Influence on Release Profile when the Effervescent Comprises Tartaric Acid and NaHCO$_3$ Using a Low/Medium Chain Polymeric Carrier PEG 6 000

A composition (batch no. 1564-064) according to the invention was prepared from the following ingredients:

|  | % (w/w) |
| --- | --- |
| Matrix | |
| Acetaminophen | 50.0 |
| Hydrocodone | 0.5 |
| Tartaric acid | 4.0 |
| NaHCO$_3$ | 5.0 |
| PEG 6 000 | 40.5 |
| Shell/coat | |
| Ethylcellulose | 87 |
| Cetostearyl alcohol | 12 |
| Titanium dioxide | 1 |

The dissolution profiles are shown in FIG. 14.

As seen in the figure, a delay in release rate of approximately 30 minutes in alcohol compared to HCl solution was noticed. Comparing example 6 with example 14 and 15 demonstrates that twice as much tartaric acid is required to achieve a similar time delay in alcohol compared to the required amount of citric acid.

Example 16

Influence on Release Profile when the Effervescent Comprises Succinic Acid and $NaHCO_3$ Using a Low/Medium Chain Polymeric Carrier PEG 6 000

A composition (batch no. 1564-056) according to the invention was prepared from the following ingredients:

| Matrix | % (w/w) |
|---|---|
| Acetaminophen | 50.0 |
| Hydrocodone | 0.5 |
| Succinic acid | 2.0 |
| $NaHCO_3$ | 5.0 |
| PEG 6 000 | 42.5 |

The dissolution profiles are shown in FIG. 15.

As seen in the figure, a delay in release rate of approximately 30 minutes in alcohol compared to HCl solution was noticed.

Example 17

Influence on Release Profile when the Effervescent Comprises Malonic Acid and $NaHCO_3$ Using a Low/Medium Chain Polymeric Carrier PEG 6 000

A composition (batch no. 1569-036) according to the invention was prepared from the following ingredients:

| | % (w/w) |
|---|---|
| Matrix | |
| Acetaminophen | 50.0 |
| Hydrocodone | 0.5 |
| Malonic acid | 4.0 |
| $NaHCO_3$ | 5.0 |
| PEG 6 000 | 40.5 |
| Shell/coat | |
| Ethylcellulose | 87 |
| Cetostearyl alcohol | 12 |
| Titanium dioxide | 1 |

The dissolution profiles are shown in FIG. 16.

As seen in the figure, a delay in release rate of approximately 20 minutes in alcohol compared to HCl solution was noticed.

Example 18

Influence on Release Profile when the Effervescent Comprises Benzoic Acid and $NaHCO_3$ Using a Low/Medium Chain Polymeric Carrier PEG 6 000

A composition (batch no. 1569-038) according to the invention was prepared from the following ingredients:

| | % (w/w) |
|---|---|
| Matrix | |
| Acetaminophen | 50.0 |
| Hydrocodone | 0.5 |
| Benzoic acid | 4.0 |
| $NaHCO_3$ | 5.0 |
| PEG 6 000 | 40.5 |
| Shell/coat | |
| Ethylcellulose | 87 |
| Cetostearyl alcohol | 12 |
| Titanium dioxide | 1 |

The dissolution profiles are shown in FIG. 17.

As seen in the figure, a delay in release rate of approximately 25 minutes in alcohol compared to HCl solution was noticed.

Example 19

Influence on Release Profile when the Effervescent Comprises Oxalic Acid and $NaHCO_3$ Using a Low/Medium Chain Polymeric Carrier PEG 6 000

A composition (batch no. 1564-040) according to the invention was prepared from the following ingredients:

| | % (w/w) |
|---|---|
| Matrix | |
| Acetaminophen | 50.0 |
| Hydrocodone | 0.5 |
| Oxalic acid | 4.0 |
| $NaHCO_3$ | 5.0 |
| PEG 6 000 | 40.5 |
| Shell/coat | |
| Ethylcellulose | 87 |
| Cetostearyl alcohol | 12 |
| Titanium dioxide | 1 |

The dissolution profiles are shown in FIG. 18.

As seen in the figure, a delay in release rate of approximately 50 minutes in alcohol compared to HCl solution was noticed.

Example 20

Influence on Release Profile when the Effervescent Comprises Malic Acid and $NaHCO_3$ Using a Low/Medium Chain Polymeric Carrier PEG 6 000

A composition (batch no. 1564-042) according to the invention was prepared from the following ingredients:

| | % (w/w) |
|---|---|
| Matrix | |
| Acetaminophen | 50.0 |
| Hydrocodone | 0.5 |
| Malic acid | 4.0 |
| $NaHCO_3$ | 5.0 |
| PEG 6 000 | 40.5 |
| Shell/coat | |
| Ethylcellulose | 87 |
| Cetostearyl alcohol | 12 |
| Titanium dioxide | 1 |

The dissolution profiles are shown in FIG. 19.

As seen in the figure, a delay in release rate of approximately 20 minutes in alcohol compared to HCl solution was noticed.

Example 21

Influence on Release Profile when the Effervescent Comprises Glutaric Acid and NaHCO$_3$ Using a Low/Medium Chain Polymeric Carrier PEG 6 000

A composition (batch no. 1564-044) according to the invention was prepared from the following ingredients:

|  | % (w/w) |
|---|---|
| Matrix | |
| Acetaminophen | 50.0 |
| Hydrocodone | 0.5 |
| Glutaric acid | 4.0 |
| NaHCO$_3$ | 5.0 |
| PEG 6 000 | 40.5 |
| Shell/coat | |
| Ethylcellulose | 87 |
| Cetostearyl alcohol | 12 |
| Titanium dioxide | 1 |

The dissolution profiles are shown in FIG. 20.

As seen in the figure, a delay in release rate of approximately 25 minutes in alcohol compared to HCl solution was noticed.

Example 22

Influence on Release Profile, when a Combination of Effervescent and Disintegrant is Added to the Formulation, Based on a Low/Medium Chain Polymeric Carrier PEG 6000

A composition (batch no. 1569-046) according to the invention was prepared from the following ingredients:

|  | % (w/w) |
|---|---|
| Matrix | |
| Morphine sulphate pentahydrate | 5.0 |
| Citric acid | 2.5 |
| NaHCO$_3$ | 6.25 |
| Cross-caramellose Na | 12.5 |
| PEG 6000 | 73.75 |
| Shell/coat | |
| Ethylcellulose | 87 |
| Cetostearyl alcohol | 12 |
| Titanium dioxide | 1 |

The dissolution profiles are shown in FIG. 21.

As seen in the figure, a delay in release rate of approximately 75 minutes in alcohol compared to HCl solution was noticed.

Example 23

Influence on Release Profile, when a Combination of Effervescent and Disintegrant is Added to the Formulation, Based on a Low/Medium Chain Polymeric Carrier PEG 6000

A composition (batch no. 1569-048) according to the invention was prepared from the following ingredients:

|  | % (w/w) |
|---|---|
| Matrix | |
| Morphine sulphate pentahydrate | 5.0 |
| Citric acid | 6.0 |
| NaHCO$_3$ | 15 |
| Cross-caramellose Na | 12.5 |
| PEG 6000 | 61.5 |
| Shell/coat | |
| Ethylcellulose | 87 |
| Cetostearyl alcohol | 12 |
| Titanium dioxide | 1 |

The dissolution profiles are shown in FIG. 22.

As seen in the figure, a delay in release rate of approximately 45 minutes in alcohol compared to HCl solution was noticed.

Example 24

Influence on Release Profile, when a Combination of Effervescent and Disintegrant is Added to the Formulation, Based on a High Chain Polymeric Carrier PEG 17 000

A composition (batch no. 1569-050) according to the invention was prepared from the following ingredients:

|  | % (w/w) |
|---|---|
| Matrix | |
| Morphine sulphate pentahydrate | 5.0 |
| Citric acid | 2.5 |
| NaHCO$_3$ | 6.25 |
| Cross-caramellose Na | 12.5 |
| PEG 17 000 | 73.75 |
| Shell/coat | |
| Ethylcellulose | 87 |
| Cetostearyl alcohol | 12 |
| Titanium dioxide | 1 |

The dissolution profiles are shown in FIG. 23.

As seen in the figure, a delay in release rate of approximately 75 minutes in alcohol compared to HCl solution was noticed.

The invention claimed is:

1. An immediate release pharmaceutical composition resistant to alcohol-induced dose dumping, consisting of a single polymer matrix optionally provided with a coating, wherein the single polymer matrix has one or more drug substances dispersed therein and comprises (i) from about 30% to about 95% w/w of one or more polyglycols having a molecular weight of from about 900 to about 17,000 Daltons and (ii) one or more effervescent agents, and is resistant to alcohol-induced dose dumping.

2. The pharmaceutical composition according to claim 1, wherein the polymer matrix further comprises one or more disintegrants.

3. The pharmaceutical composition according to claim 2, wherein the one or more disintegrants is selected from the group consisting of sodium starch glycolate, povidone, sodium alginate, alginic acid, calcium alginate, carboxymethylcellulose calcium, carboxymethylcellulose sodium, powdered cellulose, chitosan, croscarmellose sodium, crospovidone, cross-linked polyvinylpyrrolidone, hydroxypropyl starch, hydroxypropyl cellulose low-substituted, magnesium aluminium silicate, methylcellulose, microcrystalline cellulose, pregelatinized starch, docusae sodium, guar gum, and polacrilin potassium.

4. The pharmaceutical composition according to claim 2, wherein the one or more disintegrants are present in the composition at a total amount of from about 1% to about 60% by weight.

5. The pharmaceutical composition according to claim 2, wherein the one or more disintegrants are present in the composition at a total amount of from about 5% to about 50% by weight of the polymer matrix.

6. The pharmaceutical composition according to claim 2, wherein the total amount of the one or more effervescent agents and the one or more disintegrants is from about 1° A w/w to about 80% by weight of the polymer matrix.

7. The pharmaceutical composition according to claim 1, wherein the one or more effervescent agents comprise an effervescent couple comprising a water soluble organic acid and a water soluble bicarbonate.

8. The pharmaceutical composition according to claim 7, wherein the water soluble organic acid is selected from the group consisting of citric acid, tartaric acid, succinic acid, malonic acid, benzoic acid, oxalic acid, malic acid and glutaric acid.

9. The pharmaceutical composition according to claim 7, wherein the water soluble bicarbonate comprises $NaHCO_3$.

10. The pharmaceutical composition according to claim 1, wherein the polymer matrix comprises a polyglycol having an average molecular weight selected from the group consisting of 1000, 1100, 1900, 2000, 2800, 2900, 3350, 4400, 5800, 6000, 8000, 8400, 10,000, 12,000, 14,600, and 17,000 Daltons.

11. The pharmaceutical composition according to claim 1, wherein the polymer matrix comprises one or more polyglycols having a molecular weight selected from the group consisting of PEG 3350, PEG 6000, and PEG 17,000.

12. The pharmaceutical composition according to claim 1, wherein the one or more drug substances is selected from the group consisting of anaesthetics, analgesics, opioids, antipyretics, antimigraine agents, antiepileptics, anti-parkinson agents, dopaminergic agents, antipsychotics, anxiolytics, sedatives, antidepressants, psychostimulating agents used for ADHD and nootropics, and agents used in addictive disorders.

13. The pharmaceutical composition according to claim 1, wherein the one or more drug substances is released from the composition in the stomach with a release profile that is dependent on the concentration of ethanol, such that an increased ethanol concentration results in a decreased rate of drug release.

14. The pharmaceutical composition according to claim 1, wherein the composition is resistant to alcohol-induced dose dumping when the alcohol is ingested together with the composition or within a period of up to 60 minutes before and up to 60 minutes after ingesting the composition.

15. The pharmaceutical composition according to claim 1, wherein the composition is resistant to abuse by intake of alcohol when the alcohol is ingested together with the composition or within a period of up to 60 minutes before and up to 60 minutes after the intake of the composition.

16. The pharmaceutical composition according to claim 1, wherein the ratio ($R_{50}$) of the time it takes to release 50% w/w of the drug substance from the pharmaceutical composition ($t_{50\%}$) in a medium ethanol and dilute hydrochloric acid (pH 1.2) or phosphate buffer (pH 6.8) at a ratio of 40:60 (v/v) to the time it takes to release 50% w/w of the drug substance from the pharmaceutical composition ($t_{50\%}$)) in a medium of dilute hydrochloric acid (pH 1.2) or phosphate buffer (pH 6.8) is 1.5 or more, when the pharmaceutical composition is subject to in vitro dissolution test according to USP 32, NF 27, (711), Apparatus 2, paddle.

17. The pharmaceutical composition according to claim 1, wherein the polymer matrix is provided with the coating.

18. The pharmaceutical composition according to claim 17, wherein the coating is impermeable to and insoluble in an aqueous medium.

19. A method of administering an immediate release pharmaceutical composition to a patient that ingests three or more alcoholic beverages daily, comprising orally administering a pharmaceutical composition according to claim 1 to the patient.

* * * * *